(12) United States Patent
Miyatake et al.

(10) Patent No.: US 11,820,738 B2
(45) Date of Patent: Nov. 21, 2023

(54) METHOD FOR PRODUCING SECONDARY ALCOHOL ALKOXYLATE

(71) Applicant: NIPPON SHOKUBAI CO., LTD., Osaka (JP)

(72) Inventors: Tomoki Miyatake, Kawasaki (JP); Akimasa Watanabe, Kawasaki (JP); Shunsuke Iwakura, Kawasaki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 30 days.

(21) Appl. No.: 17/649,082

(22) Filed: Jan. 27, 2022

(65) Prior Publication Data

US 2022/0251013 A1 Aug. 11, 2022

(30) Foreign Application Priority Data

Feb. 1, 2021 (JP) .................................. 2021-014164
Feb. 1, 2021 (JP) .................................. 2021-014167

(51) Int. Cl.
*C07C 41/03* (2006.01)

(52) U.S. Cl.
CPC .................................... *C07C 41/03* (2013.01)

(58) Field of Classification Search
CPC .................................................... C07C 41/03
See application file for complete search history.

(56) References Cited

U.S. PATENT DOCUMENTS

2010/0267844 A1* 10/2010 Varineau ................. A61P 43/00
162/158

FOREIGN PATENT DOCUMENTS

JP    S52-151108 A    12/1977
JP    S61-186337 A    8/1986

OTHER PUBLICATIONS

JPO, Notice of reason for rejection for the Japanese Patent Application No. 2021-014167, dated Apr. 27, 2021, with English translation.

* cited by examiner

*Primary Examiner* — Rosalynd A Keys
(74) *Attorney, Agent, or Firm* — LUCAS & MERCANTI, LLP

(57) ABSTRACT

The present invention is to provide a means that can reduce coloring of secondary alcohol alkoxylate. The present invention relates to a method for producing a secondary alcohol alkoxylate which comprises feeding an alkylene oxide from a plurality of positions in a tubular reactor to a secondary alcohol to react them, wherein the alkylene oxide is fed in such a manner that a feeding interval is extended and a feeding rate is increased each with a specific proportion.

14 Claims, 5 Drawing Sheets

METHOD FOR PRODUCING SECONDARY ALCOHOL ALKOXYLATE

CROSS-REFERENCE TO RELATED APPLICATION

This application claims the benefit of Japanese Patent Application Nos. 2021-014164 and 2021-014167 filed on Feb. 1, 2021, the entire disclosure of which is incorporated herein by reference.

BACKGROUND

1. Technological Field

The present invention relates to a method for producing a secondary alcohol alkoxylate.

2. Description of the Related Art

Secondary alcohol alkoxylates including secondary alcohol ethoxylates have been widely used as a nonionic surfactant because of easiness in handling and their low pour points. Such secondary alcohol alkoxylate is produced by adding alkylene oxide to secondary alcohol, as a starting material, in the presence of an alkaline catalyst such as sodium hydroxide, potassium hydroxide, and sodium alkoxide or an acid catalyst such as boron trifluoride, a boron trifluoride complex, antimony pentachloride, and tin tetrachloride (e.g., Japanese Patent Laid-Open No. S61-186337).

SUMMARY (1) Reduction of coloring has been recently demanded for secondary alcohol alkoxylates, for example, for addition of high value.

Thus, a first part of the present invention has been designed in view of such a circumstance, and an object of the present invention is to provide a means that can reduce coloring of secondary alcohol alkoxylate.

To solve the problem, the present inventors have diligently studied, to find that the problem can be solved by mixing a reaction solution containing an alkylene oxide adduct with water and then leaving the reaction solution to stand at a specific temperature to perform separation into an aqueous layer and an organic layer to obtain a solution containing a secondary alcohol alkoxylate having a small number of moles of alkylene oxide added, and purifying the solution; thus, the present invention has been completed.

Specifically, the above object can be achieved with a process for producing a secondary alcohol alkoxylate, the method including: reacting a secondary alcohol with an alkylene oxide in the presence of a catalyst to obtain a reaction solution containing an alkylene oxide adduct; mixing the reaction solution with water and then leaving the reaction solution to stand at a temperature higher than 60° C. to separate into an aqueous layer and an organic layer and to obtain a solution containing a secondary alcohol alkoxylate precursor represented by the Formula (1): $C_mH_{2m+1}[O(XO)_n H]$, wherein X represents an alkylene group having one to three carbon atoms, m is 11 to 15, and n is more than 0 and less than 2.1; and purifying the solution to obtain a secondary alcohol alkoxylate represented by the Formula (2): $C_mH_{2m+1}[O(XO)_p H]$, wherein X and m have the same definitions as those in the Formula (1), and p is 2.5 to 3.5.

By the first part of the present invention, coloring of secondary alcohol alkoxylate can be decreased.

(2) In addition, a technique for mass production of secondary alcohol alkoxylate with less coloring has been recently demanded, for example, for addition of high value.

Thus, a second part of the present invention has been designed in view of such a circumstance, and an object of the present invention is to provide a means for mass production of secondary alcohol alkoxylate with less coloring.

To solve the above problem, the present inventors have diligently studied, to find that the problem can be solved by feeding an alkylene oxide from a plurality of positions in a tubular reactor (reaction tube) to a secondary alcohol to react the secondary alcohol and the alkylene oxide, wherein the alkylene oxide is fed in such a manner that a feeding interval is extended and a feeding rate is increased each with a specific proportion; thus, the present invention has been completed.

Specifically, the above object can be achieved with a process for producing a secondary alcohol alkoxylate, the method including adding an alkylene oxide to a secondary alcohol alkoxylate precursor via an inlet and alkylene oxide feeders installed at n positions, except the inlet, in a tubular reactor, wherein n is an integer of 2 or more, to react the secondary alcohol alkoxylate precursor with the alkylene oxide in the tubular reactor, wherein the alkylene oxide feeders are provided in the tubular reactor so as to satisfy the Expression (i) below, and the alkylene oxide is added to the secondary alcohol alkoxylate precursor so as to satisfy the Expression (ii) below:

[Expression (i)]

$$N[X_{n'}, X_{n'+1}]/(n-1) > 0.4 \quad \text{(i)}$$

wherein $N[X_{n'}, X_{n'+1}]$ denotes the number of sets of three adjacent alkylene oxide feeders satisfying $X_{n'} < X_{n'+1}$, wherein $X_{n'}$ denotes an interval (m) between an alkylene oxide feeder $P_{n'}$ at the n'th position counted from the inlet of the tubular reactor and an alkylene oxide feeder $P_{n'+1}$ at the (n'+1)th position counted from the inlet of the tubular reactor, wherein n' is an integer of 0 or more and n−2 or less, and $X_{n'+1}$ denotes an interval (m) between the alkylene oxide feeder $P_{n'+1}$ and an alkylene oxide feeder $P_{n'+2}$ at the (n'+2)th position counted from the inlet of the tubular reactor; and

[Expression (ii)]

$$N[Y_{n''}, Y_{n''+1}]/n \geq 0.3 \quad \text{(ii)}$$

wherein $N[Y_{n''}, Y_{n''+1}]$ denotes the number of sets of two adjacent alkylene oxide feeders satisfying $Y_{n''} < Y_{n''+1}$, wherein $Y_{n''}$ denotes a feeding rate (kg/hr) of alkylene oxide at an alkylene oxide feeder $P_{n''}$ at the n''th position counted from the inlet of the tubular reactor, wherein n'' is an integer of 0 or more and n−1 or less, and $Y_{n''+1}$ denotes a feeding rate (kg/hr) of alkylene oxide at an alkylene oxide feeder $P_{n''+1}$ at the (n''+1)th position counted from the inlet of the tubular reactor.

By the second part of the present invention, secondary alcohol alkoxylate with reduced coloring can be mass-produced.

DETAILED DESCRIPTION OF EMBODIMENTS

Figure 1:
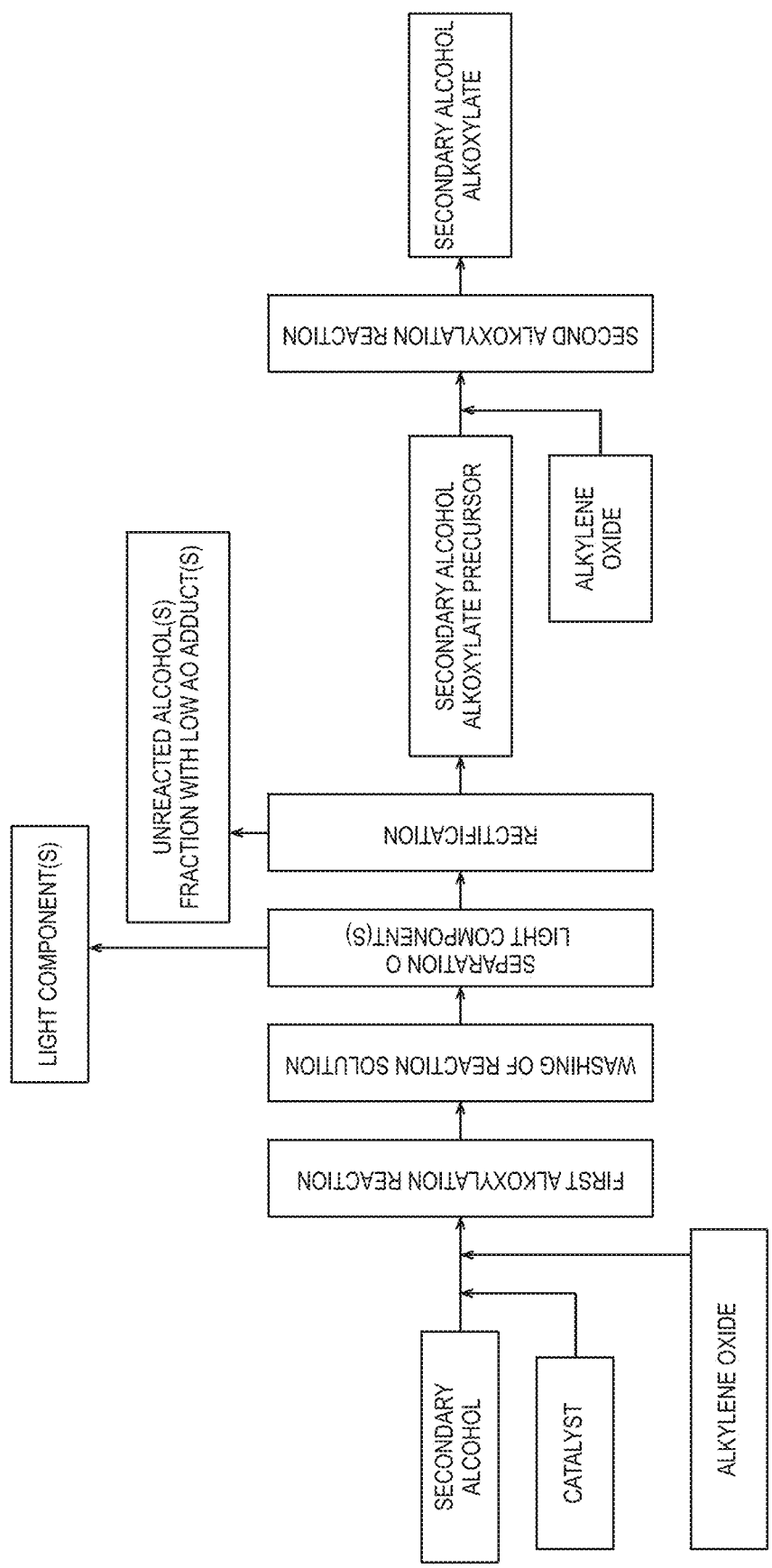
FIG. 1 is a schematic diagram illustrating an embodiment of a production process of the first part of the present invention.

Now, an embodiment(s) of the first part of the present invention will be described. "The first part of the present invention" is occasionally referred to as "the present invention", simply. The present invention is not limited only to the embodiment(s) shown below.

Herein, "X to Y", which shows a range, means "X or more and Y or less", with X and Y included. Unless otherwise specified, operation, measurement of physical properties, and so on are performed at room temperature (20 to 25° C.) and relative humidity of 40 to 50% RH.

<Method for Producing Secondary Alcohol Alkoxylate>

The present invention is to provide a process for producing a secondary alcohol alkoxylate, the method including: i) reacting a secondary alcohol with an alkylene oxide in the presence of a catalyst to obtain a reaction solution containing an alkylene oxide adduct (step (i)); ii) mixing the reaction solution with water and then leaving the reaction solution to stand at a temperature higher than 60° C. to perform separation into an aqueous layer and an organic layer and to obtain a solution containing a secondary alcohol alkoxylate precursor represented by the Formula (1): $C_mH_{2m+1}[O(XO)_nH]$, wherein X represents an alkylene group having one to three carbon atoms, m is 11 to 15, and n is more than 0 and less than 2.1 (step (ii)); and iii) purifying the solution containing the secondary alcohol alkoxylate precursor to obtain a secondary alcohol alkoxylate represented by the Formula (2): $C_mH_{2m+1}[O(XO)_pH]$, wherein X and m are as defined in the Formula (1), and p is 2.5 to 3.5 (step (iii)) (first aspect).

The present inventors have diligently studied for reduced coloring of secondary alcohol alkoxylate. As a result, they have considered that the cause of coloring was the number of moles of alkylene oxide added and the separation conditions when removing impurities by the alkylene oxide addition reaction. Specifically, in the reaction between secondary alcohol and ethylene oxide in the presence of a catalyst (in particular, an acid catalyst), for example, the catalyst (in particular, an acid catalyst) and also reaction byproducts such as polyethylene glycol and dioxane (occasionally referred to as "coloring inducer(s)", collectively) serve as a cause for the coloring. The coloring inducer(s) migrates into an aqueous layer when an alkylene oxide adduct is mixed with water, which can be removable by separation from an organic layer containing the alkylene oxide adduct. In some cases, however, coloring inducer(s) cannot be efficiently separated even when an alkylene oxide adduct is mixed with water. Additional study has been carried out in view of the problem led to the expectation that control of (a) the number of moles of added alkylene oxide (hereinafter, also referred to as "the number of moles of added AO") and (b) the temperature in standing for separating an organic layer and an aqueous layer is effective for reduction of coloring (efficient removal of coloring inducer(s)). With respect to (a), the present inventors have expected that an alkylene oxide adduct with a large number of moles of added AO (hereinafter, also referred to as a high alkylene oxide adduct of secondary alcohol), when being mixed with water, generates micelles to form an emulsified layer between an aqueous layer and an organic layer, and the aqueous layer is not successfully separated, which leads to insufficient removal of coloring inducer(s) present in the aqueous layer. Therefore, additional diligent study has been made on the relationship between the number of moles of added AO in an alkylene oxide adduct and an emulsified layer, to find that controlling the number of moles of added alkylene oxide in an alkylene oxide adduct to be purified (secondary alcohol alkoxylate precursor) to lower than 2.1 can reduce a proportion of an alkylene oxide adduct with a large number of added moles, which is a cause for the formation of an emulsified layer, allowing an aqueous layer and an organic layer to be satisfactorily separated from each other, and thereby coloring inducer(s) can be efficiently removed. With respect to (b), the present inventors expected as follows: an alkylene oxide adduct to be purified (secondary alcohol alkoxylate precursor) is dissolved in water by intermolecular hydrogen bond between its alkylene oxide moiety and water. By controlling a temperature for standing to higher than 60° C. in separating an organic layer and an aqueous layer from each other by leaving the alkylene oxide adduct and water to stand after mixing, thermal motion increases to cleave intermolecular hydrogen bond between the alkylene oxide and water, to lower solubility of the alkylene oxide adduct in water. By this, an aqueous layer and an organic layer can be satisfactorily separated from each other, and coloring inducer(s) can be efficiently removed. Also, to remove an acid catalyst used for production of secondary alcohol alkoxylate such as secondary alcohol ethoxylate, a mixed solution of water and a base (in particular, sodium hydroxide, potassium hydroxide) (alkaline aqueous solution) is used for washing (step of alkaline washing). Insufficient water-washing treatment after the step of alkaline washing may cause the precipitation of minute crystals of sodium fluoride (NaF), sodium borohydride (e.g., $NaH_2BO_3$, $NaHBO_3$), or the like in the subsequent step of dehydration treatment. However, suppression of the formation of an emulsified layer as described above allows efficient removal of such crystals, and thus enables stabilization and/or improvement of quality of a final product.

The mechanism of the exhibition of the above operation and effect by the configuration of the present invention is on the basis of expectation, and the present invention is not limited to the above expectations.

Now, each step of the first aspect will be described with reference to drawings. It should be noted that the following description shows an example of each step of the first aspect, and the present invention is not limited to the followings.

(Step (i))

In the present step, a secondary alcohol is reacted with an alkylene oxide in the presence of a catalyst to obtain a reaction solution containing an alkylene oxide adduct ("FIRST ALKOXYLATION REACTION" in FIG. 1).

The secondary alcohol, which is a raw material in the alkylene oxide addition reaction, is a mixture of secondary alcohols in each of which a hydroxy group is bonding to a nonterminal carbon atom of a saturated aliphatic hydrocarbon having 11 to 15 carbon atoms (normal paraffin), as represented by the following Formula (3):

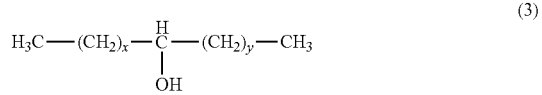

(3)

In the Formula (3), the total of x and y (x+y) is an integer of 8 to 12.

The secondary alcohol is a mixture containing secondary alcohols in each of which a hydroxy group is bonding to a nonterminal carbon atom of a saturated aliphatic hydrocarbon having 11 to 15 carbon atoms (secondary alcohols represented by the Formula (3), wherein x+y is an integer of 8 to 12) (hereinafter, also referred to as "secondary alcohol", simply) as a main component, and preferably a mixture containing secondary alcohols in each of which a hydroxy group is bonding to a nonterminal carbon atom of a saturated aliphatic hydrocarbon having 12 to 14 carbon atoms (secondary alcohol represented by the Formula (3), wherein x+y is an integer of 9 to 11) as a main component. Here, "containing secondary alcohol as a main component" means containing more than 90% by mass (preferably more than 95% by mass) (upper limit: 100% by mass) of secondary alcohol each having a specific number of carbon atoms. An average molecular weight of the secondary alcohol is 158 or higher and 228 or lower, and preferably 186 or higher and 214 or lower. The secondary alcohol may be synthesized, or be a commercially available product.

In a mode of the present invention, a known method such as Japanese Patent Laid-Open No. S48-34807, Japanese Patent Laid-Open No. S56-131531, and Japanese Patent Publication No. S48-37242 can be applied, as it is or with an appropriate modification, as a method for producing the mixture of secondary alcohols represented by the Formula (3). For example, the secondary alcohol can be obtained as follows: a saturated aliphatic hydrocarbon is subjected to liquid-phase oxidation with a gas containing molecular oxygen in the presence of metaboric acid to obtain a reaction solution containing an oxide(s); the oxide(s) is esterified to obtain a reaction solution containing borate compound(s); the reaction solution containing the borate compound(s) is distilled to separate into unreacted saturated aliphatic hydrocarbon(s) and a distillation residue; the distillation residue is hydrolyzed to separate into orthoboric acid and an organic layer; the organic layer is saponified with an alkali to separate into an alkaline aqueous solution layer and a crude alcohol layer; and the crude alcohol layer is further purified.

In a mode of the present invention, a known method such as Japanese Patent Laid-Open No. 2003-221593, Japanese Patent Laid-Open No. S48-34807, Japanese Patent Laid-Open No. S56-131531, Journal of Japan Oil Chemist's Society, 24, 7, p.p. 427-434 (1975), and Japanese Patent Publication No. S51-046084 can be applied, as it is or with an appropriate modification, for alkylene oxide addition reaction. An example of the alkylene oxide addition reaction is shown below. The present invention is not limited by the following method.

For the catalyst, an acid catalyst is used because the number of moles of added alkylene oxide can be controlled to a low degree. Thus, in a preferred mode of the present invention, the catalyst is an acid catalyst. Examples of the acid catalyst include, but are not limited to, boron trifluoride, boron trifluoride complexes (e.g., ether complex (etherate), phenol complex (phenolate), acetate complex), antimony pentachloride, tin tetrachloride, tris(pentafluorophenyl)borane, phosphoric acid, and sulfuric acid. An amount of the catalyst added is, for example, 0.05 to 0.5% by mass, and preferably more than 0.05% by mass and less than 0.3% by mass, relative to the secondary alcohol, but is not limited thereto.

Preferred as the alkylene oxide (AO) are, for example, ethylene oxide and propylene oxide. In a mode of the present invention, the alkylene oxide may have been subjected to replacement by nitrogen gas before adding the alkylene oxide. An initial nitrogen pressure in replacement by nitrogen gas is preferably 0.05 to 1.0 MPa, and more preferably 0.05 to 0.4 MPa.

A feeding rate of the alkylene oxide can be appropriately adjusted so as to obtain the average number of moles of the alkylene oxide added to the secondary alcohol of less than 2.1. For example, an amount of the alkylene oxide added is 1.0 mol or more and less than 1.8 mol, preferably more than 1.0 mol and 1.7 mol or less, more preferably more than 1.1 and less than 1.5 mol, per mole of the secondary alcohol (one hydroxy group of the secondary alcohol), but is not limited thereto. In adding the alkylene oxide in divided portions, the amount of the alkylene oxide is a total amount of the alkylene oxide.

The reaction between the secondary alcohol and the alkylene oxide may be performed, for example, in any of the following manners: the secondary alcohol and the catalyst are fed to a reactor, and the alkylene oxide is then fed to the reactor; the secondary alcohol is fed to a reactor, and the catalyst and the alkylene oxide are then fed to the reactor in any order or simultaneously; and the secondary alcohol, the alkylene oxide, and the catalyst are fed to a reactor. Preferably, the secondary alcohol and the catalyst are fed to a reactor, and the alkylene oxide is then fed thereto. Each of the secondary alcohol, the catalyst, and the alkylene oxide may be fed at once, or fed continuously, or fed in a stepwise manner (in divided portions). Preferably, the secondary alcohol and the catalyst are fed to a reactor at once, and the alkylene oxide is fed to the reactor in a stepwise manner (in divided portions). Thereby, the number of moles of added alkylene oxide (n in the Formula (1)) can be controlled within a desired range with more ease.

The reactor to be used for the reaction between the secondary alcohol and the alkylene oxide may be any of tank reactors (batch reactors), tubular reactors (continuous reactors), and continuous tank reactors. These reactors may be combined as appropriate. A tubular reactor (continuous reactor) is preferably used because the alkylene oxide can be fed in divided portions to the reactor with ease. That is, in a preferred embodiment of the present invention, the reaction between the secondary alcohol and the alkylene oxide is performed in a tubular reactor (continuous reactor), and the alkylene oxide is added from at least one position except the inlet of the tubular reactor (i.e., the alkylene oxide is fed in divided portions). Thereby, the number of moles of added alkylene oxide (n in the Formula (1)) can be controlled within a desired range with more ease. In addition, the configuration can reduce temperature variation in the reactor, inhibiting or preventing local temperature increase caused by ethylene oxide addition reaction. More preferably, a tubular reactor and a tank reactor are is used in combination, and the tank reactor is particularly preferably provided downstream of the tubular reactor (a reactant in the tubular reactor is supplied to the tank reactor). The configuration can more effectively inhibit or prevent local temperature increase caused by alkylene oxide addition reaction, and at the same time, can control the number of moles of added alkylene oxide (n in the Formula (1)) with further more ease.

Figure 3:
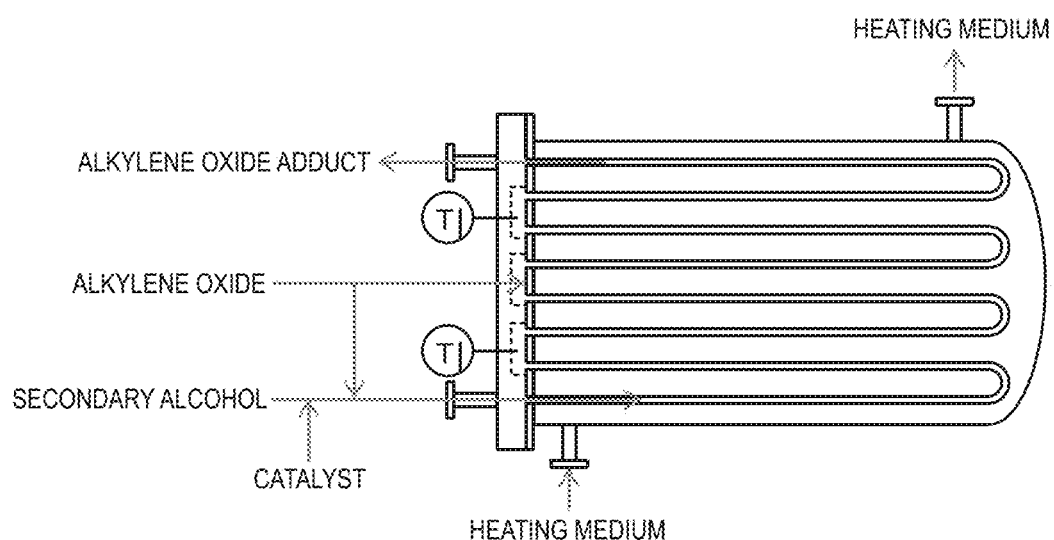
FIG. 3 is a diagram illustrating an example of a reactor for reacting a secondary alcohol and an alkylene oxide in the first part of the present invention.

The shape/size of the reactor is not limited, and any shape/size can be appropriately selected according to feeding rates of raw materials (secondary alcohol, alkylene oxide, catalyst) and so on. In the case of a tubular reactor, for example, the reactor (reaction tube) may be linear, or have a bent part (e.g., J shape, U shape, Z shape), or be circular. The tubular reactor (reaction tube) preferably at least has a bent part(s), and more preferably has a structure in which U-shaped reaction tubes are alternately and repeatedly connected as shown in FIG. 3.

The alkylene oxide may be fed to a plurality of positions of a reactor, and the alkylene oxide is preferably fed to a plurality of positions of a tubular reactor. In the case that a plurality of alkylene oxide feeders is installed in a reactor (in particular, a tubular reactor), it is preferable that an alkylene oxide feeding rate at each feeder be such an amount that a reaction temperature does not increase locally, or such an amount that a reaction temperature is controlled within a preferred range shown below. Alternatively, a place for feeding the alkylene oxide is preferably at a position where a concentration of the alkylene oxide has been lowered by the reaction of the alkylene oxide fed in the previous stage (in the upstream), but are not limited thereto. The reduction of hue can be effectively inhibited by feeding the alkylene oxide in divided portions, as described above, to control the reaction temperature within a proper range (in particular, 70° C. or lower).

Further, a thermometer ("TI" in FIG. 3) may be installed only at one position in the tubular reactor; however, it is preferable for capturing a peak temperature in the reactor that a plurality of thermometers be installed in the reactor. With this configuration, temperature variation during the reaction can be thoroughly checked. Here, the number of thermometers installed is preferably equal to or larger than the number of positions to feed the alkylene oxide to the reactor, which enables capture of peak temperature in the reactor, and the number of thermometers installed is, for example, 5 or more and 50 or less, and preferably 7 or more and 15 or less per 100 m of the length of the tubular reactor, but is not limited thereto. An interval to installed thermometers is preferably such an interval that each thermometer is installed at a position that is immediately after a place to feed the alkylene oxide to the reactor (e.g., in the range of 0 m or more and less than 100 m from a place to feed the alkylene oxide, preferably within 0 to 80 m therefrom, more preferably within 0 to 50 m therefrom for 80% or more of all the thermometers installed) and allows capture of peak temperature resulting from temperature increase by the reaction, and the interval is 1 m or longer and 50 m or shorter, and preferably 5 m or longer and 10 m or shorter, but is not limited thereto. With the installation of thermometers as described, the reaction temperature can be controlled within a proper range (in particular, 70° C. or lower) to effectively inhibit the reduction of hue.

Known conditions can be employed as reaction conditions for the secondary alcohol and the alkylene oxide (conditions for alkoxylation reaction). For example, a reaction temperature is 30° C. or higher and 70° C. or lower, and preferably 45° C. or higher and 70° C. or lower, but is not limited thereto. To adjust to the reaction temperature presented, a system to flow heating medium (e.g., warm water) may be provided to a reactor as shown in FIG. 3. It is preferable to monitor all the thermometers installed to check whether the reaction temperature in the tubular reactor exceeds peak temperature. A reaction time is 30 minutes or longer and 150 minutes or shorter, and preferably 50 minutes or longer and 120 minutes or shorter, but is not limited thereto. Under such conditions, the number of moles of added alkylene oxide in the secondary alcohol alkoxylate precursor (n in the Formula (1)) can be controlled to be less than 2.1 with more ease in the subsequent step (ii). In addition, generation of coloring inducer(s) as byproducts can be effectively inhibited/prevented. In the case that two or more reactors are used, the reaction time presented above is total reaction time. Alternatively, once the number of added alkylene oxide in the alkylene oxide adduct during the reaction has reached a desired value, as determined by measurement, the reaction may be terminated. A reaction pressure may be normal pressure or increased pressure; however, it is preferable to perform the reaction under increased pressure with inert gas such as nitrogen gas, for example, from the viewpoints of the solubility and reaction rate of the alkylene oxide.

Through the reaction, an alkylene oxide adduct (a reaction solution containing an alkylene oxide adduct) can be obtained. In a step of washing in step (ii) shown below, the alkylene oxide addition reaction does not substantially proceed. For this reason, if washing is performed alone in the step of washing in step (ii), the number of moles of added alkylene oxide in the alkylene oxide adduct obtained in the present step is substantially identical to the number of moles of added alkylene oxide in a secondary alcohol alkoxylate precursor represented by the Formula (1) presented below (n in the Formula (1)). In some embodiments of the present invention, the number of moles of added alkylene oxide in the alkylene oxide adduct obtained in the present step is 1.0 mol or more and less than 1.8 mol, preferably more than 1.0 mol and 1.7 mol or less, and more preferably more than 1.1 mol and less than 1.5 mol.

(Step (ii))

In the present step, the reaction solution containing the alkylene oxide adduct (hereinafter, also referred to as "reaction solution", simply), which has been obtained in the step (i) above, is mixed with water, and then left to stand at a temperature higher than 60° C. to perform separation into an aqueous layer and an organic layer and to obtain a solution containing a secondary alcohol alkoxylate precursor represented by the Formula (1): $C_mH_{2m+1}[O(XO)_nH]$ ("WASHING OF REACTION SOLUTION" in FIG. 1). The formation of an emulsified layer between an aqueous layer and an organic layer can be satisfactorily inhibited or prevented by controlling the number of moles of added alkylene oxide (average number of added moles) to less than 2.1; thus, the aqueous layer and the organic layer can be satisfactorily separated from each other. Here, the catalyst (in particular, an acid catalyst), as a cause for the coloring, and also reaction byproducts such as polyethylene glycol and dioxane (coloring inducer(s)) migrate into the aqueous layer. Accordingly, the aqueous layer containing coloring inducer(s) can be efficiently separated from the organic layer (coloring inducer(s) can be efficiently removed) through the present step. If the number of moles of added alkylene oxide (n in the Formula (1)) is 2.1 or more, on the other hand, foaming occurs in mixing with water to form an emulsified layer between an aqueous layer and an organic layer, and the aqueous layer and the organic layer cannot be successfully separated from each other. As a result, coloring inducer(s) contained in the aqueous layer cannot be removed, and the final product (secondary alcohol alkoxylate) is provided with lowered hue (Comparative Example 1 presented later).

In the Formula (1), X represents an alkylene group having one to three carbon atoms. Here, the alkylene group having one to three carbon atoms is a methylene group (—$CH_2$—), an ethylene group (—$CH_2CH_2$—), a trimethylene group (—$CH_2CH_2CH_2$—), or a propylene group (—$CH(CH_3)CH_2$—, —$CH_2CH(CH_3)$—). X is preferably an ethylene group. m is the number of carbon atoms in the secondary alcohol alkoxylate precursor. m is 11 to 15, and preferably 12 to 14. n is the average number of moles of added alkylene oxide in the alkylene oxide adduct. n is more than 0 and less than 2.1, preferably less than 2.0, more preferably less than 1.8, and particularly preferably less than 1.7. Here, if n is 2.1 or more, micelles are generated in mixing with water in step (ii) and an emulsified layer is formed between an aqueous layer and an organic layer, complicating separation of the aqueous layer and the organic layer from each other; as a result, coloring inducer(s) (e.g., the catalyst, reaction byproducts such as polyethylene glycol and dioxane) cannot be sufficiently removed. The lower limit of n is more than 0, but preferably 1.2 or more and more preferably more than 1.5, for an improved yield of a target product (in particular, a secondary alcohol alkoxylate as a 3-mol adduct (3-moles alkylene oxide adduct of secondary alcohol)). Thus, in a preferred mode of the present invention, n in the Formula (1) is 1.2 or more and less than 2.0. In a more preferred mode of the present invention, n in the Formula (1) is more than 1.5 and less than 1.8. In a particularly preferred mode of the present invention, n in the Formula (1) is more than 1.5 and less than 1.7. Herein, a value determined by the following method is employed as the average number of moles of added alkylene oxide.

(Average Number of Moles of Added Alkylene Oxide in Alkylene Oxide Adduct)

The average number of moles of added alkylene oxide (average number of moles of added AO) in an alkylene oxide adduct is calculated from an analytical value for a hydroxyl value of the alkylene oxide adduct by using the Calculation Formula 1 presented below. The hydroxyl value is determined on the basis of Method B in JIS K1557-1: 2007. Specifically, a sample is prepared as a pyridine solution containing phthalic anhydride, and a hydroxy group(s) is phthalated under reflux in pyridine. An excessive portion of the phthalation reagent is hydrolyzed with water, and phthalic acid generated is titrated with sodium hydroxide standard solution. The hydroxyl value is determined by calculating the difference between a titration value in a blank test and that in the test on the sample.

$$\text{Average number of moles of added } AO = \frac{\left(\frac{56.11 \times 1000}{HV} - MW_A\right)}{44.05} \quad \text{Calculation Formula 1}$$

In the Calculation Formula 1, HV denotes an analytical value for hydroxyl value of alkylene oxide adduct; and $MW_A$ denotes an average molecular weight of secondary alcohol mixture.

The alkylene oxide adduct may be mixed with water alone, or mixed with a solution containing water (hereinafter, also referred to as "washing water"). In the case that washing water is used, the washing water contains, in addition to water, a base such as sodium hydroxide, potassium hydroxide, sodium carbonate, potassium carbonate, and lithium hydroxide, and magnesium hydroxide or the like, though the washing water is not limited thereto. The washing water is preferably a mixed solution of water and a base (in particular, sodium hydroxide, potassium hydroxide) (alkaline aqueous solution). A content of a component such as the base or the like is an amount corresponding to a concentration, for example, of 0.1 to 30% by mass, preferably of 0.5 to 5% by mass, but is not limited thereto. Thereby, a catalyst (in particular, an acid catalyst) can be efficiently removed. A step of mixing for the alkylene oxide adduct and water or washing water may be performed once, or repeated twice or more times. In the latter case, it is preferable that the alkylene oxide adduct be mixed with the washing water to separate into an aqueous layer and an organic layer (organic layer 1), and the organic layer 1 be then mixed with water alone to separate into an aqueous layer and an organic layer (organic layer 2). Thus, in a preferred mode of the present invention, the separation is performed by mixing the reaction solution containing the alkylene oxide adduct with an alkaline aqueous solution to separate into an aqueous layer and an organic layer 1, and then mixing the organic layer 1 with water to separate into an aqueous layer and an organic layer 2. Thereby, coloring inducer(s) can be more efficiently removed.

A mixing ratio between the alkylene oxide adduct and water or washing water (in particular, an alkaline aqueous solution) (reaction solution containing alkylene oxide adduct:water or washing water (mixing ratio by volume)) is preferably 1:1 to 8:1, and more preferably 3:1 to 5:1, but is not limited thereto. Thus, in a preferred mode of the present invention, in mixing the reaction solution containing the alkylene oxide adduct with an alkaline aqueous solution, a mixing ratio by volume between the reaction solution and the alkaline aqueous solution is 1:1 to 8:1. In a preferred mode of the present invention, in mixing the organic layer 1 with water, a mixing ratio by volume between the organic layer 1 and the water is 1:1 to 8:1. In a more preferred mode of the present invention, in mixing the reaction solution containing the alkylene oxide adduct and an alkaline aqueous solution, the mixing ratio by volume between the reaction solution and the alkaline aqueous solution is 3:1 to 5:1. In a more preferred mode of the present invention, in mixing the organic layer 1 with water, the mixing ratio by volume between the organic layer 1 and the water is 3:1 to 5:1. With reduced use of water or washing water in an amount equal to or smaller than (in particular, much smaller than) the amount of the solution containing the alkylene oxide adduct (the reaction solution or the organic layer 1), the emulsified state (in particular, water-in-oil emulsion) (accordingly, coloring) in mixing the reaction solution with water or washing water can be more effectively inhibited or prevented, with ensuring washing efficiency.

A method for mixing the alkylene oxide adduct and the water or washing water is not limited, and a known method can be used. Examples thereof include a method which comprises adding water or washing water to the alkylene oxide adduct, and sufficiently stirring and mixing the resultant mixture to dissolve the alkylene oxide adduct in an organic layer and then left to stand, and, after an aqueous layer and an organic layer are separated from each other, the organic layer is taken out. The stirring/mixing conditions in this case are not limited. For example, a stirring/mixing temperature is 40 to 100° C., and preferably 80° C. or higher and lower than 100° C. A stirring/mixing time is 5 to 120 minutes, and preferably 10 minutes or longer and shorter than 30 minutes. In the case that the alkylene oxide adduct is washed with water and washing water (washed with water and then with washing water, or washed with washing water and then with water), identical or different stirring/mixing conditions may be used for the steps of washing.

After being mixed with water or washing water, the reaction solution is left to stand at a temperature higher than 60° C. to separate into an aqueous layer and an organic layer. If the temperature for standing is 60° C. or lower, an emulsified layer is formed between the aqueous layer and the organic layer, and the aqueous layer cannot be successfully separated. As a result, coloring inducer(s) contained in the aqueous layer cannot be removed, and the final product (secondary alcohol alkoxylate) is provided with lowered hue (Comparative Example 2 presented later). The temperature for standing is preferably higher than 60° C. and lower than 100° C., more preferably higher than 60° C. and 95° C. or lower, and particularly preferably higher than 65° C. and lower than 85° C. A time for standing is, for example, 5 to 120 minutes, and preferably 30 to 60 minutes, but is not limited thereto. In the case that the alkylene oxide adduct is washed with water and washing water (washed with water and then with washing water, or washed with washing water and then with water), identical or different temperatures for standing may be used for the steps of washing; however, the temperatures for standing are both higher than 60° C. Thus, in a preferred mode of the present invention, the separation is performed by mixing the reaction solution containing the alkylene oxide adduct with an alkaline aqueous solution and leaving the resultant mixture to stand at a temperature higher than 60° C. to separate into an aqueous layer and an organic layer 1, and then mixing the organic layer 1 with water and leaving the resultant mixture to stand at a temperature higher than 60° C. to separate into an aqueous layer and an organic layer 2. Likewise, in the case that the alkylene oxide adduct is washed with water and washing water (washed with water and then with washing water, or washed with washing water and then with water), identical or different times for standing may be used for the steps of washing.

Figure 2:
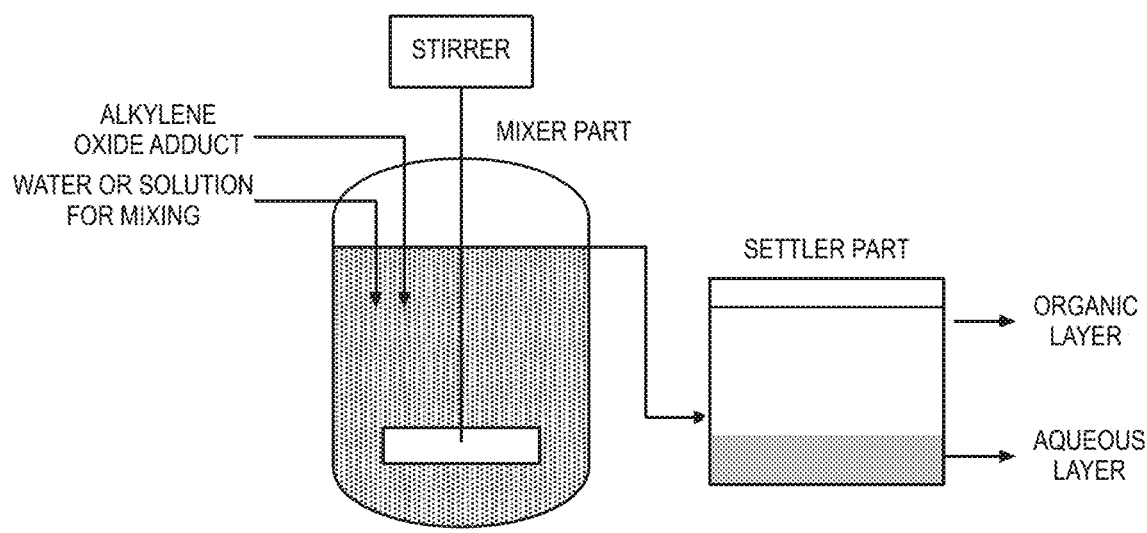
FIG. 2 is a diagram illustrating a mixer/settler-type apparatus for mixing an alkylene oxide adduct with water to separate into an aqueous layer and an organic layer in the first part of the present invention.

An apparatus to be used for mixing the alkylene oxide adduct and water or washing water may be, but is not limited to, a mixer/settler-type apparatus capable of stirring/mixing the alkylene oxide adduct and water or a solution for mixing (washing water) in a mixer part (mixing tank) and then separating an aqueous layer and an organic layer from each other in a settler part (settling tank), as illustrated in FIG. 2. Alternatively, an apparatus like a line mixer or a counter-current washing column may be used.

The organic layer obtained through the described process may be dehydrated, as necessary. Thereby, the number of moles of added alkylene oxide (n in the Formula (1)) in the secondary alcohol alkoxylate precursor can be more effectively controlled within a desired range. A dehydration method is not limited, and a known method can be applied as it is or with an appropriate modification. For example, the organic layer can be dehydrated by distillation or fractional distillation. A dehydration pressure (column top (top) pressure) is, for example, 1 to 500 hPa, and preferably 50 to 300 hPa, but is not limited thereto. Herein, a pressure indicates a value of pressure measured with a pressure gauge installed in an upper part of a reactor to measure the pressure of a gas phase part. Unless otherwise specified, the same definition is applied throughout the present specification. A dehydration temperature (bottom temperature) is, for example, 50 to 200° C., and preferably 100 to 150° C., but is not limited thereto. Under such conditions, the number of moles of added alkylene oxide (n in the Formula (1)) in the secondary alcohol alkoxylate precursor can be more effectively controlled within a desired range, with unreacted alcohols and so on efficiently removed.

Through the described process, a solution containing a secondary alcohol alkoxylate precursor can be obtained, wherein the solution contains a high purity of a secondary alcohol alkoxylate precursor having a desired number of moles of added alkylene oxide.

(Step (iii))

In the present step, the solution containing the secondary alcohol alkoxylate precursor, which has been separated in step (ii) above, is purified ("SEPARATION OF LIGHT COMPONENT(S)" and "RECTIFICATION" in FIG. 1). Thereby, a secondary alcohol alkoxylate represented by the Formula (2): $C_mH_{2m+1}[O(XO)_pH]$ can be obtained. In the Formula (2), X and m have the same definitions as those in the Formula (1). p is the average number of moles of added alkylene oxide in the secondary alcohol alkoxylate. p is 2.5 or more and 3.5 or less, and preferably more than 2.7 and less than 3.1. Herein, a value determined by the method described for n in the Formula (1) is employed as the average number of moles of added alkylene oxide in the secondary alcohol alkoxylate.

A purification method is not limited, and a known method can be applied as it is or with an appropriate modification. For example, the solution containing the secondary alcohol alkoxylate precursor can be purified by distillation or fractional distillation. A purification pressure (column top (top) pressure) is, for example, 1 to 100 hPa, and preferably 3 to 50 hPa, but is not limited thereto. A purification temperature (bottom temperature) is, for example, 150 to 250° C., and preferably 175 to 225° C., but is not limited thereto. Under such conditions, light component(s), unreacted alcohol(s), secondary alcohol alkoxylate fraction(s) with a small number of moles of added alkylene oxide (e.g., less than 2.5 mol), and so on can be efficiently removed to properly separate a desired secondary alcohol alkoxylate precursor. Although a step of purification (step of distillation/fractional distillation) is performed twice in FIG. 1, the step of purification may be performed once or repeatedly. For example, as illustrated in FIG. 1, it is acceptable that light component(s) is removed through a step of separation of light component(s) ("SEPARATION OF LIGHT COMPONENT(S)" in FIG. 1), and unreacted alcohol(s) and low AO adduct fraction(s) with a small moles of added alkylene oxide (e.g., the number of moles of added alkylene oxide=less than 2.5) are then removed through a rectification step ("RECTIFICATION" in FIG. 1).

Thereby, a secondary alcohol alkoxylate with a high purity (containing a small amount of coloring inducer(s) or no coloring inducer(s)) can be obtained. Thus the secondary alcohol alkoxylate can exhibit satisfactory hue. Specifically, the hue (APHA) of the secondary alcohol alkoxylate is lower than 45. To be specific, the present invention is to provide a secondary alcohol alkoxylate having a hue (APHA) of lower than 45 and represented by the Formula (2): $C_mH_{2m+1}[O(XO)_pH]$, wherein X represents an alkylene group having one to three carbon atoms, m is 12 to 14, and p is 2.5 to 3.5 (second aspect). The hue (APHA) of the secondary alcohol alkoxylate is preferably 40 or lower, and more preferably 30 or lower. Here, the lower limit of the hue (APHA) of the secondary alcohol alkoxylate is not limited, and a hue (APHA) of 20 or higher would be enough. Thus, the hue (APHA) of the secondary alcohol alkoxylate is preferably 20 to 40, and more preferably 20 to 30. Herein, a value determined by a method described later in Examples is employed as the hue (APHA) of the secondary alcohol alkoxylate.

As necessary, an alkylene oxide may be further added to the secondary alcohol alkoxylate obtained through the described process to produce a secondary alcohol alkoxylate with an increased number of moles of AO (high alkylene oxide adduct of secondary alcohol) ("SECOND ALKOXYLATION REACTION" in FIG. 1). Preferably, second alkoxylation reaction is performed by using a tubular reactor under specific conditions as described in detail below. This enables mass production of a high alkylene oxide adduct of secondary alcohol with reduced coloring.

Thus, the present invention additionally provides a method for producing a high alkylene oxide adduct of secondary alcohol, the method including:

producing a secondary alcohol alkoxylate represented by the Formula (2): $C_mH_{2m+1}[O(XO)_pH]$, wherein, X represents an alkylene group having one to three carbon atoms, m is 12 to 14, and p is 2.5 to 3.5, by using the method of the present invention; and adding an alkylene oxide to the secondary alcohol alkoxylate via an inlet and alkylene oxide feeders installed at n positions, except the inlet, in a tubular reactor, wherein n is an integer of 2 or more, to react the secondary alcohol alkoxylate with the alkylene oxide in the tubular reactor to obtain a high alkylene oxide adduct of secondary alcohol represented by the Formula (4): $C_mH_{2m+1}[O(XO)_qH]$, wherein X represents an alkylene group having one to three carbon atoms, m is 12 to 14, and q is more than 3.5 and 50 or less, wherein the alkylene oxide feeders are provided in the tubular reactor so as to satisfy the Expression (i) presented below, and the alkylene oxide is added to the secondary alcohol alkoxylate so as to satisfy the Expression (ii) presented below (third aspect):

$$N[X_{n'},X_{n'+1}]/(n-1) > 0.4 \quad (i)$$

wherein $N[X_{n'},X_{n'+1}]$ denotes the number of sets of three adjacent alkylene oxide feeders satisfying $X_{n'} < X_{n'+1}$, wherein $X_{n'}$ denotes an interval (m) between an alkylene oxide feeder $P_{n'}$ installed at the n'th position counted from the inlet of the tubular reactor and an alkylene oxide feeder $P_{n'+1}$ installed at the (n'+1)th position counted from the inlet of the tubular reactor, wherein n' is an integer between 0 or more and n−2 or less, and $X_{n'+1}$ denotes an interval (m) between the alkylene oxide feeder $P_{n'+1}$ and an alkylene oxide feeder $P_{n'+2}$ installed at the (n'+2)th position counted from the inlet of the tubular reactor; and $$N[Y_{n''},Y_{n''+1}]/n \geq 0.3 \quad (ii)$$

wherein $N[Y_{n''},Y_{n''+1}]$ denotes the number of sets of two adjacent alkylene oxide feeders satisfying $Y_{n''} < Y_{n''+1}$, wherein $Y_{n''}$ denotes a feeding rate (kg/hr) of alkylene oxide at an alkylene oxide feeder $P_{n''}$ installed at the n''th position counted from the inlet of the tubular reactor, wherein n'' is an integer between 0 or more and n−1 or less, and $Y_{n''+1}$ denotes a feeding rate (kg/hr) of alkylene oxide at an alkylene oxide feeder $P_{n''+1}$ installed at the (n''+1)th position counted from the inlet of the tubular reactor.

In the following, the second alkoxylation reaction according to the above preferred mode (third aspect) will be described with reference to drawings. The following description is for illustrating an example of the step of second alkoxylation reaction, and the present invention is not limited to the followings.

In the preferred mode (third aspect), a high alkylene oxide adduct of secondary alcohol having a large number of moles of added alkylene oxide, as a final product, is produced, by feeding the alkylene oxide in divided portions to the secondary alcohol alkoxylate via a plurality of feeders in the tubular reactor (reaction tube) (divided feed), (i) in such a manner that the Expression (i): $N[X_{n'},X_{n'+1}]/(n-1) > 0.4$ is satisfied, in other words, an alkylene oxide feeding interval is extended with a proportion of more than 40%; and (ii) in such a manner that the Expression (ii): $N[Y_{n''},Y_{n''+1}]/n \geq 0.3$ is satisfied, in other words, a feeding rate is increased with a proportion of 30% or more. By the divided feed under such specific conditions, the alkylene oxide addition reaction can be properly controlled, and as a result coloring of a high alkylene oxide adduct of secondary alcohol, as the final product, can be further reduced. The method according to the present mode is a continuous production method. Hence, the method allows mass production of a high alkylene oxide adduct of secondary alcohol with reduced coloring. Accordingly, the above configuration allows mass production of a high alkylene oxide adduct of secondary alcohol with reduced coloring. The mechanism of the exhibition of the above operation and effect by the configuration of the present invention is on the basis of expectation, and the present invention is not limited to the above expectation.

In the preferred mode (third aspect), the tubular reactor has an inlet and alkylene oxide feeders at n positions (n is an integer of 2 or more) except the inlet. The alkylene oxide is added to the secondary alcohol alkoxylate via the alkylene oxide feeders (divided feed) to react the secondary alcohol alkoxylate with the alkylene oxide in the tubular reactor. Herein, an alkylene oxide feeder refers to a feeder through which an alkylene oxide is actually fed. Accordingly, an alkylene oxide feeder that is installed in a tubular reactor to feed an alkylene oxide but, nevertheless, does not feed any alkylene oxide in actual cases is not regarded as an "alkylene oxide feeder".

In the preferred mode (third aspect), in the tubular reactor, the alkylene oxide feeders (including the reactor inlet) are installed in such a manner that the Expression (i) is satisfied. Specifically, in reacting the secondary alcohol and the alkylene oxide, alkylene oxide feeders are provided in such a manner that the feeding interval is extended with the proportion in the Expression (i) being more than 40%.

[Expression (i)]

$$N[X_{n'},X_{n'+1}]/(n-1) > 0.4 \quad (i)$$

In the Expression (i), $N[X_{n'},X_{n'+1}]$ represents the number of sets of three adjacent alkylene oxide feeders satisfying the relationship: $X_{n'} < X_{n'+1}$. Here, $X_{n'}$ represents an interval (m) between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor. n' is an integer of 0 or more and n−2 or less. $X_{n'+1}$ represents an interval (m) between the alkylene oxide feeder $P_{n'+1}$ and an alkylene oxide feeder $P_{n'+2}$ disposed at the (n'+2)th position from the inlet of the tubular reactor. That is, as three adjacent alkylene oxide feeders ($P_{n'}$, $P_{n'+1}$, and $P_{n'+2}$ counted from the tubular reactor inlet) are regarded as one set as illustrated below, $N[X_{n'}$, $X_{n'+1}$] indicates the number of sets of alkylene oxide feeders in which the interval ($X_{n'+1}$) between the two adjacent alkylene oxide feeders ($P_{n'+1}$ and $P_{n'+2}$) in the outlet (reaction downstream) side is larger than the interval ($X_{n'}$) between the two adjacent alkylene oxide feeders ($P_{n'}$ and $P_{n'+1}$) in the inlet (reaction upstream) side ($X_{n'}<X_{n'+1}$).

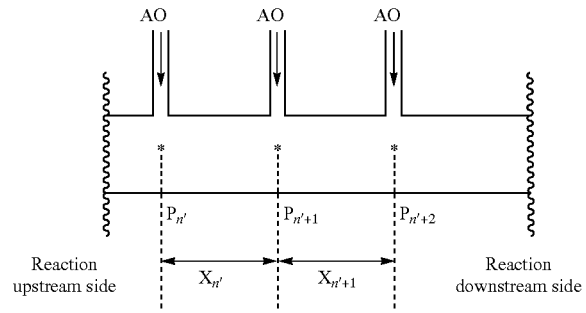

Thus, the Expression (i) means that a proportion of the number of sets of alkylene oxide feeders satisfying the relationship: $X_{n'}<X_{n'+1}$(N[$X_{n'}$,$X_{n'+1}$]) to the total number of sets of alkylene oxide feeders (n−1) (N[$X_{n'}$,$X_{n'+1}$]/(n−1)) is more than 40% (4/10). Herein, the number of sets of alkylene oxide feeders satisfying the relationship: $X_{n'}<X_{n'+1}$(N[$X_{n'}$, $X_{n'+1}$]) is divided by the total number of sets of alkylene oxide feeders (n−1) to give a value with two decimal places, which is rounded off to one decimal place and the resultant is employed as "N[$X_{n'}$,$X_{n'+1}$]/(n−1)".

In the preferred mode (third aspect), the reaction tube refers to a part of the tubular reactor where the reaction of adding the alkylene oxide to the secondary alcohol alkoxylate substantially proceeds. Accordingly, in FIG. 4, for example, the reaction tube part between the tubular reactor inlet ($P_0$ in FIG. 4) and the tubular reactor outlet ($P_{outlet}$ in FIG. 4) is the reaction tube according to the present embodiment.

Figure 4:
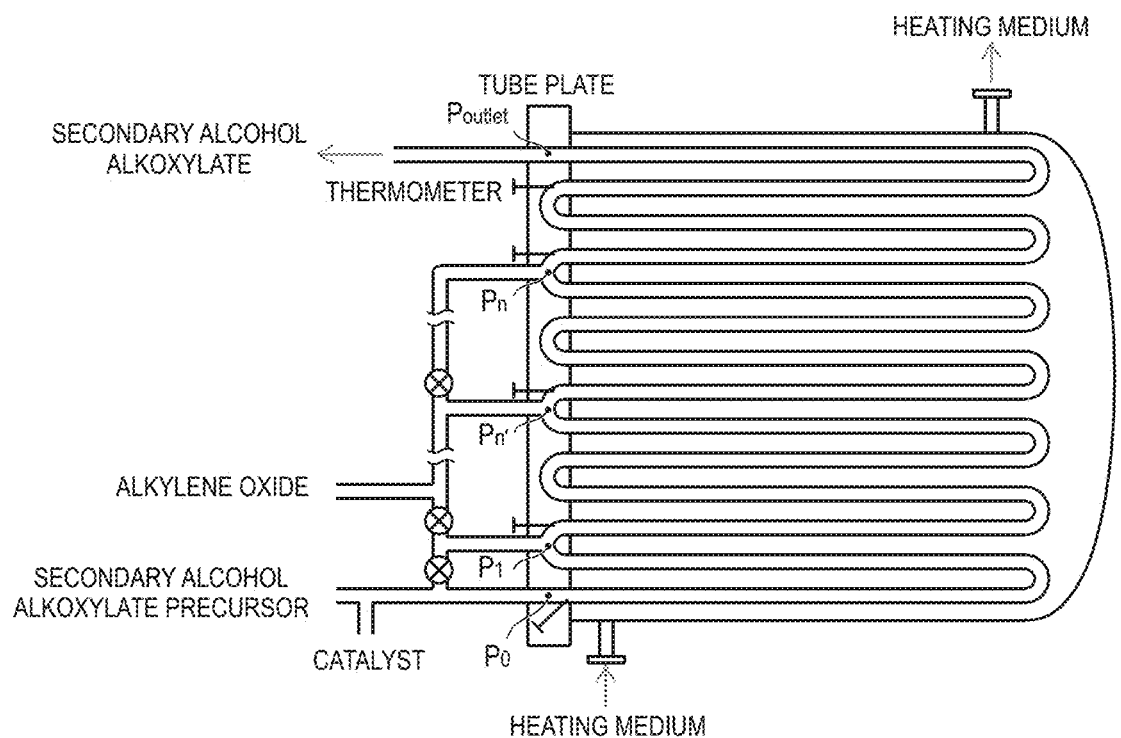
FIG. 4 is a diagram illustrating an example of a tubular reactor that is used for second alkoxylation reaction in the first part of the present invention.

In the preferred mode (third aspect), the alkylene oxide feeder with n' being 0 ($P_{0'}$) is the tubular reactor inlet which is an alkylene oxide feeder disposed at the first position in the reaction tube ("$P_0$" in FIG. 4).

Figure 5:
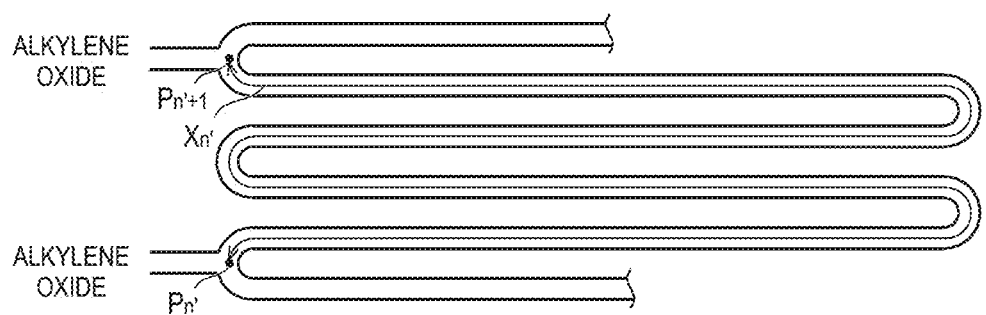
FIG. 5 is a diagram for describing an interval between an alkylene oxide feeder $P_{n'}$ at the n'th position counted from the inlet of the tubular reactor in FIG. 4 and an alkylene oxide feeder $P_{n'+1}$ at the (n'+1)th position counted from the inlet of the tubular reactor, $[X_{n'}(m)]$.

In the preferred mode (third aspect), the interval ($X_{n'}$) between two adjacent alkylene oxide feeders ($P_{n'}$ and $P_{n'+1}$) refers to, as illustrated in FIG. 5, a distance between a center of a reaction tube at the alkylene oxide feeder ($P_{n'}$) to feed the alkylene oxide ("$P_{n'}$" in FIG. 5) and a center of a reaction tube at the adjacent alkylene oxide feeder ($P_{n'+1}$) in the reaction downstream side of the alkylene oxide feeder ($P_{n'}$) (a length of a solid line part "$X_{n'}$" in FIG. 5). Here, the "center of the reaction tube" is a point corresponding to a center of gravity of a section obtained by cutting a tube along a plane perpendicular to the longitudinal direction of the reaction tube. In the case that a cross section of a reaction tube is circular, the center of the reaction tube is a center of the circle; in the case that a cross section of a reaction tube is noncircular, the center of the reaction tube is a center of the largest circle among circles that can be drawn in the cross section of the reaction tube. For example, an interval ($X_{1'}$) between an alkylene oxide feeder ($P_{0'}$) and an alkylene oxide feeder ($P_{1'}$) adjacent to the $P_{0'}$ is a distance between a center of the reaction tube at the reaction tube inlet from which the alkylene oxide is first fed (a center part of the tube plate corresponding to a boundary between the tube plate and the reaction tube) and a center of the reaction tube at the alkylene oxide feeder from which the alkylene oxide is subsequently fed.

If N[$X_{n'}$,$X_{n'+1}$]/(n−1) in the Expression (i) is 0.4 or less, the alkylene oxide is fed too frequently to cause local addition of the alkylene oxide to the secondary alcohol alkoxylate, resulting in the coloring of high alkylene oxide adduct of secondary alcohol as a final product. For improved effects of reducing the coloring of high alkylene oxide adduct of secondary alcohol as a final product, for example, N[$X_{n'}$,$X_{n'+1}$]/(n−1) in the Expression (i) is preferably 0.5 or more, more preferably more than 0.7, and particularly preferably 0.8 or more. With the present mode, the alkylene oxide addition reaction can be properly controlled through inhibiting local addition reaction of the alkylene oxide to the secondary alcohol alkoxylate, and thus the coloring of high alkylene oxide adduct of secondary alcohol as a final product can be more effectively reduced. Since it is preferable that all the sets of alkylene oxide feeders satisfy $X_{n'}<X_{n'+1}$, the upper limit of N[$X_{n'}$,$X_{n'+1}$]/(n−1) in the Expression (i) is preferably 1, but may be, for example, less than 0.95 or 0.9 or less.

In the preferred mode (third aspect), while the alkylene oxide is fed in such a manner that the feeding interval is extended with the proportion in the Expression (i) being more than 40%, the feeding interval for the alkylene oxide is constant or extended ($X_{n'} \le X_{n'+1}$) preferably with the proportion in the Expression (i) being more than 80%, more preferably at all of the sets of alkylene oxide feeders. With this configuration, the coloring of high alkylene oxide adduct of secondary alcohol as a final product can be more effectively reduced.

In the preferred mode (third aspect), if $X_{n'+1}$ is larger than $X_{n'}$ ($X_{n'}<X_{n'+1}$ is satisfied), then a ratio between an interval between an alkylene oxide feeder $P_{n'+1}$ disposed at the (n'+1)th position from the inlet of the tubular reactor and an alkylene oxide feeder $P_{n'+2}$ disposed at the (n'+2)th position from the inlet of the tubular reactor, [$X_{n'+1}$(m)], and an interval between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor, [$X_{n'}$(m)], that is, [$X_{n'+1}/X_{n'}$], is more than 1. For example, for higher effects of reducing the coloring of high alkylene oxide adduct of secondary alcohol as a final product, the ratio between $X_{n'+1}$ and $X_{n'}$, [$X_{n'+1}/X_{n'}$], is preferably more than 1.05, and more preferably 1.10 or more, but is not limited thereto. The ratio of $X_{n'}$ to $X_{n'+1}$, [$X_{n'+1}/X_{n'}$], in that case is, for example, 1.50 or less, and preferably less than 1.30, but is not limited thereto.

In the preferred mode (third aspect), a feeding interval for the alkylene oxide (a distance between adjacent alkylene oxide feeders, "$X_{n'}$" in FIG. 5) is, for example, 10 m or larger and 200 m or smaller, preferably 20 m or larger and 150 m or smaller, and more preferably larger than 30 m and smaller than 100 m, but is not limited thereto. Local addition reaction of the alkylene oxide to the secondary alcohol alkoxylate can be more effectively inhibited or prevented. Therefore, hue of the high alkylene oxide adduct of secondary alcohol as a final product can be improved.

In the preferred mode (third aspect), regarding the number of alkylene oxide feeders disposed in the tubular reactor, the alkylene oxide feeders are installed in such a manner that fewer alkylene oxide feeders are disposed as going to the downstream of the tubular reactor. Preferably, a ratio of the number of alkylene oxide feeders disposed from an inlet to a half point of total tube length of a tubular reactor ($N_{inlet}$)

to the number of alkylene oxide feeders disposed beyond the half point of total tube length to an outlet of the tubular reactor ($N_{outlet}$) ($N_{inlet}/N_{outlet}$) is higher than 1.0/1 and 10.0/1 or lower, and preferably 1.5/1 or higher and lower than 5.0/1. Herein, "$N_{inlet}$" denotes, in a total tube length from an inlet to an outlet of a tubular reactor, the number of alkylene oxide feeders disposed in a region from the inlet to a half point of the total tube length (including the reactor inlet and the half point of the total tube length) (also referred to as the "tubular reactor upstream region"). Thus, if an alkylene oxide feeder is disposed at the tubular reactor inlet, the alkylene oxide feeder disposed at the tubular reactor inlet is included as a constituent of the "$N_{inlet}$". "$N_{outlet}$" denotes, in a total tube length from an inlet to an outlet of a tubular reactor, the number of alkylene oxide feeders disposed in a region beyond the half point of the total tube length to an outlet of the tubular reactor (also referred to as the "tubular reactor downstream region"). For example, in Example 1 shown later, 10 ethylene oxide feeders in total, including a second reactor inlet, are disposed in a second reactor, the number of ethylene oxide feeders disposed from an inlet to a half point of the total tube length in the second reactor (tubular reactor upstream region) is 8 ($N_{inlet}$=8), and the number of ethylene oxide feeders disposed beyond the half point of the total tube length of the tubular reactor to an outlet (tubular reactor downstream region) in the second reactor is 2 ($N_{outlet}$=2), and hence $N_{inlet}/N_{outlet}$ is 4.0 (=8/2).

In the preferred mode (third aspect), the alkylene oxide is added to the secondary alcohol alkoxylate in such a manner that the Expression (ii) presented below is satisfied. In other words, in reacting the secondary alcohol alkoxylate and the alkylene oxide, the alkylene oxide is fed in such a manner that a feeding rate is increased with a proportion of 30% or more:

$$N[Y_{n''}, Y_{n''+1}]/n \geq 0.3 \quad \text{(ii)}$$

In the Expression (ii), $N[Y_{n''}, Y_{n''+1}]$ represents the number of sets of two adjacent alkylene oxide feeders satisfying the relationship: $Y_{n''} < Y_{n''+1}$. Here, $Y_{n''}$ represents a feeding rate (kg/hr) of alkylene oxide at an alkylene oxide feeder $P_{n''}$ disposed at the n"th position from the inlet of the tubular reactor. n" is an integer of 0 or more and n−1 or less. $Y_{n''+1}$ represents a feeding rate (kg/hr) of alkylene oxide at an alkylene oxide feeder $P_{n''+1}$ disposed at the (n"+1)th position from the inlet of the tubular reactor. That is, as two adjacent alkylene oxide feeders ($P_{n''}$ and $P_{n''+1}$ from the inlet) are regarded as one set, $N[Y_{n''}, Y_{n''+1}]$ represents the number of sets of alkylene oxide feeders in which an alkylene oxide feeding rate ($Y_{n''+1}$) at an alkylene oxide feeder ($P_{n''+1}$) in the outlet (reaction downstream) side is higher than an alkylene oxide feeding rate ($Y_{n''}$) at the adjacent alkylene oxide feeder ($P_{n''}$) in the inlet (reaction upstream) side ($Y_{n''} < Y_{n''+1}$).

Thus, the Expression (ii) means that a proportion of the number of sets of alkylene oxide feeders satisfying the relationship: $Y_{n''} < Y_{n''+1}$ ($N[Y_{n''}, Y_{n''+1}]$) to a total number of sets of alkylene oxide feeders (n) is 30% (3/10) or more. Herein, the number of sets of alkylene oxide feeders satisfying the relationship: $Y_{n''} < Y_{n''+1}$ ($N[Y_{n''}, Y_{n''+1}]$) is divided by the total number of sets of alkylene oxide feeders (n) to give a value with two decimal places, which is rounded off to one decimal place and the resultant is employed as "$N[Y_{n''}, Y_{n''+1}]/n$".

In the preferred mode, an alkylene oxide feeder with n" being 0 ($P_{0''}$) is a tubular reactor inlet, which is an alkylene oxide feeder disposed at the first position in a reaction tube ("$P_0$" in FIG. 4).

If $N[Y_{n''}, Y_{n''+1}]/(n-1)$ in the Expression (ii) is less than 0.3, the alkylene oxide addition reaction cannot be properly controlled because of temperature increase in the reactor, resulting in the coloring of high alkylene oxide adduct of secondary alcohol as a final product. For higher effects of reducing the coloring of high alkylene oxide adduct of secondary alcohol as a final product, $N[Y_{n''}, Y_{n''+1}]/(n-1)$ in the Expression (ii) is preferably 0.6 or more, more preferably more than 0.7, and particularly preferably 0.9 or more. The upper limit of $N[Y_{n''}, Y_{n''+1}]/(n-1)$ in the Expression (ii) is preferably 1, but may be, for example, less than 0.97 or 0.95 or less.

In the preferred mode (third aspect), while the alkylene oxide is fed in such a manner that a feeding rate is increased with a proportion in the Expression (ii) being 30% or more, the feeding rate of alkylene oxide is constant or increased ($Y_{n''} \leq Y_{n''+1}$) preferably at more than 80% of, more preferably at 90% or more of the sets of alkylene oxide feeders. With this configuration, the coloring of high alkylene oxide adduct of secondary alcohol as a final product can be more effectively reduced.

In the preferred mode (third aspect), if $Y_{n''+1}$ is larger than $Y_{n''}$ ($Y_{n''} < Y_{n''+1}$), then the difference between an alkylene oxide feeding rate ($Y_{n''}$) at an alkylene oxide feeder ($P_{n''}$) in the inlet (reaction upstream) side and an alkylene oxide feeding rate ($Y_{n''+1}$) at the adjacent alkylene oxide feeder ($P_{n''+1}$) in the outlet (reaction downstream) side ($Y_{n''+1} - Y_{n''}$ (kg/hr)) is more than 0 (kg/hr). For example, for higher effects of reducing the coloring of high alkylene oxide adduct of secondary alcohol as a final product, the difference between $Y_{n''}$ and $Y_{n''+1}$ ($Y_{n''+1} - Y_{n''}$ (kg/hr)) in the case that $Y_{n''+1}$ is larger than $Y_{n''}$ ($Y_{n''} < Y_{n''+1}$) is preferably 0.5 (kg/hr) or more and 60 (kg/hr) or less, and more preferably 1 (kg/hr) or more and less than 40 (kg/hr), but is not limited thereto.

In the preferred mode (third aspect), in the second alkoxylation reaction, the alkylene oxide is added from the inlet of the tubular reactor and at least one position except the inlet to continuously react the secondary alcohol alkoxylate with the alkylene oxide in the tubular reactor under the conditions as described above. With this configuration, local temperature variation in the reactor can be inhibited (in particular, inhibition/prevention of local temperature increase due to the alkylene oxide addition reaction). Therefore, the coloring of high alkylene oxide adduct of secondary alcohol as a final product can be effectively reduced. In addition, the number of moles of added alkylene oxide in high alkylene oxide adduct of secondary alcohol as a final product can be controlled with ease. It is sufficient for the reaction between the secondary alcohol alkoxylate and the alkylene oxide to be performed in a tubular reactor (continuous reactor), and an additional tank reactor (batch reactor), tubular reactor (continuous reactor), or continuous tank reactor may be provided in the upstream or downstream of the tubular reactor.

In a mode of the preferred mode (third aspect), for the alkylene oxide addition reaction, a known method such as Japanese Patent Laid-Open No. 2003-221593, Japanese Patent Laid-Open No. S48-34807, Japanese Patent Laid-Open No. S56-131531, Journal of Japan Oil Chemist's Society, 24, 7, p.p. 427-434 (1975), and Japanese Patent Publication No. S51-046084 can be applied as it is or with an appropriate modification. An example of the alkylene oxide addition reaction will be shown below. The present invention is not limited by the following method.

In the preferred mode (third aspect), an alkaline catalyst is used as a catalyst because a high alkylene oxide adduct of secondary alcohol having a desired number of moles of added alkylene oxide can be produced (the number of moles of added alkylene oxide can be controlled to be large). Thus, in a preferred mode of the present invention, the catalyst is an alkaline catalyst. Examples of the alkaline catalyst include, but are not limited to, sodium hydroxide, potassium hydroxide, and sodium alkoxide. An amount of the catalyst is, for example, 0.01 to 1% by mass, and preferably more than 0.02% by mass and less than 0.5% by mass, relative to the secondary alcohol alkoxylate, but is not limited thereto. Alternatively, a feeding rate of the catalyst to the tubular reactor may be 0.1 to 5 kg/hr, and preferably 0.5 to 2 kg/hr, but is not limited thereto. In the present step, the catalyst may be added as it is or in the form of a solution (e.g., an aqueous solution). In the latter case, a concentration of the catalyst in the catalyst solution is about 30 to 70% by mass, but is not limited thereto.

In the preferred mode (third aspect), preferred as the alkylene oxide (AO) are, for example, ethylene oxide and propylene oxide. In a mode of the present invention, the alkylene oxide may have been subjected to replacement by nitrogen gas in adding the alkylene oxide. An initial nitrogen pressure in replacement by nitrogen gas is preferably 1.0 to 2.0 MPa, and more preferably 1.3 to 1.7 MPa.

In the preferred mode (third aspect), a feeding rate of the alkylene oxide to the tubular reactor is 300 to 1500 kg/hr, and preferably 700 to 1200 kg/hr, but is not limited thereto. Alternatively, a feeding rate of the alkylene oxide to the tubular reactor may be adjusted so that the average number of moles of the alkylene oxide added to the secondary alcohol (the average number of moles of added alkylene oxide in high alkylene oxide adduct of secondary alcohol as a final product) can reach 5 to 50 mol (preferably 6 to 15 mol, more preferably 7 to 9 mol). For example, an amount of the alkylene oxide to be added is, for example, 5 to 15 mol, and preferably 6 to 12 mol per mole of the secondary alcohol alkoxylate, but is not limited thereto. The amount of the alkylene oxide presented is a total amount of the alkylene oxide in the present step.

In the preferred mode (third aspect), the reaction between the secondary alcohol alkoxylate and the alkylene oxide may be performed, for example, in any of the following manners: the secondary alcohol alkoxylate and the catalyst are fed to a reactor, and the alkylene oxide is then fed in divided portions to the reactor; the secondary alcohol alkoxylate and the catalyst are fed to the tubular reactor in any order (in the order of the secondary alcohol alkoxylate and then the catalyst, or the catalyst and then the secondary alcohol alkoxylate) or simultaneously, and the alkylene oxide is then fed in divided portions to the reactor; and the secondary alcohol alkoxylate, the alkylene oxide, and the catalyst are fed to the tubular reactor, and the alkylene oxide is then fed from at least one position except the reactor inlet. Preferably, the secondary alcohol alkoxylate, the alkylene oxide, and the catalyst are fed to a tubular reactor, and the alkylene oxide is then fed from at least one position except the reactor inlet under the specific conditions described above. Thereby, local temperature variation in the reactor can be more effectively inhibited (in particular, more effective inhibition/prevention of local temperature increase due to the alkylene oxide addition reaction). Therefore, the coloring of high alkylene oxide adduct of secondary alcohol as a final product can be more effectively reduced. In addition, the number of moles of added alkylene oxide in the high alkylene oxide adduct of secondary alcohol as a final product can be controlled with more ease. Each of the secondary alcohol and the catalyst may be fed at once, or continuously, or in a stepwise manner (in divided portions).

In the preferred mode, shape and size of the tubular reactor are not particularly limited, and any shape and size can be selected according to feeding rates of raw materials (secondary alcohol alkoxylate, alkylene oxide, catalyst) and so on. For example, the tubular reactor (reaction tube) may be linear, or have a bent part (e.g., J shape, U shape, Z shape), or be circular. The tubular reactor (reaction tube) preferably at least has a bent part(s), and more preferably has a structure in which U-shaped reaction tubes are alternately and repeatedly connected as shown in FIG. 4. Thus, in a preferred mode of the present invention, the tubular reactor at least has a bent part(s). In a preferred mode of the present invention, the tubular reactor has a U-shaped reaction tube(s). In a particularly preferred mode of the present invention, the tubular reactor has a structure in which U-shaped reaction tubes are alternately and repeatedly connected.

In the preferred mode (third aspect), an inner diameter of the tubular reactor (reaction tube) is 15 mm or larger and 65 mm or smaller, preferably 20 mm or larger and 50 mm or smaller, but is not limited thereto. An outer diameter of the tubular reactor (reaction tube) is 10 mm or larger and 70 mm or smaller, and preferably 25 mm or larger and 55 mm or smaller, but is not limited thereto. For the tubular reactor (reaction tube), an appropriate length (tube length, total length) can be selected according to production output of the high alkylene oxide adduct of secondary alcohol. For example, the length (tube length) of the tubular reactor (reaction tube) is 100 m or larger and 3000 m or smaller, and preferably larger than 300 m and 2000 m or smaller, but is not limited thereto. With a tubular reactor having such size, hue of high alkylene oxide adduct of secondary alcohol as a final product can be more effectively improved.

In the preferred mode (third aspect), the alkylene oxide is fed from at least one position except the inlet of the tubular reactor (continuously introduced via feeders installed along the longitudinal direction of the tubular reactor). Here, the number of feeds of the alkylene oxide provided, except the inlet, is, for example, 2 or more and 30 or less, preferably 3 or more and 20 or less, and more preferably 5 or more and 18 or less, per 1000 m of the tubular reactor, but is not limited thereto. Thus, in a mode of the present invention, the alkylene oxide is added at 2 to 30 positions per 1000 m of the tubular reactor. In a preferred mode of the present invention, the alkylene oxide is added at 3 to 20 positions per 1000 m of the tubular reactor. In a more preferred mode of the present invention, the alkylene oxide is added at 5 to 18 positions per 1000 m of the tubular reactor. Here, the alkylene oxide feeders may be disposed at any positions in the tubular reactor; however, it is preferable that the alkylene oxide feeders be disposed in the same tube plate of the tubular reactor, as illustrated in FIG. 4. With this configuration, a feeding rate of the alkylene oxide can be controlled, and the coloring can be reduced.

In the preferred mode (third aspect), each alkylene oxide feeder in the tubular reactor may be provided with a system for smooth feeding of the alkylene oxide. Examples of the system include, but are not limited to, a weir provided along a feeder face, a system provided to flow the alkylene oxide selectively from one reaction tube outlet to a desired reaction tube inlet, and a system provided to keep the opening of an inlet or outlet of the reaction tube.

In the preferred mode (third aspect), to each alkylene oxide feeder in the tubular reactor, the alkylene oxide may be supplied from one alkylene oxide feed source as illustrated in FIG. 4, or from different (a plurality of) alkylene oxide sources.

In the preferred mode (third aspect), a thermometer may be installed at only one position in the tubular reactor, but it is preferable that a plurality of thermometers be installed in the reactor. With this configuration, temperature variation during the reaction can be thoroughly checked. Thus, in a preferred mode of the present invention, temperature is measured at at least one position except the inlet of the tubular reactor. Here, the number of thermometers installed is, for example, 5 or more and 50 or less, and preferably 7 or more and 20 or less, per 1000 m of the tubular reactor, but is not limited thereto. An interval to install thermometers is preferably such an interval that each thermometer is installed at a position that is immediately after a place to feed the alkylene oxide to the reactor (e.g., in the range of 0 m or more and less than 100 m from a place to feed the alkylene oxide, preferably within 0 to 80 m therefrom, more preferably within 0 to 50 m therefrom for 80% or more of all the thermometers installed) and allows capture of peak temperature resulting from temperature increase by the reaction, and the interval is 1 m or longer and 50 m or shorter, and preferably 5 m or longer and 10 m or shorter, but is not limited thereto. With the installation of thermometers as described, the addition reaction of the alkylene oxide to the secondary alcohol alkoxylate can be more reliably controlled. Therefore, hue of the high alkylene oxide adduct of secondary alcohol as a final product can be improved.

In the preferred mode (third aspect), known conditions can be employed as reaction conditions for the secondary alcohol alkoxylate and the alkylene oxide (conditions for alkoxylation reaction). For example, a reaction temperature is 120° C. or higher and 180° C. or lower, and preferably 130° C. or higher and 170° C. or lower, but is not limited thereto. The maximum temperature during the reaction is preferably 170° C. or lower, and more preferably lower than 165° C. Thereby, the reduction of hue can be more effectively inhibited. It is preferable to monitor all the thermometers installed to check whether the reaction temperature in the tube rector exceeds peak temperature.

In general, alkylene oxide addition reaction is exothermic reaction. Therefore, the reactor may have a system that circulates heating medium (e.g., warm water) as illustrated in FIG. 4 in order to adjust to reaction temperature as presented above. If a system that flows heating medium is provided, heating medium after circulating (e.g., hot water, water vapor) may be taken out and used for another process. This mode leads to reuse of existing energy, reduction in carbon dioxide emissions, and so on, thus being preferred from the viewpoint of the global environment.

In the preferred mode, a reaction time is 0.1 hour or longer and 2 hours or shorter, and preferably 0.3 hour or longer and 1 hour or shorter, but is not limited thereto. Under such conditions, a desired amount of the alkylene oxide can be added to the secondary alcohol alkoxylate. In addition, hue of high alkylene oxide adduct of secondary alcohol as a final product can be further improved. In the case that two or more reactors are used, the reaction time presented above is total reaction time. Alternatively, once the number of added alkylene oxide in the high alkylene oxide adduct of secondary alcohol generated through the reaction has reached a desired number of added moles as determined by measurement, the reaction may be terminated. A reaction pressure may be normal pressure or increased pressure; however, it is preferable to perform the reaction under increased pressure with inert gas such as nitrogen gas, for example, from the viewpoints of the solubility and reaction rate of the alkylene oxide.

According to the preferred mode as described above, a high alkylene oxide adduct of secondary alcohol represented by the Formula (4): $C_mH_{2m+1}[O(XO)_qH]$, wherein X represents an alkylene group having one to three carbon atoms, m is 12 to 14, and q is more than 3.5 and 50 or less, can be produced. In addition, the method in the preferred mode uses a tubular reactor and hence allows continuous (mass) production. Further, the high alkylene oxide adduct of secondary alcohol produced with the preferred mode is superior in hue, and has high purity. Accordingly, the method in the preferred mode allows continuous (mass) production of a high alkylene oxide adduct of secondary alcohol superior in hue.

In the Formula (4), X and m are as defined in the Formula (1). q is the average number of moles of added alkylene oxide of the high alkylene oxide adduct of secondary alcohol. q is 5 or more and 50 or less, preferably 6 or more and 15 or less, and more preferably 7 or more and 9 or less. The high alkylene oxide adduct of secondary alcohol has high water solubility, and can be preferably used as a surfactant. Herein, for the average number of moles of added alkylene oxide of the secondary alcohol alkoxylate, the "alkylene oxide adduct" in (Average Number of Moles of Added Alkylene Oxide in Alkylene Oxide Adduct) in the above is replaced with "high alkylene oxide adduct of secondary alcohol", and a value determined in the same manner is employed.

The high alkylene oxide adduct of secondary alcohol produced with the present preferred mode is superior in hue (with less or no coloring). Specifically, the hue (APHA) of the high alkylene oxide adduct of secondary alcohol, as the final product, is 70 or lower. Here, the hue (APHA) of the high alkylene oxide adduct of secondary alcohol is preferably 65 or lower, and more preferably 60 or lower. Here, the lower limit of the hue (APHA) of the high alkylene oxide adduct of secondary alcohol is preferably as low as possible but is not limited, and a hue (APHA) of 50 or higher could be sufficient, and the hue (APHA) may be 55 or higher. Thus, the hue (APHA) of the high alkylene oxide adduct of secondary alcohol is preferably 50 to 70, more preferably 50 to 65, and further preferably 50 to 60. Herein, a value determined by a method described later in Examples is employed as the hue (APHA) of the high alkylene oxide adduct of secondary alcohol.

The secondary alcohol alkoxylate produced with the method of the present invention or the high alkylene oxide adduct of secondary alcohol produced with the secondary alcohol alkoxylate is less likely to or does not undergo coloring. In addition, the secondary alcohol alkoxylate produced with the method of the present invention does not or is less likely to gel, and is superior in detergency with less or no generation of odor. Accordingly, the secondary alcohol alkoxylate and high alkylene oxide adduct of secondary alcohol are useful as a raw material of detergent (surfactant) compositions.

Here, a detergent (surfactant) composition containing the secondary alcohol alkoxylate or high alkylene oxide adduct of secondary alcohol may be used alone, or in combination with another conventional, known surfactant. Examples of such surfactants include anionic surfactants such as alkylbenzenesulfonic acid salts, alkylsulfate salts, α-olefinsulfonic acid salts, alkylsulfonic acid salts, aliphatic amide sulfonic acid salts, dialkylsulfosuccinic acid salts, and alkyl ether sulfonate salts; cationic surfactants such as alkylamine salts and quaternary ammonium salts; and amphoteric surfactants such as alkylbetaine.

Various additives can be added to a detergent (surfactant) composition containing the secondary alcohol alkoxylate or high alkylene oxide adduct of secondary alcohol. Examples of such additives include alkaline agents, builders, fragrances, fluorescent brighteners, coloring agents, foaming agents, foam stabilizers, polishing agents, bactericides, bleaching agents, enzymes, preservatives, dyes, and solvents.

Detergent (surfactant) compositions containing the secondary alcohol alkoxylate or high alkylene oxide adduct of secondary alcohol can be effectively used for washing agents, for example, as a washing agent for clothing, fiber products, tableware, containers, miscellaneous goods and instruments, foods, products for building maintenance, residences, furniture, automobiles, aircrafts, or metal products, or as a shampoo or a body shampoo.

Alternatively, the secondary alcohol alkoxylate and high alkylene oxide adduct of secondary alcohol may be used as an emulsifying agent. Examples of oily substances applicable in this case can include, but are not limited to, mineral oils, animal and plant oils, and synthetic oils. These may be used alone, and two or more thereof may be used as a mixture. Examples of mineral oils include spindle oil, machine oil, and liquid paraffin oil. Examples of animal and plant oils can include beef tallow, lard, fish oil, whale oil, rapeseed oil, sesame oil, coconut oil, soybean oil, palm oil, camellia oil, and castor oil. In a mode of the present invention, the emulsifying agent can be used, for example, as an agrochemical, a metalworking oil, a coating material, or an emulsifying agent for emulsion polymerization.

EXAMPLES

The advantageous effects of the present invention will be described with use of Examples and Comparative Examples below. However, the technical scope of the present invention should not be interpreted as being limited to Examples and Comparative Examples below, and examples formed by appropriately combining technical means disclosed in Examples are also included in the scope of the present invention. Unless otherwise specified, operations were performed at room temperature (25° C.) in Examples below. Unless otherwise specified, "%" and "part" indicate "% by mass" and "part by mass", respectively.

Example 1

A cylindrical reactor with a capacity of 3 L was charged with 1000 g of a mixture of saturated aliphatic hydrocarbons having 12 to 14 carbon atoms (average molecular weight: 184) and 25 g of metaboric acid, and liquid-phase oxidation reaction was performed under normal pressure at 170° C. for 2 hours by aerating with a gas having an oxygen concentration of 3.5 vol % and a nitrogen concentration of 96.5 vol % at a rate of 430 L per hour, to afford an oxidation reaction mixed solution (step of oxidation reaction). The mixture of saturated aliphatic hydrocarbons having 12 to 14 carbon atoms used as a raw material contained more than 95% by mass of saturated aliphatic hydrocarbons having 12 to 14 carbon atoms relative to total mass of the mixture of saturated aliphatic hydrocarbons having 12 to 14 carbon atoms.

This oxidation reaction mixed solution was treated at 200 hPa and 170° C. to convert alcohols contained therein into orthoboric acid esters, thereby obtaining borate compounds (boric acid ester mixture) (step of esterification). Next, these borate compounds (boric acid ester mixture) were subjected to flash distillation at 170° C. (column bottom temperature) and 7 hPa (step of recovery of unreacted saturated aliphatic hydrocarbons). Subsequently, the residual solution was hydrolyzed with a large amount (an amount by mass twice that of the residual solution) of hot water at 95° C. to separate into an aqueous layer containing orthoboric acid and an organic layer (step of hydrolysis). The resulting organic layer was subjected to saponification treatment with sodium hydroxide at 140° C. and water washing to remove organic acids and organic acid esters (step of saponification). This organic layer was subjected to fractional distillation at 7 hPa to afford a fraction having a boiling point range of 95 to 120° C., as a first fraction, and a fraction having a boiling point range of 120 to 150° C., as a second fraction (step of purification). At that time, the first fraction (a fraction of 95° C. or higher and lower than 120° C.) was a mixture of small amounts of saturated aliphatic hydrocarbons, carbonyl compounds, and monovalent primary alcohols (monoalcohols). The second fraction (a fraction having a boiling point range of 120 to 150° C.) was a mixture of trace amounts of carbonyl compounds and secondary alcohols (monoalcohols), with most of the secondary alcohols being monovalent secondary alcohols, and the mixture contained more than 95% by mass of secondary alcohols having 12 to 14 carbon atoms relative to total mass of the mixture. A mixture of secondary alcohols (average molecular weight: 200) was obtained as the second fraction.

The mixture of secondary alcohols having 12 to 14 carbon atoms (average molecular weight: 200) was loaded into a tube-type first reactor (tubular reactor, inner capacity: 10 L) at 10 kg/hr, to which boron trifluoride ether complex (acid catalyst) was fed at 24 g/hr. In the first reactor, nine thermometers in total were installed at positions, starting from the reactor inlet, where maximum reaction temperature was to be captured.

Next, ethylene oxide was fed to the first reactor at 3.3 kg/hr separately in three stages, specifically, from the inlet of the first reactor (first stage), a position 20 m away from the inlet (second stage), and a position 40 m away from the inlet (third stage), to perform ethoxylation reaction at 50° C. for 55 minutes; thus, a reaction product was obtained. The ethoxylation reaction temperature was in the range of 40 to 70° C. The feeding rate of ethylene oxide in the ethoxylation reaction was approximately 1.5 mol per mole of the mixture of secondary alcohols.

The reaction product was fed to a second reactor (tank reactor, inner capacity: 10 L) to further perform ethoxylation reaction at 50° C. for 55 minutes; thus, a reaction product containing ethylene oxide adducts was obtained.

The resultant reaction product and 1% by mass aqueous solution of sodium hydroxide were loaded into a first mixing tank of a mixer/settler-type apparatus at 14.8 L/hr and 3.7 L/hr, respectively, stirred at 95° C. for 15 minutes, and washed. Thereafter, the mixture was transferred into a first settling tank of the mixer/settler-type apparatus, and left to stand at 75° C. for 30 minutes in the first settling tank to separate into an organic layer containing ethylene oxide adducts (organic layer 1-1) and an aqueous layer. This organic layer (organic layer 1-1) and water were loaded into a second mixing tank of a mixer/settler-type apparatus at 14.8 L/hr and 3.7 L/hr, respectively, stirred at 95° C. for 15 minutes, and washed. Thereafter, the mixture was transferred into a second settling tank of the mixer/settler-type apparatus, and left to stand at 70° C. for 30 minutes in the second settling tank to separate into an organic layer containing a secondary alcohol ethoxylate precursor (organic layer 1-2) and an aqueous layer; thus, a solution (1) containing a secondary alcohol ethoxylate precursor with the average number of moles of added ethylene oxide (n in the Formula (1)) being 1.7 was obtained. The average number of moles of added ethylene oxide (average number of moles of added EO) in the secondary alcohol ethoxylate precursor in the solution (1) was determined in accordance with a method shown below.

For the organic layer obtained (organic layer 1-2), a test on the appearance of an interface between the organic layer and the aqueous layer in the settling tank and a test on the appearance of an organic layer in the settling tank were performed in accordance with a method shown below. The results are shown in Table 1-1.

<Evaluation Method 1>
(1) Determination of Average Number of Moles of Added Ethylene Oxide (Average Number of Moles of Added EO)

The average number of moles of added ethylene oxide (average number of moles of added EO (n)) in a secondary alcohol ethoxylate precursor is calculated from an analytical value for the hydroxyl value by using the Calculation Formula 2 presented below. The hydroxyl value is determined on the basis of Method B in JIS K1557-1: 2007. Specifically, a sample is prepared as a pyridine solution containing phthalic anhydride, and the hydroxy groups are phthalated under reflux in pyridine. An excessive portion of the phthalation reagent is hydrolyzed with water, and phthalic acid generated is titrated with sodium hydroxide standard solution. The hydroxyl value is determined by calculating the difference between a titration value in a blank test and that in the test on the sample.

$$\text{Average number of moles of added } EO\ (n) = \frac{\left(\frac{56.11 \times 1000}{HV} - MW_A\right)}{44.05} \quad \text{Calculation Formula 2}$$

In the Calculation Formula 2, HV denotes an analytical value for the hydroxyl value; and $MW_A$ denotes an average molecular weight of the mixture of secondary alcohols (200).

(2) Test on Appearance of Interface Between Organic Layer and Aqueous Layer in Settling Tank The presence of an emulsified layer was determined by visual observation of an interface between an organic layer and an aqueous layer in a second settling tank. In the Table 1-1 presented later, "Good" indicates that completely no emulsified layer was observed (less than 5% of total area of the liquid surface) in the interface between the organic layer and the aqueous layer, "Fair" indicates that an emulsified layer was slightly observed (5% or more and less than 30% of total area of the liquid surface) in the interface between the organic layer and the aqueous layer, and "Poor" indicates that an emulsified layer was considerably observed (30% or more of total area of the liquid surface) in the interface between the organic layer and the aqueous layer. Being "Good" or "Fair" suggests that there is no problem in practical uses, and "Good" indicates being highly superior in appearance.

(3) Test on Appearance of Organic Layer in Settling Tank

The presence of crystals in an organic layer in a second settling tank was determined by visual observation. In Table 1-1 presented later, "Good" indicates that completely no crystal was observed in the organic layer, "Fair" indicates that crystals were slightly observed in the organic layer, and "Poor" indicates that crystals were considerably observed in the organic layer. Being "Good" or "Fair" suggests being acceptable for practical uses, and "Good" indicates being highly superior in appearance.

Next, the solution (1) containing the secondary alcohol ethoxylate precursor, which was obtained in the above, was fed to a first distillate remover column (light component separator column), and light components were distilled off at a bottom temperature of 190° C. and a top pressure of 3 hPa and a bottom solution was recovered. The bottom solution was fed to an alcohol recovery column (rectification column) and distilled at a bottom temperature of 190° C. and a top pressure of 25 hPa to distill off unreacted alcohols and fractions with a few moles of added EO; thus, a secondary alcohol ethoxylate (1) was obtained. The average number of moles of added ethylene oxide (p in the Formula (2)) in the secondary alcohol ethoxylate (1) obtained was determined, and found to be 2.9. A yield of a secondary alcohol ethoxylate as a 3-mol adduct (3-mol EO adduct) contained in the secondary alcohol ethoxylate (1) was sufficient ("Good" in the item "Yield" in Table 1-1 presented later).

Hue of the secondary alcohol ethoxylate (1) obtained was evaluated in accordance with a method shown below. The results are shown in Table 1-1 below.

<Evaluation Method 2>
(4) Evaluation of Hue

Each sample (secondary alcohol ethoxylate) was poured into a colorimetric tube to a level of a marked line, and the colorimetric tube was placed on a white paper to make comparison with standard solution under natural light. At that time, comparison was made by looking down from the opening of the colorimetric tube into the bottom surface, and a color number in Hazen units (platinum-cobalt scale) (APHA No.) corresponding to hue of the sample was selected. In Table 1-1 presented later, smaller values of hue (APHA No.) indicate less coloring. It is desirable for practical uses that the hue (APHA No.) be lower than 45.

Example 2

The same operations as those in Example 1 were performed, except that the feeding rate of ethylene oxide was changed to 2.4 kg/hr in Example 1, to separate into an organic layer containing a secondary alcohol ethoxylate precursor (organic layer 2-2) and an aqueous layer; thus, a solution (2) containing a secondary alcohol ethoxylate precursor with the average number of moles of added ethylene oxide being 1.2 was obtained. The feeding rate of ethylene oxide in the above ethoxylation reaction was approximately 1.1 mol per mole of the mixture of secondary alcohols. The average number of moles of added ethylene oxide (average number of moles of added EO) in the secondary alcohol ethoxylate precursor in the solution (2) was determined with the same method as described in Example 1.

For the organic layer obtained (organic layer 2-2), a test on the appearance of the interface between the organic layer and the aqueous layer in the settling tank and a test on the appearance of the organic layer in the settling tank were performed with the same method as described in Example 1. The results are shown in Table 1-1.

Next, the same operations as those in Example 1 were performed, except that the solution (2) obtained above was used in place of the solution (1) in Example 1, to afford a secondary alcohol ethoxylate (2). The average number of moles of added ethylene oxide (p in the Formula (2)) in the secondary alcohol ethoxylate (2) obtained was determined to be 2.7. The content (yield) of a secondary alcohol ethoxylate as a 3-mol adduct (3-mol EO adduct) contained in the secondary alcohol ethoxylate (2) was sufficient, but slightly less than that in Example 1 ("Fair" in the item "Yield" in Table 1-1 presented later).

Hue of the secondary alcohol ethoxylate (2) obtained was evaluated with the same method as described in Example 1. The results are shown in Table 1-1 below.

Example 3

The same operations as those in Example 1 were performed, except that the feeding rate of ethylene oxide was changed to 3.0 kg/hr in Example 1, to separate into an organic layer containing a secondary alcohol ethoxylate precursor (organic layer 3-2) and an aqueous layer; thus, a solution (3) containing a secondary alcohol ethoxylate precursor with the average number of moles of added ethylene oxide being 1.6 was obtained. The feeding rate of ethylene oxide in the above ethoxylation reaction was approximately 1.4 mol per mole of the mixture of secondary alcohols. The average number of moles of added ethylene oxide (average number of moles of added EO) in the secondary alcohol ethoxylate precursor in the solution (2) was determined with the same method as described in Example 1.

For the organic layer obtained (organic layer 3-2), a test on the appearance of the interface between the organic layer and the aqueous layer in the settling tank and a test on the appearance of the organic layer in the settling tank were performed with the same method as described in Example 1. The results are shown in Table 1-1 below.

Next, the same operations as those in Example 1 were performed, except that the solution (3) obtained above was used in place of the solution (1) in Example 1, to afford a secondary alcohol ethoxylate (3). The average number of moles of added ethylene oxide (p in the Formula (2)) in the secondary alcohol ethoxylate (3) obtained was determined to be 2.9. The content (yield) of a secondary alcohol ethoxylate as a 3-mol adduct (3-mol EO adduct) contained in the secondary alcohol ethoxylate (3) was comparable to that in Example 1, thus being sufficient ("Good" in the item "Yield" in Table 1-1 presented later).

Hue of the secondary alcohol ethoxylate (3) obtained was evaluated with the same method as described in Example 1. The results are shown in Table 1-1 below.

Comparative Example 1

The same operations as those in Example 1 were performed, except that the feeding rate of ethylene oxide was changed to 3.9 kg/hr and the ethoxylation reaction in the first reactor was performed at 80° C. in Example 1, to separate into an organic layer containing a secondary alcohol ethoxylate precursor (comparative organic layer 1-2) and an aqueous layer; thus, a solution (4) containing a secondary alcohol ethoxylate with the average number of moles of added ethylene oxide being 2.1 was obtained. The feeding rate of ethylene oxide in the above ethoxylation reaction was approximately 1.8 mol per mole of secondary alcohols. The average number of moles of added ethylene oxide (average number of moles of added EO) in the secondary alcohol ethoxylate precursor in the solution (4) was determined with the same method as described in Example 1. The temperature in the first reactor was inferred to have increased to 80° C. because a large amount of heat of reaction was generated in spite of the fact that ethylene oxide was fed in an amount that would not cause local temperature increase.

For the organic layer obtained (comparative organic layer 1-2), a test on the appearance of the interface between the organic layer and the aqueous layer in the settling tank and a test on the appearance of the organic layer in the settling tank were performed with the same method as described in Example 1. The results are shown in Table 1-1 below.

Next, the same operations as those in Example 1 were performed, except that the solution (4) obtained above was used in place of the solution (1) in Example 1, to afford a comparative secondary alcohol ethoxylate (1). The average number of moles of added ethylene oxide in the comparative secondary alcohol ethoxylate (1) obtained was determined to be 3.1. The content (yield) of a secondary alcohol ethoxylate as a 3-mol adduct (3-mol EO adduct) contained in the comparative secondary alcohol ethoxylate (1) was considerably less than that in Example 1 ("Poor" in the item "Yield" in Table 1-1 presented later).

Hue of the comparative secondary alcohol ethoxylate (1) obtained was evaluated with the same method as described in Example 1. The results are shown in Table 1-1 below.

Comparative Example 2

A reaction product containing ethylene oxide adducts was obtained in the same manner as in Example 1.

The resultant reaction product and 1% by mass aqueous solution of sodium hydroxide were loaded into a first mixing tank of a mixer/settler-type apparatus at 14.8 L/hr and 3.7 L/hr, respectively, stirred at 95° C. for 15 minutes, and washed. Thereafter, the mixture was transferred into a first settling tank of the mixer/settler-type apparatus, and left to stand at 60° C. for 30 minutes in the first settling tank to separate into an organic layer containing ethylene oxide adducts (comparative organic layer 2-1) and an aqueous layer. This organic layer (comparative organic layer 2-1) and water were loaded into a second mixing tank of the mixer/settler-type apparatus at 14.8 L/hr and 3.7 L/hr, respectively, stirred at 95° C. for 15 minutes, and washed. Thereafter, this mixture was transferred into a second settling tank of the mixer/settler-type apparatus, and left to stand at 60° C. for 30 minutes in the second settling tank to separate into an organic layer containing a secondary alcohol ethoxylate precursor (comparative organic layer 2-2) and an aqueous layer; thus, a solution (5) containing a secondary alcohol ethoxylate precursor with the average number of moles of added ethylene oxide being 1.7 was obtained. The average number of moles of added ethylene oxide (average number of moles of added EO) in the secondary alcohol ethoxylate precursor in the solution (5) was determined with the same method as described in Example 1.

For the organic layer obtained (comparative organic layer 2-2), a test on the appearance of the interface between the organic layer and the aqueous layer in the settling tank and a test on the appearance of the organic layer in the settling tank were performed with the same method as described in Example 1. The results are shown in Table 1-1 below.

Next, the same operations as those in Example 1 were performed, except that the solution (5) obtained above was used in place of the solution (1) in Example 1, to afford a comparative secondary alcohol ethoxylate (2). The average number of moles of added ethylene oxide in the comparative secondary alcohol ethoxylate (2) obtained was determined to be 2.9. The content (yield) of a secondary alcohol ethoxylate as a 3-mol adduct (3-mol EO adduct) contained in the comparative secondary alcohol ethoxylate (2) was considerably less than that in Example 1 ("Poor" in the item "Yield" in Table 1-1 presented later).

Hue of the comparative secondary alcohol ethoxylate (2) obtained was evaluated with the same method as described in Example 1. The results are shown in Table 1-1 below.

TABLE 1-1

|  | Example 1 | Example 2 | Example 3 | Comparative Example 1 | Comparative Example 2 |
|---|---|---|---|---|---|
| Conditions for standing (NaOH aq.) | 75° C. × 30 min | 75° C. × 30 min | 75° C. × 30 min | 75° C. × 30 min | 60° C. × 30 min |
| Conditions for standing (water) | 70° C. × 30 min | 70° C. × 30 min | 70° C. × 30 min | 70° C. × 30 min | 60° C. × 30 min |
| Average number of moles of added EO (n in Formula (1)) | 1.7 | 1.2 | 1.6 | 2.1 | 1.7 |
| Test on appearance of interface | Fair | Good | Good | Poor | Poor |
| Test on appearance of organic layer | Fair | Good | Good | Poor | Poor |
| Hue (APHA No.) | 30 to 40 | 20 to 30 | 20 to 30 | 45 to 60 | 45 to 60 |
| Yield | Good | Fair | Good | Poor | Poor |

As shown in Table 1-1 presented, almost no emulsified layer was found in the interface of each of the organic layers 1-2 to 3-2 of Examples 1 to 3; by contrast, considerable formation of an emulsified layer was found for the comparative organic layer 1-2 of Comparative Example 1, in which the average number of moles of added ethylene oxide (n in the Formula (1)) in the secondary alcohol alkoxylate precursor was 2.1, and the comparative organic layer 2-2 of Comparative Example 2, in which the temperature for standing was 60° C. Moreover, it is noted that coloring can be significantly inhibited in the secondary alcohol ethoxylates (1) to (3) of Examples 1 to 3 as compared with the comparative secondary alcohol ethoxylates (1) and (2) of Comparative Examples 1 and 2. In addition to these, almost no precipitation of minute crystals was found in the organic layers 1-2 to 3-2 of Examples 1 to 3; by contrast, considerable crystals were found in the comparative organic layer 1-2 of Comparative Example 1 and the comparative organic layer 2-2 of Comparative Example 2. Therefore, the secondary alcohol ethoxylates (1) to (3) of Examples 1 to 3, produced according to the method of the present invention, are each expected to have superior quality to those of the comparative secondary alcohol ethoxylates (1) and (2) of Comparative Examples 1 and 2.

Example 4

A secondary alcohol ethoxylate (3) (average number of moles of added ethylene oxide=2.9) was obtained in the same manner as in Example 3.

The resultant secondary alcohol ethoxylate (3) (average number of moles of added EO=2.9), 48% by mass aqueous solution of sodium hydroxide, and ethylene oxide were fed to a third reactor (U-shaped reactor, outer diameter: 32 mm, inner diameter: 28 mm, tube length: 650 m) at 1045 kg/hr, 938 g/hr, and 830 kg/hr, respectively. The third reactor had a structure in which 33 U-shaped reaction tubes were alternately and repeatedly connected, where the length of each half of each reaction tube was 10 m. In the third reactor, ethylene oxide feeders (EO feeders) were installed at positions shown in Table 1-2 presented below ("Position of EO feeder" in Table 1-2). In the row "$X_{n'} < X_{n'+1}$" in Table 1-2 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 1-2 presented below, n is 9 and the number of sets of three adjacent ethylene oxide feeders satisfying the relationship: $X_{n'} < X_{n'+1}$ is 6, and hence $N[X_{n'}, X_{n'+1}]/(n-1)$ is approximately 0.8 (=6/8). In addition, 10 thermometers in total were installed near each feeder of ethylene oxide in the second reactor.

Next, ethylene oxide (EO) was fed to the third reactor at rates shown in Table 1-2 presented below ("EO feeding rate" in Table 1-2) via the ethylene oxide feeders (EO feeders) installed at positions shown in Table 1-2 presented below ("Position of EO feeder" in Table 1-2) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with the 10 thermometers installed was 160° C. Ethylene oxide (EO) was fed from the tube plate of the third reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''} < Y_{n''+1}$" in Table 1-2 presented below, sets of two adjacent ethylene oxide feeders satisfying the relationship: $Y_{n''} < Y_{n''+1}$ are provided with "Yes", and sets of two adjacent ethylene oxide feeders not satisfying the relationship: $Y_{n''} < Y_{n''+1}$ (that is, $Y_{n''} > Y_{n''+1}$ or $Y_{n''} = Y_{n''+1}$) are provided with "No". As shown in Table 1-2 presented in the following, n is 9 and the number of sets of two adjacent ethylene oxide feeders satisfying $Y_{n''} < Y_{n''+1}$ is 8, and hence $N[Y_{n''}, Y_{n''+1}]/n$ is approximately 0.9 (=8/9).

TABLE 1-2

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 365 | 440 |
| EO feeder interval (m) | — | 35 | 35 | 40 | 40 | 45 | 50 | 55 | 65 | 75 |
| $X_{n'} < X_{n'+1}$ | — | — | No | Yes | No | Yes | Yes | Yes | Yes | Yes |
| EO feeding rate (kg/hr) | 42 | 49 | 53 | 63 | 64 | 81 | 90 | 109 | 142 | 138 |
| Difference in EO feeding rate (kg/hr) | — | 7 | 4 | 10 | 1 | 18 | 9 | 18 | 33 | −4 |
| $Y_{n''} < Y_{n''+1}$ | — | Yes | Yes | Yes | Yes | Yes | Yes | Yes | Yes | No |

The resultant reaction product containing a secondary alcohol ethoxylate was neutralized with acetic acid to pH 6 to afford a secondary alcohol ethoxylate (A).

The average number of moles of added ethylene oxide (average number of moles of added EO) in the resultant secondary alcohol ethoxylate (A) was determined in accordance with the above method, and found to be 9. Hue (APHA) of the secondary alcohol ethoxylate (A) obtained was evaluated in accordance with the same method as described in Example 1, and found to be 50 to 55.

Thus, the description of the first part of the present invention has been completed.

Subsequently, the second part of the present invention will be described. The present invention should not be considered as being limited only to embodiments shown below. Hereinafter, "the second part of the present invention" is occasionally referred to as "the present invention", simply.

Herein, "X to Y", which shows a range, means "X or more and Y or less", with X and Y included. Unless otherwise specified, operation, measurement of physical properties, and so on are performed at room temperature (20 to 25° C.) and relative humidity of 40 to 50% RH.

<Method for Producing Secondary Alcohol Alkoxylate>

The present invention is to provide a process for producing a secondary alcohol alkoxylate, the method including adding an alkylene oxide to a secondary alcohol alkoxylate precursor via an inlet and alkylene oxide feeders disposed at n positions, except the inlet, in a tubular reactor, wherein n is an integer of 2 or more, to react the secondary alcohol alkoxylate precursor with the alkylene oxide in the tubular reactor, wherein the alkylene oxide feeders are disposed in the tubular reactor so as to satisfy the Expression (i), and the alkylene oxide is added to the secondary alcohol alkoxylate precursor so as to satisfy the Expression (ii) (first aspect):

[Expression (i)]

$$N[X_{n'}, X_{n'+1}]/(n-1) > 0.4 \quad (i)$$

In the Expression (i), $N[X_{n'}, X_{n'+1}]$ represents the number of sets of three adjacent alkylene oxide feeders satisfying the relationship: $X_{n'} < X_{n'+1}$, wherein $X_{n'}$ represents an interval (m) between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor, wherein n' is an integer between 0 or more and n−2 or less, and $X_{n'+1}$ represents an interval (m) between the alkylene oxide feeder $P_{n'+1}$ and an alkylene oxide feeder $P_{n'+2}$ disposed at the (n'+2)th position from the inlet of the tubular reactor,

[Expression (ii)]

$$N[Y_{n''}, Y_{n''+1}]/n \geq 0.3 \quad (ii)$$

In the Expression (ii), $N[Y_{n''}, Y_{n''+1}]$ represents the number of sets of two adjacent alkylene oxide feeders satisfying the relationship: $Y_{n''} < Y_{n''+1}$, wherein $Y_{n''}$ represents a feeding rate (kg/hr) of alkylene oxide at an alkylene oxide feeder $P_{n''}$ disposed at the n''th position from the inlet of the tubular reactor, wherein n'' is an integer between 0 or more and n−1 or less, and $Y_{n''+1}$ represents a feeding rate (kg/hr) of alkylene oxide at an alkylene oxide feeder $P_{n''+1}$ disposed at the (n''+1)th position from the inlet of the tubular reactor.

For using a secondary alcohol alkoxylate (in particular, a secondary alcohol ethoxylate) as a surfactant, increasing the number of moles of added alkylene oxide in the secondary alcohol alkoxylate is effective for enhanced water solubility. For mass production of a secondary alcohol alkoxylate, continuous production is preferred to batch production. An example of continuous production methods is a method using a tubular reactor (reaction tube). Hence, the present inventors have studied about continuous production of a secondary alcohol alkoxylate with a large number of added moles, and revealed that a secondary alcohol alkoxylate having increased hue (a colored secondary alcohol alkoxylate) is obtained in some cases. In view of this, the present inventors have diligently examined for a means to reduce the coloring of a secondary alcohol alkoxylate having a large number of moles of added alkylene oxide in the continuous production method. As a result, they have presumed that in adding an alkylene oxide to a secondary alcohol in two stages (first alkoxylation reaction of adding an alkylene oxide to a secondary alcohol and second alkoxylation reaction of adding an alkylene oxide to a secondary alcohol alkoxylate precursor obtained in the first alkoxylation reaction), local addition of an alkylene oxide to a secondary alcohol alkoxylate precursor in the second alkoxylation reaction is a cause for the increase in hue. Accordingly, diligent examination has been made on control of addition of an alkylene oxide to a secondary alcohol alkoxylate precursor. As a result, they have found that it is effective to produce a secondary alcohol alkoxylate having a large number of moles of added alkylene oxide (high alkylene oxide adduct), as a final product by feeding an alkylene oxide in divided portions to a secondary alcohol alkoxylate precursor (low alkylene oxide adduct having a small number of moles of added alkylene oxide) via a plurality of feeders in a tubular reactor (reaction tube) (divided feed), (i) in such a manner that the Expression (i): $N[X_{n'}, X_{n'+1}]/(n-1) > 0.4$ is satisfied, in other words, an interval of feeding alkylene oxide is extended with a proportion of more than 40%; and (ii) in such a manner that the Expression (ii): $N[Y_{n''}, Y_{n''+1}]/n \geq 0.3$ is satisfied, in other words, a feeding rate is increased with a proportion of 30% or more. The present inventors have expected that, with divided feed in the specific fashion presented, the alkylene oxide addition can be properly controlled, and as a result the coloring of a secondary alcohol alkoxylate (high alkylene oxide adduct), as a final product, can be reduced. In addition, the method is a continuous production method. Hence, this method allows mass production of a secondary alcohol alkoxylate (high alkylene oxide adduct) with reduced coloring. Accordingly, the above configuration allows mass production of a secondary alcohol alkoxylate (high alkylene oxide adduct) with reduced coloring.

The mechanism of the exhibition of the above operation and effect by the configuration of the present invention is on the basis of expectation, and the present invention is not limited to the above expectations.

Figure 6:
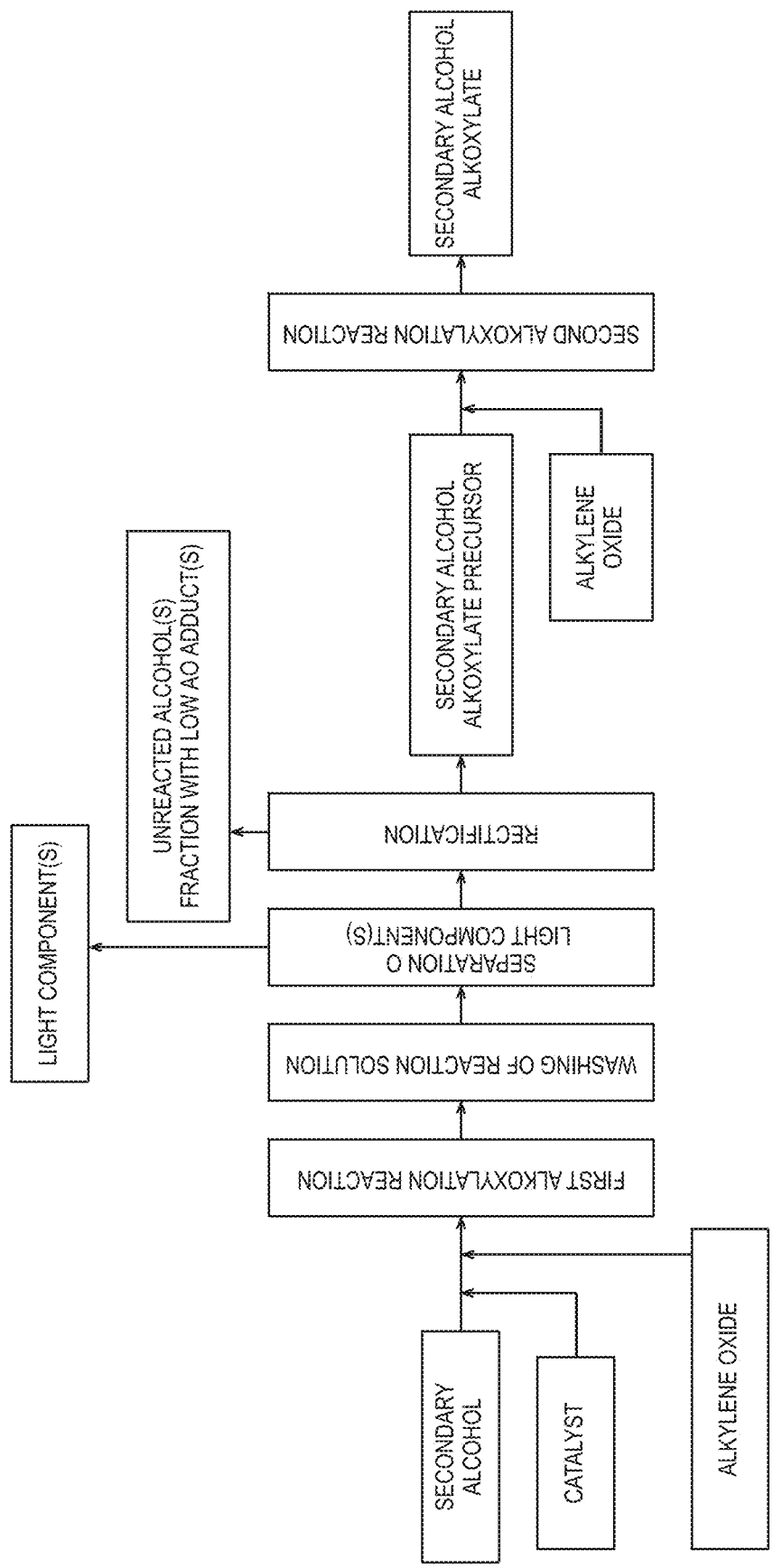
FIG. 6 is a schematic diagram illustrating an embodiment of a production process of the second part of the present invention.

Now, each step of the first aspect will be described with reference to drawings. Specifically, as illustrated in FIG. 6, a secondary alcohol alkoxylate is produced as follows: (i) a secondary alcohol alkoxylate precursor (low alkylene oxide adduct or low-AO adduct) is produced (step (i)); and an alkylene oxide is added to the secondary alcohol alkoxylate precursor produced in step (i) in a tubular reactor (step (ii)). It should be noted that the following description shows an example of each step of the first aspect, and the present invention is not limited to the followings.

(Step (i))

In the present step, a secondary alcohol alkoxylate precursor (low alkylene oxide adduct or low-AO adduct) is produced. The method for producing the secondary alcohol alkoxylate precursor is not limited, and a known method can be applied as it is or with an appropriate modification. For example, a method can be used, including: (i-1) reacting a secondary alcohol with an alkylene oxide in the presence of a catalyst to obtain an alkylene oxide adduct (step of first alkoxylation reaction: "FIRST ALKOXYLATION REACTION" in FIG. 6); (i-2) mixing the alkylene oxide adduct (reaction solution) obtained in step (i-1) with water to separate into an aqueous layer and an organic layer (step of washing: "WASHING OF REACTION SOLUTION" in FIG. 6); and (i-3) purifying the organic layer separated in step (i-2) (step of purification: "SEPARATION OF LIGHT COMPONENT(S)" and "RECTIFICATION" in FIG. 6).

Now, this mode will be described. However, the present invention is not limited to the following mode.

(Step (i-1))

In the present step, a secondary alcohol is reacted with an alkylene oxide in the presence of a catalyst to obtain an alkylene oxide adduct (step of first alkoxylation reaction: "FIRST ALKOXYLATION REACTION" in FIG. 6).

The secondary alcohol, which is a raw material in the alkylene oxide addition reaction, is a mixture of secondary alcohols in each of which a hydroxy group is bonding to a nonterminal carbon atom of a saturated aliphatic hydrocarbon having 11 to 15 carbon atoms (normal paraffin), as represented by the following Formula (A):

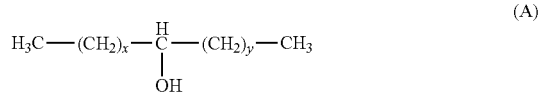

(A)

In the Formula (A), the total of x and y (x+y) is an integer of 8 to 12.

The secondary alcohol is a mixture containing secondary alcohols in each of which a hydroxy group is bonding to a nonterminal carbon atom of a saturated aliphatic hydrocarbon having 11 to 15 carbon atoms (secondary alcohols represented by the Formula (A), wherein x+y is an integer of 8 to 12) (hereinafter, also referred to as "secondary alcohol", simply) as a main component, and preferably a mixture containing secondary alcohols in each of which a hydroxy group is bonding to a nonterminal carbon atom of a saturated aliphatic hydrocarbon having 12 to 14 carbon atoms (secondary alcohol represented by the Formula (A), wherein x+y is an integer of 9 to 11) as a main component. Here, "containing secondary alcohol as a main component" means containing more than 90% by mass (preferably more than 95% by mass) (upper limit: 100% by mass) of secondary alcohol each having a specific number of carbon atoms. An average molecular weight of the secondary alcohol is 158 or higher and 228 or lower, and preferably 186 or higher and 214 or lower. The secondary alcohol may be synthesized, or be a commercially available product.

In a mode of the present invention, a known method such as Japanese Patent Laid-Open No. S48-34807, Japanese Patent Laid-Open No. S56-131531, and Japanese Patent Publication No. S48-37242 can be applied, as it is or with an appropriate modification, as a method for producing the mixture of secondary alcohols represented by the Formula (3). For example, the secondary alcohol can be obtained as follows: a saturated aliphatic hydrocarbon is subjected to liquid-phase oxidation with a gas containing molecular oxygen in the presence of metaboric acid to obtain a reaction solution containing an oxide(s) (step of oxidation reaction); the oxide(s) is esterified to obtain a reaction solution containing borate compound(s) (step of esterification); the reaction solution containing the borate compound(s) is distilled to separate into unreacted saturated aliphatic hydrocarbon(s) and a distillation residue (step of recovery of unreacted saturated aliphatic hydrocarbons); the distillation residue is hydrolyzed to separate into orthoboric acid and an organic layer (step of hydrolysis); the organic layer is saponified with an alkali to separate into an alkaline aqueous solution layer and a crude alcohol layer (step of saponification); and the crude alcohol layer is further purified (step of purification).

In a mode of the present invention, a known method such as Japanese Patent Laid-Open No. 2003-221593, Japanese Patent Laid-Open No. S48-34807, Japanese Patent Laid-Open No. S56-131531, Journal of Japan Oil Chemist's Society, 24, 7, p.p. 427-434 (1975), and Japanese Patent Publication No. S51-046084 can be applied, as it is or with an appropriate modification, as step (i-1) (first alkoxylation reaction). An example of the alkylene oxide addition reaction is shown below. The present invention is not limited by the following method.

For the catalyst, an acid catalyst is used because the number of moles of added alkylene oxide can be controlled to a desired (low) degree. Thus, in a preferred mode of the present invention, the catalyst is an acid catalyst. Examples of the acid catalyst include, but are not limited to, boron trifluoride, boron trifluoride complexes (e.g., ether complex (etherate), phenol complex (phenolate), acetate complex), antimony pentachloride, tin tetrachloride, tris(pentafluorophenyl)borane, phosphoric acid, and sulfuric acid. An amount of the catalyst added is, for example, 0.05 to 0.5% by mass, and preferably more than 0.05% by mass and less than 0.3% by mass, relative to the secondary alcohol, but is not limited thereto.

Preferred as the alkylene oxide (AO) are, for example, ethylene oxide and propylene oxide. In a mode of the present invention, the alkylene oxide may have been subjected to replacement by nitrogen gas before adding the alkylene oxide. An initial nitrogen pressure in replacement by nitrogen gas is preferably 0.05 to 1.0 MPa, and more preferably 0.05 to 0.4 MPa.

A feeding rate of the alkylene oxide can be appropriately adjusted so as to obtain a desired average number of moles of the alkylene oxide added to the secondary alcohol. For example, an amount of the alkylene oxide added is 1.0 mol or more and less than 1.8 mol, preferably more than 1.0 mol or more and less than 1.8 mol, preferably more than 1.0 mol and 1.7 mol or less, more preferably 1.1 to 1.5 mol, and particularly preferably 1.1 to 1.4 mol, per mole of the secondary alcohol (one hydroxy group of the secondary alcohol), but is not limited thereto. In adding the alkylene oxide in divided portions, the amount of the alkylene oxide is a total amount of the alkylene oxide.

The reaction between the secondary alcohol and the alkylene oxide may be performed, for example, in any of the following manners: the secondary alcohol and the catalyst are fed to a reactor, and the alkylene oxide is then fed to the reactor; the secondary alcohol is fed to a reactor, and the catalyst and the alkylene oxide are then fed to the reactor in any order or simultaneously; and the secondary alcohol, the alkylene oxide, and the catalyst are fed to a reactor. Preferably, the secondary alcohol and the catalyst are fed to a reactor, and the alkylene oxide is then fed thereto. Each of the secondary alcohol, the catalyst, and the alkylene oxide may be fed at once, or fed continuously, or fed in a stepwise manner (in divided portions). Preferably, the secondary alcohol and the catalyst are fed to a reactor at once, and the alkylene oxide is fed to the reactor in a stepwise manner (in divided portions). Thereby, the number of moles of added alkylene oxide (m in the Formula (C)) can be controlled within a desired range with more ease.

The reactor to be used for the reaction between the secondary alcohol and the alkylene oxide may be any of tank reactors (batch reactors), tubular reactors (continuous reactors), and continuous tank reactors. These reactors may be combined as appropriate.

The reactor is not limited, and any reactor can be selected according to feeding rates of raw materials (secondary alcohol, alkylene oxide, catalyst) and so on. A tubular reactor (continuous reactor) is preferably used because the alkylene oxide can be fed in divided portions to the reactor with ease. That is, in a preferred embodiment of the present invention, the reaction between the secondary alcohol and the alkylene oxide is performed in a tubular reactor (continuous reactor), and the alkylene oxide is added from at least one position except the inlet of the tubular reactor (i.e., the alkylene oxide is fed in divided portions). Thereby, the number of moles of added alkylene oxide (m in the Formula (C)) can be controlled within a desired range with more ease. In addition, the configuration can reduce temperature variation in the reactor, inhibiting or preventing local temperature increase caused by alkylene oxide addition reaction. A thermometer(s) can be installed in the reactor. Thereby, the temperature during the reaction can be controlled with ease.

In another preferred embodiment of the present invention, alternatively, the reaction between the secondary alcohol and the alkylene oxide is performed in a tank reactor (batch reactor). A thermometer(s) can be installed in the reactor. Thereby, the temperature during the reaction can be controlled with ease.

In still another preferred embodiment of the present invention, alternatively, a tubular reactor and a tank reactor are used in combination. The order to install the tubular reactor and the tank reactor is preferably such that the tank reactor is installed in the downstream of the tubular reactor (a reaction product in the tubular reactor is fed to the tank reactor). The configuration can more effectively inhibit or prevent local temperature increase caused by alkylene oxide addition reaction, and at the same time, can control the number of moles of added alkylene oxide (m in the Formula (C)) with further more ease.

The shape/size of the reactor is not limited, and any shape/size can be appropriately selected according to feeding rates of raw materials (secondary alcohol, alkylene oxide, catalyst) and so on. In the case of a tubular reactor, for example, the reactor (reaction tube) may be linear, or have a bent part (e.g., J shape, U shape, Z shape), or be circular. The tubular reactor (reaction tube) preferably at least has a bent part(s), and more preferably has a structure in which U-shaped reaction tubes are alternately and repeatedly connected. The alkylene oxide may be fed to a plurality of positions of a reactor, and the alkylene oxide is preferably fed to a plurality of positions of a tubular reactor. In the case that a plurality of alkylene oxide feeders is installed in a reactor (in particular, a tubular reactor), it is preferable that an alkylene oxide feeding rate at each feeder be such an amount that a reaction temperature does not increase locally, or such an amount that a reaction temperature is controlled within a preferred range shown below. Alternatively, a place for feeding the alkylene oxide is preferably at a position where a concentration of the alkylene oxide has been lowered by the reaction of the alkylene oxide fed in the previous stage (in the upstream), but are not limited thereto. The reduction of hue can be effectively inhibited by feeding the alkylene oxide in divided portions, as described above, to control the reaction temperature within a proper range (in particular, 70° C. or lower). Further, a thermometer may be installed only at one position in the tubular reactor; however, it is preferable for capturing a peak temperature in the reactor that a plurality of thermometers be installed in the reactor. With this configuration, temperature variation during the reaction can be thoroughly checked. Here, the number of thermometers installed is preferably equal to or larger than the number of positions to feed the alkylene oxide to the reactor, which enables capture of peak temperature in the reactor, and the number of thermometers installed is, for example, 5 or more and 50 or less, and preferably 7 or more and 15 or less, per 100 m of the length of the tubular reactor, but is not limited thereto. An interval to installed thermometers is preferably such an interval that each thermometer is installed at a position that is immediately after a place to feed the alkylene oxide to the reactor (e.g., in the range of 0 m or more and less than 100 m from a place to feed the alkylene oxide, preferably within 0 to 80 m therefrom, more preferably within 0 to 50 m therefrom for 80% or more of all the thermometers installed) and allows capture of peak temperature resulting from temperature increase by the reaction, and the interval is 1 m or longer and 50 m or shorter, and preferably 5 m or longer and 10 m or shorter, but is not limited thereto. With the installation of thermometers as described, the reaction temperature can be controlled within a proper range (in particular, 70° C. or lower) to effectively inhibit the reduction of hue.

Known conditions can be employed as reaction conditions for the secondary alcohol and the alkylene oxide (conditions for alkoxylation reaction). For example, a reaction temperature is 30° C. or higher and 70° C. or lower, and preferably 45° C. or higher and 70° C. or lower, but is not limited thereto. To adjust to the reaction temperature presented, a system to flow heating medium (e.g., warm water) may be provided to a reactor. In using a tubular reactor, it is preferable to monitor all the thermometers installed to check whether the reaction temperature in the tubular reactor exceeds peak temperature. A reaction time is 30 minutes or longer and 150 minutes or shorter, and preferably 50 minutes or longer and 120 minutes or shorter, but is not limited thereto. Under such conditions, the number of moles of added alkylene oxide in the alkylene oxide adduct can be controlled within a desired range with more ease. In addition, generation of coloring inducer(s) as byproducts can be effectively inhibited or prevented. In the case that two or more reactors are used, the reaction time presented above is total reaction time. Alternatively, once the number of added alkylene oxide in the alkylene oxide adduct during the reaction has reached a desired value, as determined by measurement, the reaction may be terminated. A reaction pressure may be normal pressure or increased pressure; however, it is preferable to perform the reaction under increased pressure with inert gas such as nitrogen gas, for example, from the viewpoints of the solubility and reaction rate of the alkylene oxide.

Through the reaction, an alkylene oxide adduct (alkylene oxide adduct A) (a reaction solution containing an alkylene oxide adduct (alkylene oxide adduct A)) can be obtained.

(Step (i-2))

In the present step, the alkylene oxide adduct obtained in step (i-1) (alkylene oxide adduct A) (a reaction solution containing the alkylene oxide adduct (alkylene oxide adduct A); the same is applied hereinafter) is mixed with water to separate into an aqueous layer and an organic layer (step of washing: "WASHING OF REACTION SOLUTION" in FIG. 6). Thereby, an organic layer containing the alkylene oxide adduct is separated. Substantially, the alkylene oxide addition reaction does not proceed (substantially, the number of moles of added alkylene oxide (average number of added moles) in the alkylene oxide adduct does not change) through the step of washing of step (i-2).

The alkylene oxide adduct may be mixed with water alone, or mixed with a solution containing water (hereinafter, also referred to as "washing water"). In the case that washing water is used, the washing water contains, in addition to water, a base such as sodium hydroxide, potassium hydroxide, sodium carbonate, potassium carbonate, and lithium hydroxide, and magnesium hydroxide or the like, though the washing water is not limited thereto. The washing water is preferably a mixed solution of water and a base (in particular, sodium hydroxide, potassium hydroxide) (alkaline aqueous solution). A content of a component such as the base or the like is an amount corresponding to a concentration, for example, of 0.1 to 30% by mass, preferably of 0.5 to 5% by mass, but is not limited thereto. Thereby, a catalyst (in particular, an acid catalyst) can be efficiently removed. A step of mixing for the alkylene oxide adduct and water or washing water may be performed once, or repeated twice or more times. In the latter case, it is preferable that the alkylene oxide adduct be mixed with the washing water to separate into an aqueous layer and an organic layer (organic layer 1), and the organic layer 1 be then mixed with water alone to separate into an aqueous layer and an organic layer (organic layer 2). Thus, in a preferred mode of the present invention, the separation is performed by mixing the reaction solution containing the alkylene oxide adduct with an alkaline aqueous solution to separate into an aqueous layer and an organic layer 1, and then mixing the organic layer 1 with water to separate into an aqueous layer and an organic layer 2. Thereby, coloring inducer(s) can be more efficiently removed.

A mixing ratio between the alkylene oxide adduct and water or washing water (in particular, an alkaline aqueous solution) (reaction solution containing alkylene oxide adduct:water or washing water (mixing ratio by volume)) is preferably 1:1 to 8:1, and more preferably 3:1 to 5:1, but is not limited thereto. Thus, in a preferred mode of the present invention, in mixing the reaction solution containing the alkylene oxide adduct with an alkaline aqueous solution, a mixing ratio by volume between the reaction solution and the alkaline aqueous solution is 1:1 to 8:1. In a preferred mode of the present invention, in mixing the organic layer 1 with water, a mixing ratio by volume between the organic layer 1 and the water is 1:1 to 8:1. In a more preferred mode of the present invention, in mixing the reaction solution containing the alkylene oxide adduct and an alkaline aqueous solution, the mixing ratio by volume between the reaction solution and the alkaline aqueous solution is 3:1 to 5:1. In a more preferred mode of the present invention, in mixing the organic layer 1 with water, the mixing ratio by volume between the organic layer 1 and the water is 3:1 to 5:1. With reduced use of water or washing water in an amount equal to or smaller than (in particular, much smaller than) the amount of the solution containing the alkylene oxide adduct (the reaction solution or the organic layer 1), the emulsified state (in particular, water-in-oil emulsion) (accordingly, coloring) in mixing the reaction solution with water or washing water can be more effectively inhibited or prevented, with ensuring washing efficiency.

Alternatively, the alkylene oxide adduct may be mixed with an alkaline aqueous solution (washing water), to separate into an aqueous layer and an organic layer (organic layer 1), and the organic layer 1 may be mixed with water alone to separate into an aqueous layer and an organic layer (organic layer 2), as necessary.

A method for mixing the alkylene oxide adduct and the water or washing water is not limited, and a known method can be used. Examples thereof include a method which comprises adding water or washing water to the alkylene oxide adduct, and sufficiently stirring and mixing the resultant mixture to dissolve the alkylene oxide adduct in an organic layer and then left to stand, and, after an aqueous layer and an organic layer are separated from each other, the organic layer is taken out. The stirring/mixing conditions in this case are not limited. For example, a stirring/mixing temperature is 40 to 100° C., and preferably 80° C. or higher and lower than 100° C. A stirring/mixing time is 5 to 120 minutes, and preferably 10 minutes or longer and shorter than 30 minutes. In the case that the alkylene oxide adduct is washed with water and washing water (washed with water and then with washing water, or washed with washing water and then with water), identical or different stirring/mixing conditions may be used for the steps of washing.

After being mixed with water or washing water, the reaction solution is left to stand to separate into an aqueous layer and an organic layer. The standing conditions in this case are not limited. A temperature for standing is preferably higher than 60° C. By setting the temperature for standing above 60° C., the formation of an emulsified layer between the aqueous layer and the organic layer can be inhibited, to successfully separate the aqueous layer. As a result, coloring inducer(s) contained in the aqueous layer can be more efficiently removed, and the final product (secondary alcohol alkoxylate) is provided with improved hue. The temperature for standing is preferably higher than 60° C. and lower than 100° C., more preferably higher than 60° C. and 95° C. or lower, and particularly preferably higher than 65° C. and lower than 85° C. A time for standing is, for example, 5 to 120 minutes, and preferably 30 to 60 minutes, but is not limited thereto. An apparatus to be used for mixing the alkylene oxide adduct and water or washing water is not particularly limited, but a mixer/settler-type apparatus capable of stirring/mixing the alkylene oxide adduct and water or a solution for mixing (washing water) in a mixer part (mixing tank) and then separating an aqueous layer and an organic layer from each other in a settler part (settling tank) can be used. Alternatively, an apparatus like a line mixer or a countercurrent washing column may be used.

Through the present step, an organic layer containing the alkylene oxide adduct can be separated. In particular, if the alkylene oxide adduct is mixed with washing water to separate into an aqueous layer and an organic layer (organic layer 1), and the organic layer 1 is then mixed with water alone to separate into an aqueous layer and an organic layer (organic layer 2), the alkylene oxide adduct can be obtained with high purity.

The organic layer obtained through the described process may be dehydrated, as necessary. Thereby, the number of moles of added alkylene oxide (m in the Formula (C)) in the secondary alcohol alkoxylate precursor can be more effectively controlled within a desired range. A dehydration method is not limited, and a known method can be applied as it is or with an appropriate modification. For example, the organic layer can be dehydrated by distillation or fractional distillation. A dehydration pressure (column top (top) pressure) is, for example, 1 to 500 hPa, and preferably 50 to 300 hPa, but is not limited thereto. Herein, a pressure indicates a value of pressure measured with a pressure gauge installed in an upper part of a reactor to measure the pressure of a gas phase part. Unless otherwise specified, the same definition is applied throughout the present specification. A dehydration temperature (bottom temperature) is, for example, 50 to 200° C., and preferably 100 to 150° C., but is not limited thereto. Under such conditions, the number of moles of added alkylene oxide (m in the Formula (C)) in the secondary alcohol alkoxylate precursor can be more effectively controlled within a desired range, with unreacted alcohols and so on efficiently removed.

The average number of moles of added alkylene oxide (k in a Formula (B) presented below) in the alkylene oxide adduct obtained through the present step (alkylene oxide adduct B) is more than 0 and less than 2.1, preferably less than 2.0, more preferably less than 1.8, further preferably 1.7 or less, and particularly preferably less than 1.7. The average number of moles of added alkylene oxide in the alkylene oxide adduct obtained through the present step (alkylene oxide adduct) is more than 0, but is preferably 1.2 or more, and more preferably more than 1.5, for improving a yield of the target product (in particular, a secondary alcohol alkoxylate as a 3-mol adduct (alkylene oxide adduct B)). Such number of added moles allows more efficient production (much more production) of secondary alcohol alkoxylate as a final product with further reduction of the coloring of the secondary alcohol alkoxylate. Thus, in a preferred mode of the present invention, the average number of moles of added alkylene oxide in the alkylene oxide adduct obtained through the present step (alkylene oxide adduct B) is 1.2 or more and less than 2.0. In a more preferred mode of the present invention, the average number of moles of added alkylene oxide in the alkylene oxide adduct obtained through the present step (alkylene oxide adduct B) is more than 1.5 and less than 1.8. In a more preferred mode of the present invention, the average number of moles of added alkylene oxide in the alkylene oxide adduct obtained through the present step (alkylene oxide adduct B) is more than 1.5 and 1.7 or less. In a particularly preferred mode of the present invention, the average number of moles of added alkylene oxide in the alkylene oxide adduct obtained through the present step (alkylene oxide adduct B) is more than 1.5 and less than 1.7. Herein, a value determined by the following method is employed as the average number of moles of added alkylene oxide.

(Average Number of Moles of Added Alkylene Oxide in Alkylene Oxide Adduct)

The average number of moles of added alkylene oxide (average number of moles of added AO) in an alkylene oxide adduct is calculated from an analytical value for a hydroxyl value of the alkylene oxide adduct by using the Calculation Formula 1 presented below. The hydroxyl value is determined on the basis of Method B in JIS K1557-1: 2007. Specifically, a sample is prepared as a pyridine solution containing phthalic anhydride, and a hydroxy group(s) is phthalated under reflux in pyridine. An excessive portion of the phthalation reagent is hydrolyzed with water, and phthalic acid generated is titrated with sodium hydroxide standard solution. The hydroxyl value is determined by calculating the difference between a titration value in a blank test and that in the test on the sample.

$$\text{Average number of moles of added } AO = \frac{\left(\frac{56.11 \times 1000}{HV} - MW_A\right)}{44.05} \quad \text{Calculation Formula 1}$$

In the Calculation Formula 1, HV denotes an analytical value for hydroxyl value of alkylene oxide adduct; and $MW_A$ denotes an average molecular weight of secondary alcohol mixture.

(Step (i-3))

In the present step, the organic layer separated in step (i-2) is purified (step of purification: "SEPARATION OF LIGHT COMPONENT(S)" and "RECTIFICATION" in FIG. 6). Thereby, a secondary alcohol alkoxylate precursor can be obtained.

A purification method is not limited, and a known method can be applied as it is or with an appropriate modification. For example, the organic layer can be purified by distillation or fractional distillation. A purification pressure (column top (top) pressure) is, for example, 1 to 100 hPa, and preferably 3 to 50 hPa, but is not limited thereto. A purification temperature (bottom temperature) is, for example, 150 to 250° C., and preferably 175 to 225° C., but is not limited thereto. Under such conditions, light component(s), unreacted alcohol(s), secondary alcohol alkoxylate fraction(s) with a small number of moles of added alkylene oxide (e.g., less than 2.5 mol), and so on can be efficiently removed to properly separate a desired secondary alcohol alkoxylate precursor. Although a step of purification (step of distillation/fractional distillation) is performed twice in FIG. 6, the step of purification may be performed once or repeatedly. For example, as illustrated in FIG. 6, it is acceptable that light component(s) is removed through a step of separation of light component(s) ("SEPARATION OF LIGHT COMPONENT(S)" in FIG. 6), and unreacted alcohol(s) and low AO adduct fraction(s) with a small moles of added alkylene oxide (e.g., the number of moles of added alkylene oxide=less than 2.5) are then removed through a rectification step ("RECTIFICATION" in FIG. 6). Thereby, a secondary alcohol alkoxylate precursor represented by the following Formula (C) can be obtained.

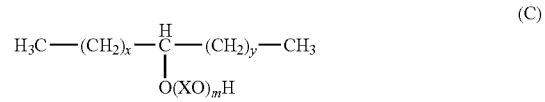

(C)

In the Formula (C), x and y are as defined in the Formula (A).

In the Formula (C), X represents an alkylene group having one to three carbon atoms. Here, the alkylene group having one to three carbon atoms is a methylene group ($-CH_2-$), an ethylene group ($-CH_2CH_2-$), a trimethylene group ($-CH_2CH_2CH_2-$), or a propylene group ($-CH(CH_3)CH_2-$, $-CH_2CH(CH_3)-$). X is preferably an ethylene group. m is the average number of moles of added alkylene oxide in the secondary alcohol alkoxylate precursor. m is preferably 2.5 or more and 3.5 or less, and more preferably more than 2.7 and less than 3.1, but is not limited thereto. Herein, for the average number of moles of added alkylene oxide in the secondary alcohol alkoxylate precursor, the "alkylene oxide adduct" in (Average Number of Moles of Added Alkylene Oxide in Alkylene Oxide Adduct) in the above is replaced with "secondary alcohol alkoxylate precursor", and a value determined in the same manner is employed.

Thus, in a preferred mode of the present invention, the secondary alcohol alkoxylate precursor is represented by the following Formula (C):

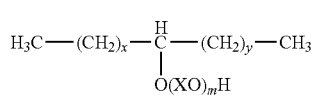
(C)

wherein X represents an alkylene group having one to three carbon atoms, the sum total of x and y (x+y) is an integer of 8 to 12, and m is 2.5 or more and 3.5 or less,
and obtained by reacting a secondary alcohol with an alkylene oxide in the presence of a catalyst to obtain a reaction solution containing an alkylene oxide adduct A, mixing the reaction solution with water and then leaving it to stand at a temperature higher than 60° C. to perform separation into an aqueous layer and an organic layer and to obtain a solution containing an alkylene oxide adduct B represented by the following Formula (B):

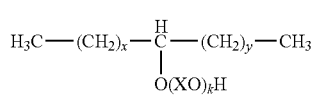
(B)

wherein X and x and y have the same definitions as those in the Formula (C), and k is more than 0 and less than 2.1; and purifying the solution. In this preferred mode, k in the Formula (B) is preferably more than 1.5 and less than 1.8. In that preferred mode, the separation is preferably performed by mixing the reaction solution with an alkaline aqueous solution to separate into an aqueous layer and an organic layer 1 and then mixing the organic layer 1 with water to separate into an aqueous layer and an organic layer 2. In this mode, in mixing the reaction solution with the alkaline aqueous solution, a mixing ratio by volume between the reaction solution and the alkaline aqueous solution is preferably 1:1 to 8:1. In this mode, in mixing the organic layer 1 with the water, a mixing ratio by volume between the organic layer 1 and the water is preferably 1:1 to 8:1.

The secondary alcohol alkoxylate precursor as described above can exhibit satisfactory hue with reduced coloring. Specifically, hue (APHA) of the secondary alcohol alkoxylate precursor is lower than 45, preferably 40 or lower, and more preferably 30 or lower. Here, the lower limit of the hue (APHA) of the secondary alcohol alkoxylate precursor is not limited, and a hue (APHA) of 20 or higher would be enough. Thus, the hue (APHA) of the secondary alcohol alkoxylate precursor is preferably 20 to 40, and more preferably 20 to 30. Herein, a value determined by a method described later in Examples is employed as the hue (APHA) of the secondary alcohol alkoxylate precursor.

(Step (ii))

In the present step, an alkylene oxide is added to the secondary alcohol alkoxylate precursor produced in step (i) in a tubular reactor (step of second alkoxylation reaction: "SECOND ALKOXYLATION REACTION" in FIG. 6). Here, the tubular reactor has an inlet and alkylene oxide feeders at n positions (n is an integer of 2 or more) except the inlet. The alkylene oxide is fed to the secondary alcohol alkoxylate precursor via the alkylene oxide feeders (divided feed) to react the secondary alcohol alkoxylate precursor with the alkylene oxide in the tubular reactor. Herein, an alkylene oxide feeder refers to a feeder through which an alkylene oxide is actually fed. Accordingly, an alkylene oxide feeder that is installed in a tubular reactor to feed an alkylene oxide but, nevertheless, does not feed any alkylene oxide in actual cases is not regarded as an "alkylene oxide feeder" according to the present invention.

In the tubular reactor, the alkylene oxide feeders (including the reactor inlet) are installed in such a manner that the Expression (i) presented below is satisfied. Specifically, in reacting the secondary alcohol and the alkylene oxide, alkylene oxide feeders are provided in such a manner that the feeding interval is extended with the proportion in the Expression (i) being more than 40%.

[Expression (i)]

$$N[X_{n'},X_{n'+1}]/(n-1)>0.4 \quad \text{(i)}$$

In the Expression (i), $N[X_{n'},X_{n'+1}]$ represents the number of sets of three adjacent alkylene oxide feeders satisfying the relationship: $X_{n'}<X_{n'+1}$. Here, $X_{n'}$ represents an interval (m) between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor. n' is an integer of 0 or more and n−2 or less. $X_{n'+1}$ represents an interval (m) between the alkylene oxide feeder $P_{n'+1}$ and an alkylene oxide feeder $P_{n'+2}$ disposed at the (n'+2)th position from the inlet of the tubular reactor. That is, as three adjacent alkylene oxide feeders ($P_{n'}$, $P_{n'+1}$, and $P_{n'+2}$ counted from the tubular reactor inlet) are regarded as one set as illustrated below, $N[X_{n'},X_{n'+1}]$ indicates the number of sets of alkylene oxide feeders in which the interval ($X_{n'+1}$) between the two adjacent alkylene oxide feeders ($P_{n'+1}$ and $P_{n'+2}$) in the outlet (reaction downstream) side is larger than the interval ($X_{n'}$) between the two adjacent alkylene oxide feeders ($P_{n'}$ and $P_{n'+1}$) in the inlet (reaction upstream) side ($X_{n'}<X_{n'+1}$).

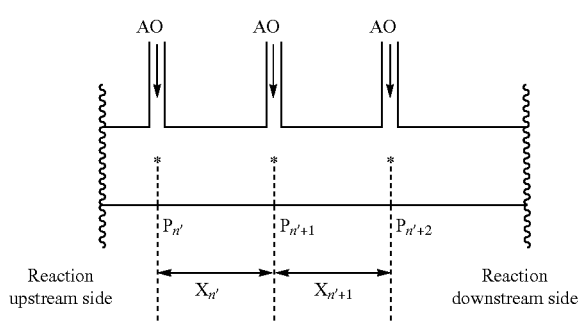

Thus, the Expression (i) means that a proportion of the number of sets of alkylene oxide feeders satisfying the relationship: $X_{n'}<X_{n'+1}(N[X_{n'},X_{n'+1}])$ to the total number of sets of alkylene oxide feeders (n−1) ($N[X_{n'},X_{n'+1}]/(n-1)$) is more than 40% (4/10). Herein, the number of sets of alkylene oxide feeders satisfying the relationship: $X_{n'}<X_{n'+1}(N[X_{n'},X_{n'+1}])$ is divided by the total number of sets of alkylene oxide feeders (n−1) to give a value with two decimal places, which is rounded off to one decimal place and the resultant is employed as "$N[X_{n'},X_{n'+1}]/(n-1)$".

Herein, the reaction tube refers to a part of the tubular reactor where the reaction of adding the alkylene oxide to the secondary alcohol alkoxylate precursor substantially proceeds. Accordingly, in FIG. 7, for example, the reaction tube part between the tubular reactor inlet ($P_0$ in FIG. 7) and the tubular reactor outlet ($P_{outlet}$ in FIG. 7) is the reaction tube according to the present embodiment.

Figure 7:
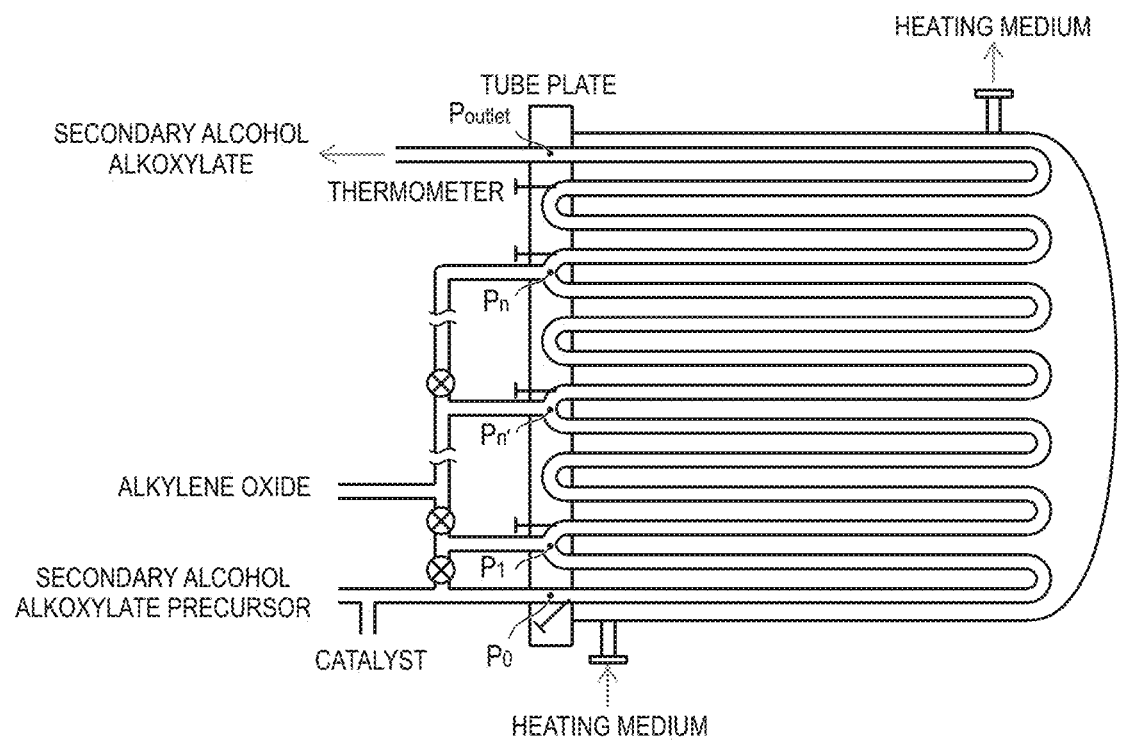
FIG. 7 is a diagram illustrating an example of a tubular reactor according to the second part of the present invention.

Herein, the alkylene oxide feeder with n' being 0 ($P_{0'}$) is the tubular reactor inlet, which is an alkylene oxide feeder installed at the first position in the reaction tube ("$P_{0'}$" in FIG. 7).

Figure 8:
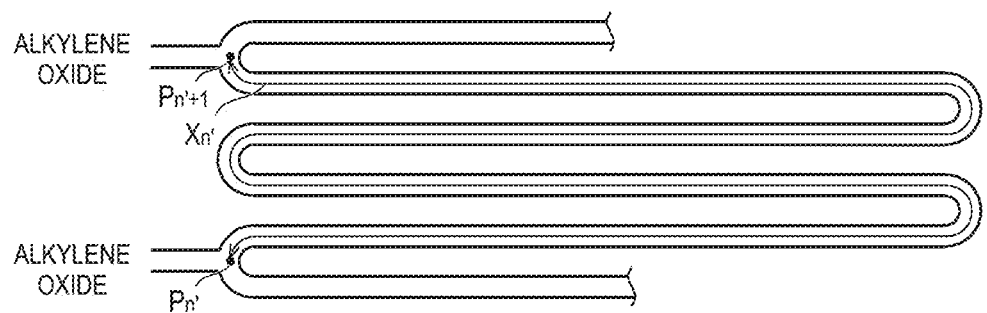
FIG. 8 is a diagram for describing an interval between an alkylene oxide feeder $P_{n'}$ installed at the n'th position counted from the inlet of the tubular reactor in the second part of the present invention and an alkylene oxide feeder $P_{n'+1}$ installed at the (n'+1)th position counted from the inlet of the tubular reactor, $[X_{n'}(m)]$.

Herein, the interval ($X_{n'}$) between two adjacent alkylene oxide feeders ($P_{n'}$ and $P_{n'+1}$) refers to, as illustrated in FIG. 8, a distance between a center of a reaction tube at the alkylene oxide feeder ($P_{n'}$) to feed the alkylene oxide ("$P_{n'}$" in FIG. 8) and a center of a reaction tube at the adjacent alkylene oxide feeder ($P_{n'+1}$) in the reaction downstream side of the alkylene oxide feeder ($P_{n'}$) (a length of a solid line part "$X_{n'}$" in FIG. 8). Here, the "center of the reaction tube" is a point corresponding to a center of gravity of a section obtained by cutting a tube along a plane perpendicular to the longitudinal direction of the reaction tube. In the case that a cross section of a reaction tube is circular, the center of the reaction tube is a center of the circle; in the case that a cross section of a reaction tube is noncircular, the center of the reaction tube is a center of the largest circle among circles that can be drawn in the cross section of the reaction tube. For example, an interval ($X_{1'}$) between an alkylene oxide feeder ($P_{0'}$) and an alkylene oxide feeder ($P_{1'}$) adjacent to the $P_{0'}$ is a distance between a center of the reaction tube at the reaction tube inlet from which the alkylene oxide is first fed (a center part of the tube plate corresponding to a boundary between the tube plate and the reaction tube; see FIG. 7) and a center of the reaction tube at the alkylene oxide feeder from which the alkylene oxide is subsequently fed.

If $N[X_{n'},X_{n'+1}]/(n-1)$ in the Expression (i) is 0.4 or less, the alkylene oxide is fed too frequently to cause local addition of the alkylene oxide to the secondary alcohol alkoxylate precursor, resulting in the coloring of secondary alcohol alkoxylate as a final product (Comparative Examples 1, 3, 4). For improved effects of reducing the coloring of secondary alcohol alkoxylate as a final product, for example, $N[X_{n'},X_{n'+1}]/(n-1)$ in the Expression (i) is preferably 0.5 or more, more preferably more than 0.7, and particularly preferably 0.8 or more. With the present mode, the alkylene oxide addition reaction can be properly controlled through inhibiting local addition reaction of the alkylene oxide to the secondary alcohol alkoxylate precursor, and thus the coloring of secondary alcohol alkoxylate as a final product can be more effectively reduced. Since it is preferable that all the sets of alkylene oxide feeders satisfy $X_{n'} \leq X_{n'+1}$, the upper limit of $N[X_{n'},X_{n'+1}]/(n-1)$ in the Expression (i) is preferably 1, but may be, for example, less than 0.95 or 0.9 or less. Thus, in a preferred mode of the present invention, the alkylene oxide feeders are installed in the tubular reactor in such a manner that the following Expression (i) is satisfied:

[Expression (i')]

$$N[X_{n'},X_{n'+1}]/(n-1) > 0.7 \quad \text{(i')}$$

In the Expression (i'), $N[X_{n'},X_{n'+1}]$ is as defined in the Expression (i).

While the alkylene oxide is fed in such a manner that the feeding interval is extended with the proportion in the Expression (i) being more than 40%, the feeding interval for the alkylene oxide is constant or extended ($X_{n'} \leq X_{n'+1}$) preferably with the proportion in the Expression (i) being more than 80%, more preferably at all of the sets of alkylene oxide feeders. With this configuration, the coloring of secondary alcohol alkoxylate as a final product can be more effectively reduced.

If $X_{n'+1}$ is larger than $X_{n'}$ ($X_{n'} < X_{n'+1}$ is satisfied), then a ratio between an interval between an alkylene oxide feeder $P_{n'+1}$ disposed at the (n'+1)th position from the inlet of the tubular reactor and an alkylene oxide feeder $P_{n'+2}$ disposed at the (n'+2)th position from the inlet of the tubular reactor, $[X_{n'+1}(m)]$, and an interval between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor, $[X_{n'}(m)]$, that is, $[X_{n'+1}/X_{n'}]$, is more than 1. For example, for higher effects of reducing the coloring of secondary alcohol alkoxylate as a final product, the ratio between $X_{n'+1}$ and $X_{n'}$, $[X_{n'+1}/X_{n'}]$, is preferably more than 1.05, and more preferably 1.10 or more, but is not limited thereto. The ratio of $X_{n'}$ to $X_{n'+1}$, $[X_{n'+1}/X_{n'}]$, in that case is, for example, 1.50 or less, and preferably less than 1.30, but is not limited thereto.

A feeding interval for the alkylene oxide (a distance between adjacent alkylene oxide feeders, "$X_{n'}$" in FIG. 8) is, for example, 10 m or larger and 200 m or smaller, preferably 20 m or larger and 150 m or smaller, and more preferably larger than 30 m and smaller than 100 m, but is not limited thereto. Local addition reaction of the alkylene oxide to the secondary alcohol alkoxylate precursor can be more effectively inhibited or prevented. Therefore, hue of the secondary alcohol alkoxylate as a final product can be improved.

Regarding the number of alkylene oxide feeders disposed in the tubular reactor, the alkylene oxide feeders are disposed in such a manner that fewer alkylene oxide feeders are disposed as going to the downstream of the tubular reactor. Preferably, a ratio of the number of alkylene oxide feeders disposed from an inlet to a half point of total tube length of a tubular reactor ($N_{inlet}$) to the number of alkylene oxide feeders disposed beyond the half point of total tube length to an outlet of the tubular reactor ($N_{outlet}$) ($N_{inlet}/N_{outlet}$) is higher than 1.0/1 and 10.0/1 or lower, and preferably 1.5/1 or higher and lower than 5.0/1. Herein, "$N_{inlet}$" denotes, in a total tube length from an inlet to an outlet of a tubular reactor, the number of alkylene oxide feeders disposed in a region from the inlet to a half point of the total tube length (including the reactor inlet and the half point of the total tube length) (also referred to as the "tubular reactor upstream region"). Thus, if an alkylene oxide feeder is disposed at the tubular reactor inlet, the alkylene oxide feeder disposed at the tubular reactor inlet is included as a constituent of the "$N_{inlet}$". "$N_{outlet}$" denotes, in a total tube length from an inlet to an outlet of a tubular reactor, the number of alkylene oxide feeders disposed in a region beyond the half point of the total tube length to an outlet of the tubular reactor (also referred to as the "tubular reactor downstream region"). For "$N_{inlet}/N_{outlet}$", the "$N_{inlet}$" is divided by the "$N_{outlet}$" to give a value with two decimal places, which is rounded off to one decimal place and the resultant is employed. For example, in Example 1 shown later, 10 ethylene oxide feeders in total, including a second reactor inlet, are disposed in a second reactor, the number of ethylene oxide feeders disposed from an inlet to a half point of the total tube length in the second reactor (tubular reactor upstream region) is 8 ($N_{inlet}$=8), and the number of alkylene oxide feeders disposed beyond the half point of the total tube length of the tubular reactor to an outlet (tubular reactor downstream region) in the second reactor is 2 ($N_{outlet}$=2), and hence $N_{inlet}/N_{outlet}$ is 4.0 (=8/2).

In addition, the alkylene oxide is added to the secondary alcohol alkoxylate precursor in such a manner that the Expression (ii) presented below is satisfied. In other words, in reacting the secondary alcohol alkoxylate precursor and the alkylene oxide, the alkylene oxide is fed in such a manner that a feeding rate is increased with a proportion of 30% or more:

[Expression (ii)]

$$N[Y_{n''}, Y_{n''+1}]/n \geq 0.3 \tag{ii}$$

In the Expression (ii), $N[Y_{n''}, Y_{n''+1}]$ represents the number of sets of two adjacent alkylene oxide feeders satisfying the relationship: $Y_{n''} < Y_{n''+1}$. Here, $Y_{n''}$ represents a feeding rate (kg/hr) of alkylene oxide at an alkylene oxide feeder $P_{n''}$ disposed at the n"th position from the inlet of the tubular reactor. n" is an integer of 0 or more and n−1 or less. $Y_{n''+1}$ represents a feeding rate (kg/hr) of alkylene oxide at an alkylene oxide feeder $P_{n''+1}$ disposed at the (n"+1)th position from the inlet of the tubular reactor. That is, as two adjacent alkylene oxide feeders ($P_{n''}$ and $P_{n''+1}$ from the inlet) are regarded as one set, $N[Y_{n''}, Y_{n''+1}]$ represents the number of sets of alkylene oxide feeders in which an alkylene oxide feeding rate ($Y_{n''+1}$) at an alkylene oxide feeder ($P_{n''+1}$) in the outlet (reaction downstream) side is higher than an alkylene oxide feeding rate ($Y_{n''}$) at the adjacent alkylene oxide feeder ($P_{n''}$) in the inlet (reaction upstream) side ($Y_{n''} < Y_{n''+1}$).

Thus, the Expression (ii) means that a proportion of the number of sets of alkylene oxide feeders satisfying the relationship: $Y_{n''} < Y_{n''+1}$ ($N[Y_{n''}, Y_{n''+1}]$) to a total number of sets of alkylene oxide feeders (n) is 30% (3/10) or more. Herein, the number of sets of alkylene oxide feeders satisfying the relationship: $Y_{n''} < Y_{n''+1}$ ($N[Y_{n''}, Y_{n''+1}]$) is divided by the total number of sets of alkylene oxide feeders (n) to give a value with two decimal places, which is rounded off to one decimal place and the resultant is employed as "$N[Y_{n''}, Y_{n''+1}]/n$".

Herein, an alkylene oxide feeder with n" being 0 ($P_{0''}$) is a tubular reactor inlet, which is an alkylene oxide feeder disposed at the first position in a reaction tube ("$P_0$" in FIG. 7).

If $N[Y_{n''}, Y_{n''+1}]/(n-1)$ in the Expression (ii) is less than 0.3, the alkylene oxide addition reaction cannot be properly controlled because of temperature increase in the reactor, resulting in the coloring of secondary alcohol alkoxylate as a final product (Comparative Examples 1, 2, 3, 5). For higher effects of reducing the coloring of secondary alcohol alkoxylate as a final product, for example, $N[Y_{n''}, Y_{n''+1}]/(n-1)$ in the Expression (ii) is preferably 0.6 or more, more preferably more than 0.7, and particularly preferably 0.9 or more. The upper limit of $N[Y_{n''}, Y_{n''+1}]/(n-1)$ in the Expression (ii) is preferably 1, but may be, for example, less than 0.97 or 0.95 or less.

While the alkylene oxide is fed in such a manner that a feeding rate is increased with a proportion in the Expression (ii) being 30% or more, the feeding rate of alkylene oxide is constant or increased ($Y_{n''} \leq Y_{n''+1}$) preferably at more than 80% of, more preferably at 90% or more of the sets of alkylene oxide feeders. With this configuration, the coloring of secondary alcohol alkoxylate as a final product can be more effectively reduced.

If $Y_{n''+1}$ is larger than $Y_{n''}$ ($Y_{n''} < Y_{n''+1}$), then the difference between an alkylene oxide feeding rate ($Y_{n''}$) at an alkylene oxide feeder ($P_{n''}$) in the inlet (reaction upstream) side and an alkylene oxide feeding rate ($Y_{n''+1}$) at the adjacent alkylene oxide feeder ($P_{n''+1}$) in the outlet (reaction downstream) side ($Y_{n''+1} - Y_{n''}$ (kg/hr)) is more than 0 (kg/hr). For example, for higher effects of reducing the coloring of secondary alcohol alkoxylate as a final product, the difference between $Y_{n''}$ and $Y_{n''+1}$ ($Y_{n''+1} - Y_{n''}$ (kg/hr)) in the case that $Y_{n''+1}$ is larger than $Y_{n''}$ ($Y_{n''} < Y_{n''+1}$) is preferably 0.5 (kg/hr) or more and 60 (kg/hr) or less, and more preferably 1 (kg/hr) or more and less than 40 (kg/hr), but is not limited thereto.

In the second alkoxylation reaction, the alkylene oxide is added from the inlet of the tubular reactor and at least one position except the inlet to continuously react the secondary alcohol alkoxylate precursor with the alkylene oxide in the tubular reactor under the conditions as described above. With this configuration, local temperature variation in the reactor can be inhibited (in particular, inhibition/prevention of local temperature increase due to the alkylene oxide addition reaction). Therefore, the coloring of secondary alcohol alkoxylate as a final product can be effectively reduced. In addition, the number of moles of added alkylene oxide in secondary alcohol alkoxylate as a final product can be controlled with ease. It is sufficient for the reaction between the secondary alcohol alkoxylate precursor and the alkylene oxide to be performed in a tubular reactor (continuous reactor), and an additional tank reactor (batch reactor), tubular reactor (continuous reactor), or continuous tank reactor may be provided in the upstream or downstream of the tubular reactor.

In a mode of the present invention, for the alkylene oxide addition reaction, a known method such as Japanese Patent Laid-Open No. 2003-221593, Japanese Patent Laid-Open No. S48-34807, Japanese Patent Laid-Open No. S56-131531, Journal of Japan Oil Chemist's Society, 24, 7, p.p. 427-434 (1975), and Japanese Patent Publication No. S51-046084 can be applied as it is or with an appropriate modification. An example of the alkylene oxide addition reaction will be shown below. The present invention is not limited by the following method.

An alkaline catalyst is used as a catalyst because a secondary alcohol alkoxylate having a desired number of moles of added alkylene oxide can be produced (the number of moles of added alkylene oxide can be controlled to be large). Thus, in a preferred mode of the present invention, the catalyst is an alkaline catalyst. Examples of the alkaline catalyst include, but are not limited to, sodium hydroxide, potassium hydroxide, and sodium alkoxide. An amount of the catalyst is, for example, 0.01 to 1% by mass, and preferably more than 0.02% by mass and less than 0.5% by mass, relative to the secondary alcohol alkoxylate precursor, but is not limited thereto. Alternatively, a feeding rate of the catalyst to the tubular reactor may be 0.1 to 5 kg/hr, and preferably 0.5 to 2 kg/hr, but is not limited thereto. In the present step, the catalyst may be added as it is or in the form of a solution (e.g., an aqueous solution). In the latter case, a concentration of the catalyst in the catalyst solution is about 30 to 70% by mass, but is not limited thereto.

Preferred as the alkylene oxide (AO) are, for example, ethylene oxide and propylene oxide. In a mode of the present invention, the alkylene oxide may have been subjected to replacement by nitrogen gas in adding the alkylene oxide. An initial nitrogen pressure in replacement by nitrogen gas is preferably 1.0 to 2.0 MPa, and more preferably 1.3 to 1.7 MPa.

A feeding rate of the alkylene oxide to the tubular reactor is 300 to 1500 kg/hr, and preferably 700 to 1200 kg/hr, but is not limited thereto. Alternatively, a feeding rate of the alkylene oxide to the tubular reactor may be adjusted so that the average number of moles of the alkylene oxide added to the secondary alcohol (the average number of moles of added alkylene oxide in secondary alcohol alkoxylate as a final product) can reach 5 to 50 mol (preferably 6 to 15 mol, more preferably 7 to 9 mol). For example, an amount of the alkylene oxide to be added is, for example, 5 to 15 mol, and preferably 6 to 12 mol per mole of the secondary alcohol alkoxylate precursor, but is not limited thereto. The amount of the alkylene oxide presented is a total amount of the alkylene oxide in the present step.

The reaction between the secondary alcohol alkoxylate precursor and the alkylene oxide may be performed, for example, in any of the following manners: the secondary alcohol alkoxylate precursor and the catalyst are fed to a reactor, and the alkylene oxide is then fed in divided portions to the reactor; the secondary alcohol alkoxylate precursor and the catalyst are fed to the tubular reactor in any order (in the order of the secondary alcohol alkoxylate precursor and then the catalyst, or the catalyst and then the secondary alcohol alkoxylate precursor) or simultaneously, and the alkylene oxide is then fed in divided portions to the reactor; and the secondary alcohol alkoxylate precursor, the alkylene oxide, and the catalyst are fed to the tubular reactor, and the alkylene oxide is then fed from at least one position except the reactor inlet. Preferably, the secondary alcohol alkoxylate precursor, the alkylene oxide, and the catalyst are fed to a tubular reactor, and the alkylene oxide is then fed from at least one position except the reactor inlet under the specific conditions described above. Thereby, local temperature variation in the reactor can be more effectively inhibited (in particular, more effective inhibition/prevention of local temperature increase due to the alkylene oxide addition reaction). Therefore, the coloring of secondary alcohol alkoxylate as a final product can be more effectively reduced. In addition, the number of moles of added alkylene oxide in the secondary alcohol alkoxylate as a final product can be controlled with more ease. Each of the secondary alcohol alkoxylate precursor and the catalyst may be fed at once, or continuously, or in a stepwise manner (in divided portions).

Shape and size of the tubular reactor are not particularly limited, and any shape and size can be selected according to feeding rates of raw materials (secondary alcohol alkoxylate precursor, alkylene oxide, catalyst) and so on. For example, the tubular reactor (reaction tube) may be linear, or have a bent part (e.g., J shape, U shape, Z shape), or be circular. The tubular reactor (reaction tube) preferably at least has a bent part(s), and more preferably has a structure in which U-shaped reaction tubes are alternately and repeatedly connected as shown in FIG. 7. Thus, in a preferred mode of the present invention, the tubular reactor at least has a bent part(s). In a preferred mode of the present invention, the tubular reactor has a U-shaped reaction tube(s). In a particularly preferred mode of the present invention, the tubular reactor has a structure in which U-shaped reaction tubes are alternately and repeatedly connected.

An inner diameter of the tubular reactor (reaction tube) is 15 mm or larger and 65 mm or smaller, preferably 20 mm or larger and 50 mm or smaller, but is not limited thereto. An outer diameter of the tubular reactor (reaction tube) is 10 mm or larger and 70 mm or smaller, and preferably 25 mm or larger and 55 mm or smaller, but is not limited thereto. For the tubular reactor (reaction tube), an appropriate length (tube length, total length) can be selected according to production output of the secondary alcohol alkoxylate. For example, the length (tube length) of the tubular reactor (reaction tube) is 100 m or larger and 3000 m or smaller, and preferably larger than 300 m and 2000 m or smaller, but is not limited thereto. With a tubular reactor having such size, hue of secondary alcohol alkoxylate as a final product can be more effectively improved.

The alkylene oxide is fed from at least one position except the inlet of the tubular reactor (continuously introduced via feeders installed along the longitudinal direction of the tubular reactor). Here, the number of alkylene oxide feeders provided, except the inlet, is, for example, 2 or more and 30 or less, preferably 3 or more and 20 or less, and more preferably 5 or more and 18 or less, per 1000 m of the tubular reactor, but is not limited thereto. Thus, in a mode of the present invention, the alkylene oxide is added at 2 to 30 positions per 1000 m of the tubular reactor. In a preferred mode of the present invention, the alkylene oxide is added at 3 to 20 positions per 1000 m of the tubular reactor. In a more preferred mode of the present invention, the alkylene oxide is added at 5 to 18 positions per 1000 m of the tubular reactor. Here, the alkylene oxide feeders may be disposed at any positions in the tubular reactor; however, it is preferable that the alkylene oxide feeders be disposed in the same tube plate of the tubular reactor, as illustrated in FIG. 7. With this configuration, a feeding rate of the alkylene oxide can be controlled, and the coloring can be reduced.

Each alkylene oxide feeder in the tubular reactor may be provided with a system for smooth feeding of the alkylene oxide. Examples of the system include, but are not limited to, a weir provided along a feeder face, a system provided to flow the alkylene oxide selectively from one reaction tube outlet to a desired reaction tube inlet, and a system provided to keep the opening of an inlet or outlet of the reaction tube.

To each alkylene oxide feeder in the tubular reactor, the alkylene oxide may be supplied from one alkylene oxide feed source as illustrated in FIG. 7, or from different (a plurality of) alkylene oxide sources.

A thermometer may be installed at only one position in the tubular reactor, but it is preferable that a plurality of thermometers be installed in the reactor. With this configuration, temperature variation during the reaction can be thoroughly checked. Thus, in a preferred mode of the present invention, temperature is measured at at least one position except the inlet of the tubular reactor. Here, the number of thermometers installed is, for example, 5 or more and 50 or less, and preferably 7 or more and 20 or less, per 1000 m of the tubular reactor, but is not limited thereto. An interval to install thermometers is preferably such an interval that each thermometer is installed at a position that is immediately after a place to feed the alkylene oxide to the reactor (e.g., in the range of 0 m or more and less than 100 m from a place to feed the alkylene oxide, preferably within 0 to 80 m therefrom, more preferably within 0 to 50 m therefrom for 80% or more of all the thermometers installed) and allows capture of peak temperature resulting from temperature increase by the reaction, and the interval is 1 m or longer and 50 m or shorter, and preferably 5 m or longer and 10 m or shorter, but is not limited thereto. With the installation of thermometers as described, the addition reaction of the alkylene oxide to the secondary alcohol alkoxylate precursor can be more reliably controlled. Therefore, hue of the secondary alcohol alkoxylate as a final product can be improved.

Known conditions can be employed as reaction conditions for the secondary alcohol alkoxylate precursor and the alkylene oxide (conditions for alkoxylation reaction). For example, a reaction temperature is 120° C. or higher and 180° C. or lower, and preferably 130° C. or higher and 170° C. or lower, but is not limited thereto. The maximum temperature during the reaction is preferably 170° C. or lower, and more preferably lower than 165° C. Thereby, the reduction of hue can be more effectively inhibited. It is preferable to monitor all the thermometers installed to check whether the reaction temperature in the tube rector exceeds peak temperature.

In general, alkylene oxide addition reaction is exothermic reaction. Therefore, the reactor may have a system that circulates heating medium (e.g., warm water) as illustrated in FIG. 7 in order to adjust to reaction temperature as presented above. If a system that flows heating medium is provided, heating medium after circulating (e.g., hot water, water vapor) may be taken out and used for another process. This mode leads to reuse of existing energy, reduction in carbon dioxide emissions, and so on, thus being preferred from the viewpoint of the global environment.

A reaction time is 0.1 hour or longer and 2 hours or shorter, and preferably 0.3 hour or longer and 1 hour or shorter, but is not limited thereto. Under such conditions, a desired amount of the alkylene oxide can be added to the secondary alcohol alkoxylate precursor. In addition, hue of secondary alcohol alkoxylate as a final product can be further improved. In the case that two or more reactors are used, the reaction time presented above is total reaction time. Alternatively, once the number of added alkylene oxide in the secondary alcohol alkoxylate generated through the reaction has reached a desired number of added moles as determined by measurement, the reaction may be terminated. A reaction pressure may be normal pressure or increased pressure; however, it is preferable to perform the reaction under increased pressure with inert gas such as nitrogen gas, for example, from the viewpoints of the solubility and reaction rate of the alkylene oxide.

Through the described process, a secondary alcohol alkoxylate represented by the Formula (D) presented below can be produced. The method uses a tubular reactor, and hence allows continuous (mass) production. The secondary alcohol alkoxylate produced through the process is superior in hue and has high purity. Thus, the method according to the present disclosure enables continuous (mass) production of a secondary alcohol alkoxylate superior in hue.

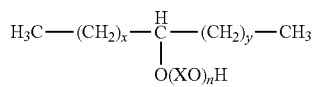

(D)

In the Formula (D), x and y have the same definitions as those in the Formula (A). In the Formula (D), X has the same definition as that in the Formula (B).

In the Formula (D), n is the average number of moles of added alkylene oxide of the secondary alcohol alkoxylate. n is 5 or more and 50 or less, preferably 6 or more and 15 or less, and more preferably 7 or more and 9 or less. The secondary alcohol alkoxylate has high water solubility, and can be preferably used as a surfactant. Herein, for the average number of moles of added alkylene oxide of the secondary alcohol alkoxylate, the "alkylene oxide adduct" in (Average Number of Moles of Added Alkylene Oxide in Alkylene Oxide Adduct) in the above is replaced with "secondary alcohol alkoxylate", and a value determined in the same manner is employed.

The secondary alcohol alkoxylate according to the present invention is superior in hue (with less or no coloring). Specifically, the hue (APHA) of the secondary alcohol alkoxylate is 70 or lower. Here, the hue (APHA) of the secondary alcohol alkoxylate is preferably 65 or lower, and more preferably 60 or lower. Here, the lower limit of the hue (APHA) of the secondary alcohol alkoxylate is preferably as low as possible but is not limited, and a hue (APHA) of 50 or higher could be sufficient, and the hue (APHA) may be 55 or higher. Thus, the hue (APHA) of the secondary alcohol alkoxylate is preferably 50 to 70, more preferably 50 to 65, and further preferably 50 to 60. Herein, a value determined by a method described later in Examples is employed as the hue (APHA) of the secondary alcohol alkoxylate.

The secondary alcohol alkoxylate produced with the method of the present invention or the secondary alcohol alkoxylate produced with the secondary alcohol alkoxylate is less likely to or does not undergo coloring. In addition, the secondary alcohol alkoxylate produced with the method of the present invention does not or is less likely to gel, and is superior in detergency with less or no generation of odor. Accordingly, the secondary alcohol alkoxylate and secondary alcohol alkoxylate are useful as a raw material of detergent (surfactant) compositions.

Here, a detergent (surfactant) composition containing the secondary alcohol alkoxylate may be used alone, or in combination with another conventional, known surfactant. Examples of such surfactants include anionic surfactants such as alkylbenzenesulfonic acid salts, alkylsulfate salts, α-olefinsulfonic acid salts, alkylsulfonic acid salts, aliphatic amide sulfonic acid salts, dialkylsulfosuccinic acid salts, and alkyl ether sulfonate salts; cationic surfactants such as alkylamine salts and quaternary ammonium salts; and amphoteric surfactants such as alkylbetaine.

Various additives can be added to a detergent (surfactant) composition containing the secondary alcohol alkoxylate. Examples of such additives include alkaline agents, builders, fragrances, fluorescent brighteners, coloring agents, foaming agents, foam stabilizers, polishing agents, bactericides, bleaching agents, enzymes, preservatives, dyes, and solvents.

Detergent (surfactant) compositions containing the secondary alcohol alkoxylate can be effectively used for washing agents, for example, as a washing agent for clothing, fiber products, tableware, containers, miscellaneous goods and instruments, foods, products for building maintenance, residences, furniture, automobiles, aircrafts, or metal products, or as a shampoo or a body shampoo.

Alternatively, the secondary alcohol alkoxylate may be used as an emulsifying agent. Examples of oily substances applicable in this case can include, but are not limited to, mineral oils, animal and plant oils, and synthetic oils. These may be used alone, and two or more thereof may be used as a mixture. Examples of mineral oils include spindle oil, machine oil, and liquid paraffin oil. Examples of animal and plant oils can include beef tallow, lard, fish oil, whale oil, rapeseed oil, sesame oil, coconut oil, soybean oil, palm oil, camellia oil, and castor oil. In a mode of the present invention, the emulsifying agent can be used, for example, as an agrochemical, a metalworking oil, a coating material, or an emulsifying agent for emulsion polymerization.

EXAMPLES

The advantageous effects of the present invention will be described with use of Examples and Comparative Examples below. However, the technical scope of the present invention should not be interpreted as being limited to Examples and Comparative Examples below, and examples formed by appropriately combining technical means disclosed in Examples are also included in the scope of the present invention. Unless otherwise specified, operations were performed at room temperature (25° C.) in Examples below.

Unless otherwise specified, "%" and "part" indicate "% by mass" and "part by mass", respectively.

Example 1

A cylindrical reactor with a capacity of 3 L was charged with 1000 g of a mixture of saturated aliphatic hydrocarbons having 12 to 14 carbon atoms (average molecular weight: 184) and 25 g of metaboric acid, and liquid-phase oxidation reaction was performed under normal pressure at 170° C. for 2 hours by aerating with a gas having an oxygen concentration of 3.5 vol % and a nitrogen concentration of 96.5 vol % at a rate of 430 L per hour, to afford an oxidation reaction mixed solution (step of oxidation reaction). The mixture of saturated aliphatic hydrocarbons having 12 to 14 carbon atoms used as a raw material contained more than 95% by mass of saturated aliphatic hydrocarbons having 12 to 14 carbon atoms relative to total mass of the mixture of saturated aliphatic hydrocarbons having 12 to 14 carbon atoms.

This oxidation reaction mixed solution was treated at 200 hPa and 170° C. to convert alcohols contained therein into orthoboric acid esters, thereby obtaining borate compounds (boric acid ester mixture) (step of esterification). Next, these borate compounds (boric acid ester mixture) were subjected to flash distillation at 170° C. (column bottom temperature) and 7 hPa (step of recovery of unreacted saturated aliphatic hydrocarbons). Subsequently, the residual solution was hydrolyzed with a large amount (an amount by mass twice that of the residual solution) of hot water at 95° C. to separate into an aqueous layer containing orthoboric acid and an organic layer (step of hydrolysis). The resulting organic layer was subjected to saponification treatment with sodium hydroxide at 140° C. and water washing to remove organic acids and organic acid esters (step of saponification). This organic layer was subjected to fractional distillation at 7 hPa to afford a fraction having a boiling point range of 95 to 120° C., as a first fraction, and a fraction having a boiling point range of 120 to 150° C., as a second fraction (step of purification). At that time, the first fraction (a fraction of 95° C. or higher and lower than 120° C.) was a mixture of small amounts of saturated aliphatic hydrocarbons, carbonyl compounds, and monovalent primary alcohols (monoalcohols). The second fraction (a fraction having a boiling point range of 120 to 150° C.) was a mixture of trace amounts of carbonyl compounds and secondary alcohols (monoalcohols), with most of the secondary alcohols being monovalent secondary alcohols, and the mixture contained more than 95% by mass of secondary alcohols having 12 to 14 carbon atoms relative to total mass of the mixture. A mixture of secondary alcohols (average molecular weight: 200) was obtained as the second fraction.

The mixture of secondary alcohols having 12 to 14 carbon atoms (average molecular weight: 200) was loaded into a tube-type first reactor (tubular reactor, inner capacity: 10 L) at 10 kg/hr, to which boron trifluoride ether complex (acid catalyst) was fed at 24 g/hr. In the first reactor, nine thermometers in total were installed at positions, starting from the reactor inlet, where maximum reaction temperature was to be captured.

Next, ethylene oxide was fed to the first reactor at 3.3 kg/hr separately in three stages, specifically, from the inlet of the first reactor (first stage), a position 20 m away from the inlet (second stage), and a position 40 m away from the inlet (third stage), to perform ethoxylation reaction at 50° C. for 55 minutes; thus, a reaction product was obtained (step of first alkoxylation reaction). The ethoxylation reaction temperature was in the range of 40 to 70° C. The feeding rate of ethylene oxide in the ethoxylation reaction was approximately 1.5 mol per mole of the mixture of secondary alcohols. The reaction product was fed to a second reactor (tank reactor, inner capacity: 10 L) to further perform ethoxylation reaction at 50° C. for 55 minutes; thus, a reaction product containing an ethylene oxide adduct A was obtained.

Thereafter, 1% by mass NaOH aqueous solution was added to the reaction product at 90° C. to separate into an organic layer and an aqueous layer, and water was then added to the organic layer to separate into an organic layer containing a secondary alcohol ethoxylate precursor and an aqueous layer; thus, a solution containing an ethylene oxide adduct B with the average number of moles of added ethylene oxide being 1.7 was obtained (step of washing).

Next, the resultant solution containing the ethylene oxide adduct B was fed to a first distillate remover column (light component separator column), and light components were distilled off at a bottom temperature of 190° C. and a top pressure of 3 hPa and the bottom solution was recovered. This bottom solution was fed to an alcohol recovery column (rectification column) and distilled at a bottom temperature of 190° C. and a top pressure of 25 hPa to distill off unreacted alcohols and fractions with a few moles of added EO; thus, a secondary alcohol ethoxylate precursor was obtained (step of purification). The average number of moles of added ethylene oxide (average number of moles of added EO) in the secondary alcohol ethoxylate precursor obtained was determined in accordance with the following method, and found to be 2.9.

(1) Determination of Average Number of Moles of Added Ethylene Oxide (Average Number of Moles of Added EO) in Secondary Alcohol Ethoxylate Precursor The average number of moles of added ethylene oxide (average number of moles of added EO (n)) in a secondary alcohol ethoxylate precursor is calculated from an analytical value for the hydroxyl value by using the Calculation Formula 2 presented below. The hydroxyl value is determined on the basis of Method B in JIS K1557-1: 2007. Specifically, a sample is prepared as a pyridine solution containing phthalic anhydride, and the hydroxy groups are phthalated under reflux in pyridine. An excessive portion of the phthalation reagent is hydrolyzed with water, and phthalic acid generated is titrated with sodium hydroxide standard solution. The hydroxyl value is determined by calculating the difference between a titration value in a blank test and that in the test on the sample.

$$\text{Average number of moles of added } EO\ (n) = \frac{\left(\frac{56.11 \times 1000}{HV} - MW_A\right)}{44.05} \quad \text{Calculation Formula 2}$$

In the Calculation Formula 2, HV denotes an analytical value for the hydroxyl value; and $MW_A$ denotes an average molecular weight of the mixture of secondary alcohols (200).

The secondary alcohol ethoxylate precursor (average number of moles of added EO=2.9) obtained in the above, 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33

U-shaped reaction tubes were alternately and repeatedly connected, where the length of each half of each reaction tube was 10 m. In the second reactor, ethylene oxide feeders (EO feeders) were installed at positions shown in Table 2-1 presented later ("Position of EO feeder" in Table 2-1). In the row "$X_{n'} < X_{n'+1}$" in Table 2-1 presented later, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-1 presented later, n is 9 and the number of sets of three adjacent ethylene oxide feeders satisfying the relationship: $X_{n'} < X_{n'+1}(N[X_{n'}, X_{n'+1}])$ is 6, and hence $N[X_{n'}, X_{n'+1}]/(n-1)$ is approximately 0.8 (=6/8). In addition, 10 thermometers in total were installed near each ethylene oxide feeder.

Next, ethylene oxide (EO) was fed to the second reactor at rates shown in Table 2-1 presented later ("EO feeding rate" in Table 2-1) via the ethylene oxide feeders (EO feeders) installed at positions shown in Table 2-1 presented later ("Position of EO feeder" in Table 2-1) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with the 10 thermometers installed was 160° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''} < Y_{n''+1}$" in Table 2-1 presented later, sets of two adjacent ethylene oxide feeders satisfying the relationship: $Y_{n''} < Y_{n''+1}$ are provided with "Yes", and sets of two adjacent ethylene oxide feeders not satisfying the relationship: $Y_{n''} < Y_{n''+1}$ (that is, $Y_{n''} > Y_{n''+1}$ or $Y_{n''} = Y_{n''+1}$) are provided with "No". As shown in Table 2-1 presented in the following, n is 9 and the number of sets of two adjacent ethylene oxide feeders satisfying the relationship: $Y_{n''} < Y_{n''+1}(N[Y_{n''}, Y_{n''+1}])$ is 8, and hence $N[Y_{n''}, Y_{n''+1}]/n$ is approximately 0.9 (=8/9).

(2) Determination of Average Number of Moles of Added Ethylene Oxide (Average Number of Moles of Added EO) in Secondary Alcohol Ethoxylate The average number of moles of added ethylene oxide (average number of moles of added EO (n')) in the thus-isolated secondary alcohol ethoxylate is calculated from an analytical value for the hydroxyl value by using the Calculation Formula 3 presented below. The hydroxyl value is determined on the basis of Method B in JIS K1557-1: 2007. Specifically, a sample is prepared as a pyridine solution containing phthalic anhydride, and the hydroxy groups are phthalated under reflux in pyridine. This reaction is accelerated by using imidazole as a catalyst. An excessive portion of the phthalation reagent is hydrolyzed with water, and phthalic acid generated is titrated with sodium hydroxide standard solution. The hydroxyl value is determined by calculating the difference between a titration value in a blank test and that in the test on the sample.

$$\text{Average number of moles of added } EO(n') = \frac{\left(\frac{56.11 \times 1000}{HV} - MW_A\right)}{44.05} \quad \text{Calculation Formula 3}$$

In the Calculation Formula 3, HV denotes an analytical value for the hydroxyl value of the secondary alcohol ethoxylate; and $MW_A$ denotes an average molecular weight of the mixture of secondary alcohols.

(3) Evaluation of Hue

The secondary alcohol ethoxylate was poured into a colorimetric tube to the level of a marked line, and the colorimetric tube was placed on a white paper to make comparison with standard solution under natural light. At that time, comparison was made by looking down from the opening of the colorimetric tube into the bottom surface, and a color number in Hazen units (platinum-cobalt scale) (APHA No.) corresponding to the hue of the sample was selected. In Table 2-11 presented later, smaller values of hue (APHA No.) indicate less coloring. The hue is acceptable for

TABLE 2-1

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 365 | 440 |
| EO feeder interval (m) | — | 35 | 35 | 40 | 40 | 45 | 50 | 55 | 65 | 75 |
| $X_{n'} < X_{n'+1}$ | — | — | No | Yes | No | Yes | Yes | Yes | Yes | Yes |
| EO feeding rate (kg/hr) | 42 | 49 | 53 | 63 | 64 | 81 | 90 | 109 | 142 | 138 |
| Difference in EO feeding rate (kg/hr) | — | 7 | 4 | 10 | 1 | 18 | 9 | 18 | 33 | −4 |
| $Y_{n''} < Y_{n''+1}$ | — | Yes | Yes | Yes | Yes | Yes | Yes | Yes | Yes | No |

The resultant reaction product containing a secondary alcohol ethoxylate was neutralized with acetic acid to pH 6 to afford a secondary alcohol ethoxylate (1).

The average number of moles of added ethylene oxide (average number of moles of added EO) in the resultant secondary alcohol ethoxylate (1) was determined in accordance with a method shown below, and found to be 9. The hue (APHA) of the secondary alcohol ethoxylate (1) obtained was evaluated in accordance with a method shown below, and found to be 50 to 55.

practical uses if being 70 or lower, and it is desirable that the hue be 65 or lower (in particular, 60 or lower).

Example 2

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-2 presented below ("Position of EO feeder" in Table 2-2). In the row "$X_{n'} < X_{n'+1}$" in Table 2-2 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-2 presented below, n is 9 and the number of sets of three adjacent ethylene oxide feeders satisfying the relationship: $X_{n'} < X_{n'+1}(N[X_{n'}, X_{n'+1}])$ is 4, and hence $N[X_{n'}, X_{n'+1}]/(n-1)$ is approximately 0.5 (=4/8). In addition, a thermometer was installed near each ethylene oxide feeder in the second reactor; thus, 10 thermometers were installed in total.

Next, ethylene oxide (EO) was fed to the second reactor at rates shown in Table 2-2 presented below ("EO feeding rate" in Table 2-2) via the ethylene oxide feeders (EO feeders) installed at positions shown in Table 2-2 presented below ("Position of EO feeder" in Table 2-2) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 163° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''} < Y_{n''+1}$" in Table 2-2 presented below, sets of two adjacent ethylene oxide feeders satisfying the relationship: $Y_{n''} < Y_{n''+1}$ are provided with "Yes", and sets of two adjacent ethylene oxide feeders not satisfying the relationship: $Y_{n''} < Y_{n''+1}$ (that is, $Y_{n''} > Y_{n''+1}$ or $Y_{n''} = Y_{n''+1}$) are provided with "No". As shown in Table 2-2 presented in the following, n is 9 and the number of sets of two adjacent ethylene oxide feeders satisfying the relationship: $Y_{n''} < Y_{n''+1}(N[Y_{n''}, Y_{n''+1}])$ is 8, and hence $N[Y_{n''}, Y_{n''+1}]/n$ is approximately 0.9 (=8/9).

The resultant reaction product containing a secondary alcohol ethoxylate was neutralized in the same manner as in Example 1 to afford a secondary alcohol ethoxylate (2).

The average number of moles of added ethylene oxide (average number of moles of added EO) in the resultant secondary alcohol ethoxylate (2) was determined in accordance with the method described in Example 1, and found to be 9. The hue (APHA) of the secondary alcohol ethoxylate (2) obtained was evaluated in accordance with the method described in Example 1, and found to be 60 to 65.

Example 3

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-3 presented below ("Position of EO feeder" in Table 2-3). In the row "$X_{n'} < X_{n'+1}$" in Table 2-3 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-3 presented below, n is 9 and the number of sets of three adjacent ethylene oxide feeders satisfying the relationship: $X_{n'} < X_{n'+1}(N[X_{n'}, X_{n'+1}])$ is 4, and hence $N[X_{n'}, X_{n'+1}]/(n-1)$ is 0.5 (=4/8). In addition, a thermometer was installed near each ethylene oxide feeder in the second reactor; thus, 10 thermometers were installed in total.

Next, ethylene oxide (EO) was fed to the second reactor at rates shown in Table 2-3 presented below ("EO feeding rate" in Table 2-3) via the ethylene oxide feeders (EO feeders) installed at positions shown in Table 2-3 presented below ("Position of EO feeder" in Table 2-3) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 162° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''} < Y_{n''+1}$" in Table 2-3 presented below, sets of two adjacent ethylene oxide feeders satisfying the relationship: $Y_{n''} < Y_{n''+1}$ are provided with "Yes", and sets of two adjacent ethylene oxide feeders not satisfying the relationship: $Y_{n''} < Y_{n''+1}$ (that is, $Y_{n''} > Y_{n''+1}$ or $Y_{n''} = Y_{n''+1}$) are provided with "No". As shown in Table 2-3 presented in the following, n is 9 and the number of sets of two

TABLE 2-2

|  | $P_0$ | $P_1$ | $P_2$ | $P_3$ | $P_4$ | $P_5$ | $P_6$ | $P_7$ | $P_8$ | $P_9$ |
| --- | --- | --- | --- | --- | --- | --- | --- | --- | --- | --- |
| Position of EO feeder (m) | 0 (inlet) | 35 | 70 | 110 | 150 | 195 | 245 | 300 | 355 | 410 |
| EO feeder interval (m) | — | 35 | 35 | 40 | 40 | 45 | 50 | 55 | 55 | 55 |
| $X_{n'} < X_{n'+1}$ | — | — | No | Yes | No | Yes | Yes | Yes | No | No |
| EO feeding rate (kg/hr) | 53 | 54 | 58 | 68 | 73 | 86 | 100 | 117 | 146 | 74 |
| Difference in EO feeding rate (kg/hr) | — | 1 | 5 | 10 | 5 | 13 | 14 | 17 | 29 | −72 |
| $Y_{n''} < Y_{n''+1}$ | — | Yes | Yes | Yes | Yes | Yes | Yes | Yes | Yes | No | adjacent ethylene oxide feeders satisfying the relationship: $Y_{n''}<Y_{n''+1}(N[Y_{n''},Y_{n''+1}])$ is 9, and hence $N[Y_{n''},Y_{n''+1}]/n$ is 1.0 (=9/9).

addition, a thermometer was installed near each ethylene oxide feeder in the second reactor; thus, 10 thermometers were installed in total.

TABLE 2-3

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 355 | 410 |
| EO feeder interval (m) | — | 35 | 35 | 40 | 40 | 45 | 50 | 55 | 55 | 55 |
| $X_{n'}<X_{n'+1}$ | — | — | No | Yes | No | Yes | Yes | Yes | No | No |
| EO feeding rate (kg/hr) | 53 | 54 | 58 | 68 | 73 | 86 | 100 | 102 | 114 | 121 |
| Difference in EO feeding rate (kg/hr) | — | 1 | 5 | 10 | 5 | 13 | 14 | 2 | 12 | 7 |
| $Y_{n''}<Y_{n''+1}$ | — | Yes | Yes | Yes | Yes | Yes | Yes | Yes | Yes | Yes |

The resultant reaction product containing a secondary alcohol ethoxylate was neutralized in the same manner as in Example 1 to afford a secondary alcohol ethoxylate (3).

The average number of moles of added ethylene oxide (average number of moles of added EO) in the resultant secondary alcohol ethoxylate (3) was determined in accordance with the method described in Example 1, and found to be 9. The hue (APHA) of the secondary alcohol ethoxylate (3) obtained was evaluated in accordance with the method described in Example 1, and found to be 55 to 60, though visual observation confirmed coloring slightly more than that in Example 1.

Example 4

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-4 presented below ("Position of EO feeder" in Table 2-4). In the row "$X_{n'}<X_{n'+1}$" in Table 2-4 presented below, sets of three adjacent ethylene oxide feeders satisfying the relationship: $X_{n'}<X_{n'+1}$ are provided with "Yes", and sets of three adjacent ethylene oxide feeders not satisfying the relationship: $X_{n'}<X_{n'+1}$ (that is, $X_{n'}>X_{n'+1}$ or $X_{n'}=X_{n'+1}$) are provided with "No". As shown in Table 2-4 presented below, n is 9 and the number of sets of three adjacent ethylene oxide feeders satisfying the relationship: $X_{n'}<X_{n'+1}(N[X_{n'},X_{n'+1}])$ is 6, and hence $N[X_{n'},X_{n'+1}]/(n-1)$ is approximately 0.8 (=6/8). In Next, ethylene oxide (EO) was fed to the second reactor at rates shown in Table 2-4 presented below ("EO feeding rate" in Table 2-4) via the ethylene oxide feeders (EO feeders) installed at positions shown in Table 2-4 presented below ("Position of EO feeder" in Table 2-4) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 162° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''}<Y_{n''+1}$" in Table 2-4 presented below, sets of two adjacent ethylene oxide feeders satisfying the relationship: $Y_{n''}<Y_{n''+1}$ are provided with "Yes", and sets of two adjacent ethylene oxide feeders not satisfying the relationship: $Y_{n''}<Y_{n''+1}$ (that is, $Y_{n''}>Y_{n''+1}$ or $Y_{n''}=Y_{n''+1}$) are provided with "No". As shown in Table 2-4 presented in the following, n is 9 and the number of sets of two adjacent ethylene oxide feeders satisfying the relationship: $Y_{n''}<Y_{n''+1}(N[Y_{n''},Y_{n''+1}])$ is 6, and hence $N[Y_{n''},Y_{n''+1}]/n$ is approximately 0.7 (=6/9).

TABLE 2-4

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 365 | 440 |
| EO feeder interval (m) | — | 35 | 35 | 40 | 40 | 45 | 50 | 55 | 65 | 75 |
| $X_{n'}<X_{n'+1}$ | — | — | No | Yes | No | Yes | Yes | Yes | Yes | Yes |
| EO feeding rate (kg/hr) | 53 | 54 | 58 | 68 | 73 | 86 | 109 | 109 | 109 | 109 |
| Difference in EO feeding rate (kg/hr) | — | 1 | 5 | 10 | 5 | 13 | 14 | 0 | 0 | 0 |
| $Y_{n''}<Y_{n''+1}$ | — | Yes | Yes | Yes | Yes | Yes | Yes | No | No | No |

The resultant reaction product containing a secondary alcohol ethoxylate was neutralized in the same manner as in Example 1 to afford a secondary alcohol ethoxylate (4).

The average number of moles of added ethylene oxide (average number of moles of added EO) in the resultant secondary alcohol ethoxylate (4) was determined in accordance with the method described in Example 1, and found to be 9. The hue (APHA) of the secondary alcohol ethoxylate (4) obtained was evaluated in accordance with the method described in Example 1, and found to be 60 to 65.

Example 5

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-5 presented below ("Position of EO feeder" in Table 2-5). In the row "$X_{n'} < X_{n'+1}$" in Table 2-5 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-5 presented below, n is 9 and the number of sets of three adjacent ethylene oxide feeders satisfying the relationship: $X_{n'} < X_{n'+1}(N[X_{n'}, X_{n'+1}])$ is 6, and hence $N[X_{n'}, X_{n'+1}]/(n-1)$ is approximately 0.8 (=6/8). In addition, a thermometer was installed near each ethylene oxide feeder in the second reactor; thus, 10 thermometers were installed in total.

Next, ethylene oxide (EO) was fed to the second reactor at rates shown in Table 2-5 presented below ("EO feeding rate" in Table 2-5) via the ethylene oxide feeders (EO feeders) installed at positions shown in Table 2-5 presented below ("Position of EO feeder" in Table 2-5) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 167° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''} < Y_{n''+1}$" in Table 2-5 presented below, sets of two adjacent ethylene oxide feeders satisfying the relationship: $Y_{n''} < Y_{n''+1}$ are provided with "Yes", and sets of two adjacent ethylene oxide feeders not satisfying the relationship: $Y_{n''} < Y_{n''+1}$ (that is, $Y_{n''} > Y_{n''+1}$ or $Y_{n''} = Y_{n''+1}$) are provided with "No". As shown in Table 2-5 presented in the following, n is 9 and the number of sets of two adjacent ethylene oxide feeders satisfying the relationship: $Y_{n''} < Y_{n''+1}(N[Y_{n''}, Y_{n''+1}])$ is 4, and hence $N[Y_{n''}, Y_{n''+1}]/n$ is approximately 0.4 (=4/9).

The resultant reaction product containing a secondary alcohol ethoxylate was neutralized in the same manner as in Example 1 to afford a secondary alcohol ethoxylate (5).

The average number of moles of added ethylene oxide (average number of moles of added EO) in the resultant secondary alcohol ethoxylate (5) was determined in accordance with the method described in Example 1, and found to be 9. The hue (APHA) of the secondary alcohol ethoxylate (5) obtained was evaluated in accordance with the method described in Example 1, and found to be 65 to 70.

Comparative Example 1

A secondary alcohol ethoxylate precursor was obtained in the same manner as in Example 1.

The secondary alcohol ethoxylate precursor obtained in the above (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-6 presented below ("Position of EO feeder" in Table 2-6). In the row "$X_{n'} < X_{n'+1}$" in Table 2-6 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-6 presented below, n is 9 and the number of sets of three adjacent ethylene oxide feeders satisfying the relationship: $X_{n'} < X_{n'+1}(N[X_{n'}, X_{n'+1}])$ is 0, and hence $N[X_{n'}, X_{n'+1}]/(n-1)$ is 0 (=0/8). In addition, a thermometer was installed near each ethylene oxide feeder in the second reactor; thus, 10 thermometers were installed in total.

Next, ethylene oxide (EO) was fed to the second reactor at rates shown in Table 2-6 presented below ("EO feeding rate" in Table 2-6) via the ethylene oxide feeders (EO feeders) installed at positions shown in Table 2-6 presented below ("Position of EO feeder" in Table 2-6) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 175° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate

TABLE 2-5

| | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 365 | 440 |
| EO feeder interval (m) | — | 35 | 35 | 40 | 40 | 45 | 50 | 55 | 65 | 75 |
| $X_{n'} < X_{n'+1}$ | — | — | No | Yes | No | Yes | Yes | Yes | Yes | Yes |
| EO feeding rate (kg/hr) | 53 | 54 | 58 | 68 | 99 | 99 | 99 | 99 | 99 | 99 |
| Difference in EO feeding rate (kg/hr) | — | 1 | 5 | 10 | 31 | 0 | 0 | 0 | 0 | 0 |
| $Y_{n''} < Y_{n''+1}$ | — | Yes | Yes | Yes | Yes | No | No | No | No | No | precursor. In the row "$Y_{n''}<Y_{n''+1}$" in Table 2-6 presented below, sets of two adjacent ethylene oxide feeders satisfying the relationship: $Y_{n''}<Y_{n''+1}$ are provided with "Yes", and sets of two adjacent ethylene oxide feeders not satisfying the relationship: $Y_{n''}<Y_{n''+1}$ (that is, $Y_{n''}>Y_{n''+1}$ or $Y_{n''}=Y_{n''+1}$) are provided with "No". As shown in Table 2-6 presented in the following, n is 9 and the number of sets of two adjacent ethylene oxide feeders satisfying the relationship: $Y_{n''}<Y_{n''+1}(N[Y_{n''},Y_{n''+1}])$ is 0, and hence $N[Y_{n''},Y_{n''+1}]/n$ is 0 (=%).

adjacent ethylene oxide feeders satisfying the relationship: $X_{n'}<X_{n'+1}$ are provided with "Yes", and sets of three adjacent ethylene oxide feeders not satisfying the relationship: $X_{n'}<X_{n'+1}$ (that is, $X_{n'}>X_{n'+1}$ or $X_{n'}=X_{n'+1}$) are provided with "No". As shown in Table 2-7 presented below, n is 9 and the number of sets of three adjacent ethylene oxide feeders satisfying the relationship: $X_{n'}<X_{n'+1}(N[X_{n'},X_{n'+1}])$ is 6, and hence $N[X_{n'},X_{n'+1}]/(n-1)$ is approximately 0.8 (=6/8). In

TABLE 2-6

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 105 | 140 | 175 | 210 | 245 | 280 | 315 |
| EO feeder interval (m) | — | 35 | 35 | 35 | 35 | 35 | 35 | 35 | 35 | 35 |
| $X_{n'}<X_{n'+1}$ | — | — | No | No | No | No | No | No | No | No |
| EO feeding rate (kg/hr) | 83 | 83 | 83 | 83 | 83 | 83 | 83 | 83 | 83 | 83 |
| Difference in EO feeding rate (kg/hr) | — | 0 | 0 | 0 | 0 | 0 | 0 | 0 | 0 | 0 |
| $Y_{n''}<Y_{n''+1}$ | — | No | No | No | No | No | No | No | No | No |

The resultant reaction product containing a secondary alcohol ethoxylate was neutralized in the same manner as in Example 1 to afford a comparative secondary alcohol ethoxylate (1).

The average number of moles of added ethylene oxide (average number of moles of added EO) in the resultant comparative secondary alcohol ethoxylate (1) was determined in accordance with the method described in Example 1, and found to be 9. The hue (APHA) of the comparative secondary alcohol ethoxylate (1) obtained was evaluated in accordance with the method described in Example 1, and found to be 75 to 80.

Comparative Example 2

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-7 presented below ("Position of EO feeder" in Table 2-7). In the row "$X_{n'}<X_{n'+1}$" in Table 2-7 presented below, sets of three addition, a thermometer was installed near each ethylene oxide feeder in the second reactor; thus, 10 thermometers were installed in total.

Next, ethylene oxide (EO) was fed to the second reactor at rates shown in Table 2-7 presented below ("EO feeding rate" in Table 2-7) via the ethylene oxide feeders (EO feeders) installed at positions shown in Table 2-7 presented below ("Position of EO feeder" in Table 2-7) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 175° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''}<Y_{n''+1}$" in Table 2-7 presented below, sets of two adjacent ethylene oxide feeders satisfying the relationship: $Y_{n''}<Y_{n''+1}$ are provided with "Yes", and sets of two adjacent ethylene oxide feeders not satisfying the relationship: $Y_{n''}<Y_{n''+1}$ (that is, $Y_{n''}>Y_{n''+1}$ or $Y_{n''}=Y_{n''+1}$) are provided with "No". As shown in Table 2-7 presented in the following, n is 9 and the number of sets of two adjacent ethylene oxide feeders satisfying the relationship: $Y_{n''}<Y_{n''+1}(N[Y_{n''},Y_{n''+1}])$ is 0, and hence $N[Y_{n''},Y_{n''+1}]/n$ is 0 (=%).

TABLE 2-7

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 365 | 440 |
| EO feeder interval (m) | — | 35 | 35 | 40 | 40 | 45 | 50 | 55 | 65 | 75 |
| $X_{n'}<X_{n'+1}$ | — | — | No | Yes | No | Yes | Yes | Yes | Yes | Yes |
| EO feeding rate (kg/hr) | 83 | 83 | 83 | 83 | 83 | 83 | 83 | 83 | 83 | 83 |
| Difference in EO feeding rate (kg/hr) | — | 0 | 0 | 0 | 0 | 0 | 0 | 0 | 0 | 0 |
| $Y_{n''}<Y_{n''+1}$ | — | No | No | No | No | No | No | No | No | No |

The resultant reaction product containing a secondary alcohol ethoxylate was neutralized in the same manner as in Example 1 to afford a comparative secondary alcohol ethoxylate (2).

The average number of moles of added ethylene oxide (average number of moles of added EO) in the resultant comparative secondary alcohol ethoxylate (2) was determined in accordance with the method described in Example 1, and found to be 9. The hue (APHA) of the comparative secondary alcohol ethoxylate (2) obtained was evaluated in accordance with the method described in Example 1, and found to be 75 to 80.

Comparative Example 3

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-8 presented below ("Position of EO feeder" in Table 2-8). In the row "$X_{n'} < X_{n'+1}$" in Table 2-8 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-8 presented below, n is 9 and the number of sets of three adjacent ethylene oxide feeders satisfying the relationship: $X_{n'} < X_{n'+1}(N[X_{n'}, X_{n'+1}])$ is 2, and hence $N[X_{n'}, X_{n'+1}]/(n-1)$ is approximately 0.3 (=2/8). In addition, a thermometer was installed near each ethylene oxide feeder in the second reactor; thus, 10 thermometers were installed in total.

Next, ethylene oxide (EO) was fed to the second reactor at rates shown in Table 2-8 presented below ("EO feeding rate" in Table 2-8) via the ethylene oxide feeders (EO feeders) installed at positions shown in Table 2-8 presented below ("Position of EO feeder" in Table 2-8) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 172° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''} < Y_{n''+1}$" in Table 2-8 presented below, sets of two adjacent ethylene oxide feeders satisfying the relationship: $Y_{n''} < Y_{n''+1}$ are provided with "Yes", and sets of two adjacent ethylene oxide feeders not satisfying the relationship: $Y_{n''} < Y_{n''+1}$ (that is, $Y_{n''} > Y_{n''+1}$ or $Y_{n''} = Y_{n''+1}$) are provided with "No". As shown in Table 2-8 presented in the following, n is 9 and the number of sets of two adjacent ethylene oxide feeders satisfying the relationship: $Y_{n''} < Y_{n''+1}(N[Y_{n''}, Y_{n''+1}])$ is 2, and hence $N[Y_{n''}, Y_{n''+1}]/n$ is approximately 0.2 (=2/9).

TABLE 2-8

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 200 | 250 | 300 | 350 | 400 |
| EO feeder interval (m) | — | 35 | 35 | 40 | 40 | 50 | 50 | 50 | 50 | 50 |
| $X_{n'} < X_{n'+1}$ | — | — | No | Yes | No | Yes | No | No | No | No |
| EO feeding rate (kg/hr) | 42 | 49 | 92 | 92 | 92 | 92 | 92 | 92 | 92 | 92 |
| Difference in EO feeding rate (kg/hr) | — | 7 | 44 | 0 | 0 | 0 | 0 | 0 | 0 | 0 |
| $Y_{n''} < Y_{n''+1}$ | — | Yes | Yes | No | No | No | No | No | No | No |

The resultant reaction product containing a secondary alcohol ethoxylate was neutralized in the same manner as in Example 1 to afford a comparative secondary alcohol ethoxylate (3).

The average number of moles of added ethylene oxide (average number of moles of added EO) in the resultant comparative secondary alcohol ethoxylate (3) was determined in accordance with the method described in Example 1, and found to be 9. The hue (APHA) of the comparative secondary alcohol ethoxylate (3) obtained was evaluated in accordance with the method described in Example 1, and found to be 70 to 75.

Comparative Example 4

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diameter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-9 presented below ("Position of EO feeder" in Table 2-9). In the row "$X_{n'} < X_{n'+1}$" in Table 2-9 presented below, sets of three adjacent ethylene oxide feeders satisfying the relationship: $X_{n'} < X_{n'+1}$ are provided with "Yes", and sets of three adjacent ethylene oxide feeders not satisfying the relationship: $X_{n'} < X_{n'+1}$ (that is, $X_{n'} > X_{n'+1}$ or $X_{n'} = X_{n'+1}$) are provided with "No". As shown in Table 2-9 presented below, n is 9 and the number of sets of three adjacent ethylene oxide feeders satisfying the relationship: $X_{n'} < X_{n'+1}(N[X_{n'}, X_{n'+1}])$ is 2, and hence $N[X_{n'}, X_{n'+1}]/(n-1)$ is approximately 0.3 (=2/8). In addition, a thermometer was installed near each ethylene oxide feeder in the second reactor; thus, 10 thermometers were installed in total.

Next, ethylene oxide (EO) was fed to the second reactor at rates shown in Table 2-9 presented below ("EO feeding rate" in Table 2-9) via the ethylene oxide feeders (EO feeders) installed at positions shown in Table 2-9 presented below ("Position of EO feeder" in Table 2-9) to further perform ethoxylation reaction under an initial nitrogen pressure of 1.0 to 2.0 MPa at 140 to 160° C. for 0.5 to 1.0 hour; thus, a reaction product containing a secondary alcohol ethoxylate was obtained. At that time, the maximum reaction temperature of the tubular reactor determined by measurement with all the 10 thermometers was 171° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''}<Y_{n''+1}$" in Table 2-9 presented below, sets of two adjacent ethylene oxide feeders satisfying the relationship: $Y_{n''}<Y_{n''+1}$ are provided with "Yes", and sets of two adjacent ethylene oxide feeders not satisfying the relationship: $Y_{n''}<Y_{n''+1}$ (that is, $Y_{n''}>Y_{n''+1}$ or $Y_{n''}=Y_{n''+1}$) are provided with "No". As shown in Table 2-9 presented in the following, n is 9 and the number of sets of two adjacent ethylene oxide feeders satisfying the relationship: $Y_{n''}<Y_{n''+1}$ ($N[Y_{n''},Y_{n''+1}]$) is 3, and hence $N[Y_{n''},Y_{n''+1}]/n$ is approximately 0.3 (=3/9).

eter: 32 mm, inner diameter: 28 mm, tube length: 650 m) at 1050 kg/hr, 950 g/hr, and 850 kg/hr, respectively. The second reactor had a structure in which 33 U-shaped reaction tubes were alternately and repeatedly connected, where the length of each half of each reaction tube was 10 m. In the second reactor, ethylene oxide feeders (EO feeders) were installed at positions shown in Table 2-10 presented below ("Position of EO feeder" in Table 2-10). In the row "$X_{n'}<X_{n'+1}$" in Table 2-10 presented below, sets of three adjacent ethylene oxide feeders satisfying the relationship: $X_{n'}<X_{n'+1}$ are provided with "Yes", and sets of three adjacent ethylene oxide feeders not satisfying the relationship: $X_{n'}<X_{n'+1}$ (that is, $X_{n'}>X_{n'+1}$ or $X_{n'}=X_{n'+1}$) are provided with "No". As shown in Table 2-10 presented below, n is 9 and the number of sets of three adjacent ethylene oxide feeders satisfying the relationship: $X_{n'}<X_{n'+1}$($N[X_{n'},X_{n'+1}]$) is 4, and hence $N[X_{n'},X_{n'+1}]/(n-1)$ is 0.5 (=4/8). In addition, a thermometer was installed near each ethylene oxide feeder in the second reactor; thus, 10 thermometers were installed in total.

Next, ethylene oxide (EO) was fed to the second reactor at rates shown in Table 2-10 presented below ("EO feeding rate" in Table 2-10) via the ethylene oxide feeders (EO feeders) installed at positions shown in Table 2-10 presented below ("Position of EO feede"r in Table 2-10) to further perform ethoxylation reaction under an initial nitrogen pressure of 1.0 to 2.0 MPa at 140 to 160° C. for 0.5 to 1.0 hour;

TABLE 2-9

| | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 200 | 250 | 300 | 350 | 400 |
| EO feeder interval (m) | — | 35 | 35 | 40 | 40 | 50 | 50 | 50 | 50 | 50 |
| $X_{n'}<X_{n'+1}$ | — | — | No | Yes | No | Yes | No | No | No | No |
| EO feeding rate (kg/hr) | 42 | 49 | 53 | 98 | 98 | 98 | 98 | 98 | 98 | 98 |
| Difference in EO feeding rate (kg/hr) | — | 7 | 4 | 45 | 0 | 0 | 0 | 0 | 0 | 0 |
| $Y_{n''}<Y_{n''+1}$ | — | Yes | Yes | Yes | No | No | No | No | No | No |

The resultant reaction product containing a secondary alcohol ethoxylate was neutralized in the same manner as in Example 1 to afford a comparative secondary alcohol ethoxylate (4).

The average number of moles of added ethylene oxide (average number of moles of added EO) in the resultant comparative secondary alcohol ethoxylate (4) was determined in accordance with the method described in Example 1, and found to be 9. The hue (APHA) of the comparative secondary alcohol ethoxylate (4) obtained was evaluated in accordance with the method described in Example 1, and found to be 70 to 75.

Comparative Example 5

A secondary alcohol ethoxylate precursor was obtained in the same manner as in Example 1.

The resultant secondary alcohol ethoxylate precursor (average number of moles of added EO=2.9), 48% by mass aqueous solution of sodium hydroxide, and ethylene oxide were fed to a second reactor (U-shaped reactor, outer diamthus, a reaction product containing a secondary alcohol ethoxylate was obtained. At that time, the maximum reaction temperature of the tubular reactor determined by measurement with all the 10 thermometers was 172° C. Ethylene oxide (EO) was fed from the tube plate of the second reactor (the ethylene oxide feeders had been installed in substantially the same tube plate). Then, the total feeding rate of ethylene oxide in the ethoxylation reaction was approximately 6 mol per mole of the secondary alcohol ethoxylate precursor. In the row "$Y_{n''}<Y_{n''+1}$" in Table 2-10 presented below, sets of two adjacent ethylene oxide feeders satisfying the relationship: $Y_{n''}<Y_{n''+1}$ are provided with "Yes", and sets of two adjacent ethylene oxide feeders not satisfying the relationship: $Y_{n''}<Y_{n''+1}$ (that is, $Y_{n''}>Y_{n''+1}$ or $Y_{n''}=Y_{n''+1}$) are provided with "No". As shown in Table 2-10 presented in the following, n is 9 and the number of sets of two adjacent ethylene oxide feeders satisfying the relationship: $Y_{n''}<Y_{n''+1}$($N[Y_{n''},Y_{n''+1}]$) is 2, and hence $N[Y_{n''},Y_{n''+1}]/n$ is approximately 0.2 (=2/9).

TABLE 2-10

| | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| Position of EO feeder (m) | 0 (inlet) | 35 | 70 | 110 | 150 | 195 | 245 | 300 | 355 | 410 |
| EO feeder interval (m) | — | 35 | 35 | 40 | 40 | 45 | 50 | 55 | 55 | 55 |

TABLE 2-10-continued

|  | $P_0$ | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| $X_{n'} < X_{n'+1}$ | — | — | No | Yes | No | Yes | Yes | Yes | No | No |
| EO feeding rate (kg/hr) | 42 | 49 | 92 | 92 | 92 | 92 | 92 | 92 | 92 | 92 |
| Difference in EO feeding rate (kg/hr) | — | 7 | 44 | 0 | 0 | 0 | 0 | 0 | 0 | 0 |
| $Y_{n''} < Y_{n''+1}$ | — | Yes | Yes | No | No | No | No | No | No | No |

The resultant reaction product containing a secondary alcohol ethoxylate was neutralized in the same manner as in Example 1 to afford a comparative secondary alcohol ethoxylate (5).

The average number of moles of added ethylene oxide (average number of moles of added EO) in the resultant comparative secondary alcohol ethoxylate (5) was determined in accordance with the method described in Example 1, and found to be 9. The hue (APHA) of the comparative secondary alcohol ethoxylate (5) obtained was evaluated in accordance with the method described in Example 1, and found to be 70 to 75.

Table 2-11 in the following summarizes $N[X_{n'}, X_{n'+1}]/(n-1)$ and $N[Y_{n''}, Y_{n''+1}]/n$ in the second reactors in Examples 1 to 5 and Comparative Examples 1 to 5 above, the maximum reaction temperatures in the second reactors, and the hues of the secondary alcohol ethoxylates.

TABLE 2-11

|  | Example 1 | Example 2 | Example 3 | Example 4 | Example 5 | Comparative Example 1 |
|---|---|---|---|---|---|---|
| $N[X_{n'}, X_{n'+1}]/(n+1)$ | 0.8 | 0.5 | 0.5 | 0.8 | 0.8 | 0 |
| $N[Y_{n''}, Y_{n''+1}]/n$ | 0.9 | 0.9 | 1.0 | 0.7 | 0.4 | 0 |
| Hue (APHA No.) | 50-55 | 60-65 | 55-60 | 60-65 | 65-70 | 75-80 |

|  | Comparative Example 2 | Comparative Example 3 | Comparative Example 4 | Comparative Example 5 |
|---|---|---|---|---|
| $N[X_{n'}, X_{n'+1}]/(n+1)$ | 0.8 | 0.3 | 0.3 | 0.5 |
| $N[Y_{n''}, Y_{n''+1}]/n$ | 0 | 0.2 | 0.3 | 0.2 |
| Hue (APHA No.) | 75-80 | 70-75 | 70-75 | 70-75 |

As demonstrated in Table 2-11 presented, it is noted that the secondary alcohol ethoxylates (1) to (5) of Examples are superior in hue to the comparative secondary alcohol ethoxylates (1) to (5). While evaluation was performed with the tubular reactor having a tube length of about 400 m in the present examples, even tubular reactors or the like of larger tube length (e.g., 700 to 1000 m) are inferred to give results similar to those shown above.

Example 6

A cylindrical reactor with a capacity of 3 L was charged with 1000 g of a mixture of saturated aliphatic hydrocarbons having 12 to 14 carbon atoms (average molecular weight: 184) and 25 g of metaboric acid, and liquid-phase oxidation reaction was performed under normal pressure at 170° C. for 2 hours by aerating with a gas having an oxygen concentration of 3.5 vol % and a nitrogen concentration of 96.5 vol % at a rate of 430 L per hour to afford an oxidation reaction mixed solution (step of oxidation reaction). The mixture of saturated aliphatic hydrocarbons having 12 to 14 carbon atoms used as a raw material contained more than 95% by mass of saturated aliphatic hydrocarbons having 12 to 14 carbon atoms relative to total mass of the mixture of saturated aliphatic hydrocarbons having 12 to 14 carbon atoms.

This oxidation reaction mixed solution was treated at 200 hPa and 170° C. to convert alcohols contained therein into orthoboric acid esters, thereby obtaining borate compounds (boric acid ester mixture) (step of esterification). Next, the borate compounds (boric acid ester mixture) were subjected to flash distillation at 170° C. (column bottom temperature) and 7 hPa (step of recovery of unreacted saturated aliphatic hydrocarbons). Subsequently, the residual solution was hydrolyzed with a large amount (an amount by mass twice that of the residual solution) of hot water at 95° C. to separate into an aqueous layer containing orthoboric acid and an organic layer (step of hydrolysis). The resulting organic layer was subjected to saponification treatment with sodium hydroxide at 140° C. and water washing to remove organic acids and organic acid esters (step of saponification). This organic layer was subjected to fractional distillation at 7 hPa to afford a fraction having a boiling point range of 95 to 120° C., as a first fraction, and a fraction having a boiling point range of 120 to 150° C., as a second fraction (step of purification). At that time, the first fraction (a fraction of 95° C. or higher and lower than 120° C.) was a mixture of small amounts of saturated aliphatic hydrocarbons, carbonyl compounds, and monovalent primary alcohols (monoalcohols). The second fraction (a fraction having a boiling point range of 120 to 150° C.) was a mixture of trace amounts of carbonyl compounds and secondary alcohols (monoalcohols), with most of the secondary alcohols being monovalent secondary alcohols, and the mixture contained more than 95% by mass of secondary alcohols having 12 to 14 carbon atoms relative to total mass of the mixture. A mixture of secondary alcohols (average molecular weight: 200) was obtained as the second fraction.

The mixture of secondary alcohols having 12 to 14 carbon atoms (average molecular weight: 200) was loaded into a tube-type first reactor (tubular reactor, inner capacity: 10 L) at 10 kg/hr, to which boron trifluoride etherate (acid catalyst) was fed at 24 g/hr. The mixture of secondary alcohols, as a raw material, contained more than 95% by mass of secondary alcohols having 12 to 14 carbon atoms relative to total mass of the mixture. In the first reactor, nine thermometers in total were installed at positions, starting from the reactor inlet, where maximum reaction temperature was to be captured.

Next, ethylene oxide was fed to the first reactor at 3.0 kg/hr separately in three stages, specifically, from the inlet of the first reactor (first stage), a position 20 m away from the inlet (second stage), and a position 40 m away from the inlet (third stage), to perform ethoxylation reaction at 50° C. for 55 minutes; thus, a reaction product was obtained. The ethoxylation reaction temperature was in the range of 40 to 70° C. The feeding rate of ethylene oxide in the ethoxylation reaction was approximately 1.4 mol per mole of the mixture of secondary alcohols.

The reaction product was fed to a second reactor (tank reactor, inner capacity: 10 L) to further perform ethoxylation reaction at 50° C. for 55 minutes; thus, a reaction product containing ethylene oxide adducts was obtained.

The resultant reaction product and 1% by mass aqueous solution of sodium hydroxide were loaded into a first mixing tank of a mixer/settler-type apparatus at 14.8 L/hr and 3.7 L/hr, respectively, stirred at 95° C. for 15 minutes, and washed. Thereafter, the mixture was transferred into a first settling tank of the mixer/settler-type apparatus, and left to stand at 75° C. for 30 minutes in the first settling tank to separate into an organic layer containing ethylene oxide adducts (organic layer 1-1) and an aqueous layer. This organic layer (organic layer 1-1) and water were loaded into a second mixing tank of the mixer/settler-type apparatus at 14.8 L/hr and 3.7 L/hr, respectively, stirred at 95° C. for 15 minutes, and washed. Thereafter, the mixture was transferred into a second settling tank of the mixer/settler-type apparatus, and left to stand at 70° C. for 30 minutes in the second settling tank to separate into an organic layer containing an ethylene oxide adduct (1) (organic layer 1-2) and an aqueous layer; thus, a solution (1) containing an ethylene oxide adduct (1) with the average number of moles of added ethylene oxide being 1.6 (alkylene oxide adduct B) was obtained.

For the organic layer obtained (organic layer 1-2), the presence of an emulsified layer was determined by visual observation of the interface between the organic layer and the aqueous layer in the second settling tank. The result of the observation showed that there was completely no emulsified layer (less than 5% of the total area of the liquid surface) in the interface between the organic layer and the aqueous layer. For the organic layer obtained (organic layer 1-2), the presence of crystals in the organic layer in the second settling tank was determined by visual observation. The result of the observation showed that there was completely no crystal in the organic layer.

Next, the solution (1) containing the ethylene oxide adduct (1), which was obtained in the above, was fed to a first distillate remover column (light component separator column), and light components were distilled off at a bottom temperature of 190° C. and a top pressure of 3 hPa and a bottom solution was recovered. The bottom solution was fed to an alcohol recovery column (rectification column) and distilled at a bottom temperature of 190° C. and a top pressure of 25 hPa to distill off unreacted alcohols and fractions with a few moles of added EO; thus, a secondary alcohol ethoxylate precursor (2) was obtained. The average number of moles of added ethylene oxide (p in the Formula (2)) in the secondary alcohol ethoxylate precursor (2) obtained was determined to be 2.9. Hue (APHA) of the secondary alcohol ethoxylate precursor (2) obtained was evaluated in accordance with the method described in Example 1, and found to be 20 to 30.

A secondary alcohol ethoxylate (6) was obtained in the same manner as in Example 1, except that the resultant secondary alcohol ethoxylate precursor (2) was used instead in Example 1.

The average number of moles of added ethylene oxide (average number of moles of added EO) in the resultant secondary alcohol ethoxylate (6) was determined in accordance with the method described in Example 1, and found to be 9. The hue (APHA) of the secondary alcohol ethoxylate (6) obtained was evaluated in accordance with the method described in Example 1, and found to be 50 to 55.

Thus, the description of the second part of the present invention has been completed.

The aspects and embodiments of the first and second parts of the present invention will be summarized in the following.

1. A method for producing a secondary alcohol alkoxylate, the method comprising: reacting a secondary alcohol with an alkylene oxide in the presence of a catalyst to obtain a reaction solution containing an alkylene oxide adduct; mixing the reaction solution with water and then leaving the reaction solution to stand at a temperature higher than 60° C. to perform separation into an aqueous layer and an organic layer thereby obtaining a solution containing a secondary alcohol alkoxylate precursor represented by the Formula (1): $C_mH_{2m+1}[O(XO)_nH]$, wherein X represents an alkylene group having one to three carbon atoms, m is 11 to 15, and n is more than 0 and less than 2.1; and purifying the solution to obtain a secondary alcohol alkoxylate represented by the Formula (2): $C_mH_{2m+1}[O(XO)_pH]$, wherein X and m are as defined in the Formula (1), and p is 2.5 to 3.5.

2. The method according to 1., wherein, in the Formula (1), n is more than 1.5 and less than 1.8.

3. The method according to 1. or 2., wherein the separation is performed by mixing the reaction solution with an alkaline aqueous solution to separate into an aqueous layer and an organic layer 1 and then mixing the organic layer 1 with water to separate into an aqueous layer and an organic layer 2.

4. The method according to 3., wherein, in mixing the reaction solution with the alkaline aqueous solution, a mixing ratio by volume between the reaction solution and the alkaline aqueous solution is 1:1 to 8:1.

5. The method according to 3. or 4., wherein, in mixing the organic layer 1 with the water, a mixing ratio by volume between the organic layer 1 and the water is 1:1 to 8:1.

6. The method according to any one of 1. to 5., wherein the catalyst is an acid catalyst.

7. The method according to any one of 1. to 6., wherein the reaction between the secondary alcohol and the alkylene oxide is performed at a temperature of 30° C. or higher and 70° C. or lower.

8. A method for producing a high alkylene oxide adduct of secondary alcohol, the method comprising:

producing a secondary alcohol alkoxylate represented by the Formula (2): $C_mH_{2m+1}[O(XO)_pH]$, wherein X represents an alkylene group having one to three carbon atoms, m is 11 to 15, and p is 2.5 to 3.5, by using the method set forth in any one of 1. to 7.; and adding an alkylene oxide to the secondary alcohol alkoxylate via an inlet and alkylene oxide feeders disposed at n positions, except the inlet, in a tubular reactor, wherein n is an integer of 2 or more, to react the secondary alcohol alkoxylate with the alkylene oxide in the tubular reactor, thereby obtaining a high alkylene oxide adduct of secondary alcohol represented by the Formula (4): $C_mH_{2m+1}$

[O(XO)$_q$H], wherein X represents an alkylene group having one to three carbon atoms, m is 12 to 14, and q is more than 3.5 and 50 or less, wherein the alkylene oxide feeders are disposed in the tubular reactor so as to satisfy the Expression (i) presented below, and the alkylene oxide is added to the secondary alcohol alkoxylate so as to satisfy the Expression (ii) presented below:

[Expression 1]

$$N[X_{n'}, X_{n'+1}]/(n-1) > 0.4 \quad \text{(i)}$$

wherein $N[X_{n'}, X_{n'+1}]$ represents the number of sets of three adjacent alkylene oxide feeders satisfying $X_{n'} < X_{n'+1}$, wherein $X_{n'}$ represents an interval (m) between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor, wherein n' is an integer between 0 or more and n−2 or less, and $X_{n'+1}$ represents an interval (m) between the alkylene oxide feeder $P_{n'+1}$ and an alkylene oxide feeder $P_{n'+2}$ disposed at the (n'+2)th position from the inlet of the tubular reactor; and

[Expression 2]

$$N[Y_{n''}, Y_{n''+1}]/n \geq 0.3 \quad \text{(ii)}$$

wherein $N[Y_{n''}, Y_{n''+1}]$ represents the number of sets of two adjacent alkylene oxide feeders satisfying $Y_{n''} < Y_{n''+1}$, wherein $Y_{n''}$ represents a feeding rate (kg/hr) of alkylene oxide at an alkylene oxide feeder $P_{n''}$ disposed at the n''th position from the inlet of the tubular reactor, wherein n'' is an integer between 0 or more and n−1 or less, and $Y_{n''+1}$ represents a feeding rate (kg/hr) of alkylene oxide at an alkylene oxide feeder $P_{n''+1}$ disposed at the (n''+1)th position from the inlet of the tubular reactor.

9. A secondary alcohol alkoxylate having a hue (APHA) of lower than 45 and represented by the Formula (2): $C_m H_{2m+1}[O(XO)_p H]$, wherein X represents an alkylene group having one to three carbon atoms, m is 12 to 14, and p is 2.5 to 3.5.

10. A method for producing a secondary alcohol alkoxylate, the method comprising adding an alkylene oxide to a secondary alcohol alkoxylate precursor via an inlet and alkylene oxide feeders disposed at n positions, except the inlet, in a tubular reactor, wherein n is an integer of 2 or more, to react the secondary alcohol alkoxylate precursor with the alkylene oxide in the tubular reactor, wherein the alkylene oxide feeders are disposed in the tubular reactor so as to satisfy the Expression (i) presented below, and the alkylene oxide is added to the secondary alcohol alkoxylate so as to satisfy the Expression (ii) presented below:

[Expression 1]

$$N[X_{n'}, X_{n'+1}]/(n-1) > 0.4 \quad \text{(i)}$$

wherein $N[X_{n'}, X_{n'+1}]$ represents the number of sets of three adjacent alkylene oxide feeders satisfying $X_{n'} < X_{n'+1}$, wherein $X_{n'}$ represents an interval (m) between an alkylene oxide feeder $P_{n'}$ disposed at the n'th position from the inlet of the tubular reactor and an alkylene oxide feeder $P_{n'+1}$ disposed at the (n'+1)th position from the inlet of the tubular reactor, wherein n' is an integer between 0 or more and n−2 or less, and $X_{n'+1}$ represents an interval (m) between the alkylene oxide feeder $P_{n'+1}$ and an alkylene oxide feeder $P_{n'+2}$ disposed at the (n'+2)th position from the inlet of the tubular reactor; and

[Expression 2]

$$N[Y_{n''}, Y_{n''+1}]/n \geq 0.3 \quad \text{(ii)}$$

wherein $N[Y_{n''}, Y_{n''+1}]$ represents the number of sets of two adjacent alkylene oxide feeders satisfying $Y_{n''} < Y_{n''+1}$, wherein $Y_{n''}$ represents a feeding rate (kg/hr) of alkylene oxide at an alkylene oxide feeder $P_{n''}$ disposed at the n''th position from the inlet of the tubular reactor, wherein n'' is an integer between 0 or more and n−1 or less, and $Y_{n''+1}$ represents a feeding rate (kg/hr) of alkylene oxide at an alkylene oxide feeder $P_{n''+1}$ disposed at the (n''+1)th position from the inlet of the tubular reactor.

11. The method according to 10., wherein the alkylene oxide feeders are disposed in the tubular reactor so as to satisfy the Expression (i') presented below:

[Expression (i')]

$$N[X_{n'}, X_{n'+1}]/(n-1) > 0.7 \quad \text{(i')}$$

wherein $N[X_{n'}, X_{n'+1}]$ is defined as in the Expression (i).

12. The method according to 10. or 11., wherein, if $X_{n'} < X_{n'+1}$ in the Expression (i) is satisfied, a ratio of the $X_{n'+1}$ to the $X_{n'}$ ($X_{n'+1}/X_{n'}$ ratio) is 1.10 or more.

13. The method according to any one of 1. to 12., wherein the alkylene oxide feeders are disposed at 2 to 30 positions per 1000 m of the tubular reactor.

14. The method according to any one of 10. to 13., wherein the tubular reactor has a U-shaped reaction tube.

15. The method according to any one of 10. to 14., further comprising measuring a temperature at at least one position except the inlet in the tubular reactor.

16. The method according to any one of 10. to 15., wherein the secondary alcohol alkoxylate precursor is represented by the following Formula (C):

[Formula (C)]

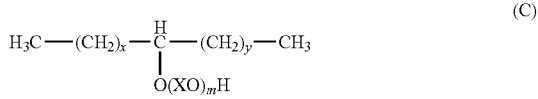

wherein X represents an alkylene group having one to three carbon atoms, a sum total of x and y (x+y) is an integer of 8 to 12, and m is 2.5 or more and 3.5 or less, and obtained by reacting a secondary alcohol with an alkylene oxide in the presence of a catalyst to obtain a reaction solution containing an alkylene oxide adduct A, mixing the reaction solution with water, and then leaving the reaction solution to stand at a temperature higher than 60° C. to perform separation into an aqueous layer and an organic layer thereby obtaining a solution containing an alkylene oxide adduct B represented by the following Formula (B):

[Formula (B)]

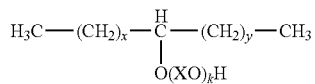

(B)

wherein X, and x and y are defined as in the Formula (C), and k is more than 0 and less than 2.1;
and purifying the solution.

What is claimed is:

1. A method for producing a secondary alcohol alkoxylate, the method comprising:
   reacting a secondary alcohol with an alkylene oxide in the presence of a catalyst in a reactor to obtain a reaction solution containing an alkylene oxide adduct;
   mixing the reaction solution with water and then leaving the reaction solution to stand in a settler at a temperature higher than 60° C. to perform separation into an aqueous layer and an organic layer thereby obtaining a solution containing a secondary alcohol alkoxylate precursor represented by the Formula (1): $C_mH_{2m+1}[O(XO)_nH]$, wherein X represents an alkylene group having one to three carbon atoms, m is 11 to 15, and n is more than 0 and less than 2.1; and purifying the solution to obtain a secondary alcohol alkoxylate represented by the Formula (2): $C_mH_{2m+1}[O(XO)_pH]$, wherein X and m are as defined in the Formula (1), and p is 2.5 to 3.5.

2. The method according to claim 1, wherein, in the Formula (1), n is more than 1.5 and less than 1.8.

3. The method according to claim 1, wherein the separation is performed by mixing the reaction solution with an alkaline aqueous solution to separate into an aqueous layer and an organic layer 1 and then mixing the organic layer 1 with water to separate into an aqueous layer and an organic layer 2.

4. The method according to claim 3, wherein, in mixing the reaction solution with the alkaline aqueous solution, a mixing ratio by volume between the reaction solution and the alkaline aqueous solution is 1:1 to 8:1.

5. The method according to claim 3, wherein, in mixing the organic layer 1 with the water, a mixing ratio by volume between the organic layer 1 and the water is 1:1 to 8:1.

6. The method according to claim 1, wherein the catalyst is an acid catalyst.

7. The method according to claim 1, wherein the secondary alcohol is reacted with the alkylene oxide at a temperature of 30° C. or higher and 70° C. or lower.

8. A method for producing a high alkylene oxide adduct of secondary alcohol, the method comprising:
   producing a secondary alcohol alkoxylate represented by the Formula (2): $C_mH_{2m+1}[O(XO)_pH]$, wherein X represents an alkylene group having one to three carbon atoms, m is 11 to 15, and p is 2.5 to 3.5, by using the method according to claim 1; and
   adding an alkylene oxide to the secondary alcohol alkoxylate via an inlet and alkylene oxide feeders installed at n positions, except the inlet, in a tubular reactor, wherein n is an integer of 2 or more, to react the secondary alcohol alkoxylate with the alkylene oxide in the tubular reactor, thereby obtaining a high alkylene oxide adduct of secondary alcohol represented by the Formula (4): $C_mH_{2m+1}[O(XO)_qH]$, wherein X represents an alkylene group having one to three carbon atoms, m is 12 to 14, and q is more than 3.5 and 50 or less, wherein
   the alkylene oxide feeders are installed in the tubular reactor in such a manner that the Expression (i) presented below is satisfied, and
   the alkylene oxide is added to the secondary alcohol alkoxylate in such a manner that the Expression (ii) presented below is satisfied:

[Expression 1]

$$N[X_{n'}, X_{n'+1}]/(n-1) > 0.4 \quad \text{(i)}$$

wherein $N[X_{n'}, X_{n'+1}]$ denotes the number of sets of three adjacent alkylene oxide feeders satisfying $X_{n'} < X_{n'+1}$, wherein $X_{n'}$ denotes an interval (m) between an alkylene oxide feeder $P_{n'}$ installed at the n'th position counted from the inlet of the tubular reactor and an alkylene oxide feeder $P_{n'+1}$ installed at the (n'+1)th position counted from the inlet of the tubular reactor, wherein n' is an integer between 0 or more and n−2 or less, and $X_{n'+1}$ denotes an interval (m) between the alkylene oxide feeder $P_{n'+1}$ and an alkylene oxide feeder $P_{n'+2}$ installed at the (n'+2)th position counted from the inlet of the tubular reactor; and

[Expression 2]

$$N[Y_{n''}, Y_{n''+1}]/n \geq 0.3 \quad \text{(ii)}$$

wherein $N[Y_{n''}, Y_{n''+1}]$ denotes the number of sets of two adjacent alkylene oxide feeders satisfying $Y_{n''} < Y_{n''+1}$, wherein $Y_{n''}$ denotes a feeding amount (kg/hr) of alkylene oxide at an alkylene oxide feeder $P_{n''}$ installed at the n''th position counted from the inlet of the tubular reactor, wherein n'' is an integer between 0 or more and n−1 or less, and $Y_{n''+1}$ denotes a feeding amount (kg/hr) of alkylene oxide at an alkylene oxide feeder $P_{n''+1}$ installed at the (n''+1)th position counted from the inlet of the tubular reactor.

9. A method for producing a secondary alcohol alkoxylate, the method comprising adding an alkylene oxide to a secondary alcohol alkoxylate precursor via an inlet and alkylene oxide feeders installed at n positions, except the inlet, in a tubular reactor, wherein n is an integer of 2 or more, to react the secondary alcohol alkoxylate precursor with the alkylene oxide in the tubular reactor, wherein
   the alkylene oxide feeders are installed in the tubular reactor in such a manner that the Expression (i) presented below is satisfied, and
   the alkylene oxide is added to the secondary alcohol alkoxylate in such a manner that the Expression (ii) presented below is satisfied:

$$N[X_{n'}, X_{n'+1}]/(n-1) > 0.4 \quad \text{[Expression (i)]}$$

wherein $N[X_{n'}, X_{n'+1}]$ denotes the number of sets of three adjacent alkylene oxide feeders satisfying $X_{n'} < X_{n'+1}$, wherein $X_{n'}$ denotes an interval (m) between an alkylene oxide feeder $P_{n'}$ installed at the n'th position counted from the inlet of the tubular reactor and an alkylene oxide feeder $P_{n'+1}$ installed at the (n'+1)th position counted from the inlet of the tubular reactor, wherein n' is an integer between 0 or more and n−2 or less, and $X_{n'+1}$ denotes an interval (m) between the alkylene oxide feeder $P_{n'+1}$ and an alkylene oxide feeder $P_{n'+2}$ installed at the (n'+2)th position counted from the inlet of the tubular reactor; and $$N[Y_{n''}, Y_{n''+1}]/n \geq 0.3 \qquad \text{[Expression (ii)]}$$

wherein $N[Y_{n''}, Y_{n''+1}]$ denotes the number of sets of two adjacent alkylene oxide feeders satisfying $Y_{n''} < Y_{n''+1}$, wherein $Y_{n''}$ denotes a feeding amount (kg/hr) of alkylene oxide at an alkylene oxide feeder $P_{n''}$ installed at the n''th position counted from the inlet of the tubular reactor, wherein n'' is an integer between 0 or more and n−1 or less, and $Y_{n''+1}$ denotes a feeding amount (kg/hr) of alkylene oxide at an alkylene oxide feeder $P_{n''+1}$ installed at the (n''+1)th position counted from the inlet of the tubular reactor.

10. The method according to claim 9, wherein the alkylene oxide feeders are disposed in the tubular reactor so as to satisfy the Expression (i') presented below:

[Expression (i')]

$$N[X_{n'}, X_{n'+1}]/(n-1) > 0.7 \qquad \text{(i')}$$

wherein $N[X_{n'}, X_{n'+1}]$ is defined as in the Expression (i).

11. The method according to claim 9, wherein, if $X_{n'} < X_{n'+1}$ in the Expression (i) is satisfied, a ratio of the $X_{n'+1}$ to the $X_{n'}$ ($X_{n'+1}/X_{n'}$ ratio) is 1.10 or more.

12. The method according to claim 9, wherein the alkylene oxide feeders are disposed at 2 to 30 positions per 1000 m of the tubular reactor.

13. The method according to claim 9, wherein the tubular reactor has a U-shaped reaction tube.

14. The method according to claim 9, further comprising measuring a temperature at at least one position except the inlet in the tubular reactor.

* * * * *